(12) United States Patent
Civin et al.

(10) Patent No.: US 11,142,746 B2
(45) Date of Patent: *Oct. 12, 2021

(54) HIGH EFFICIENCY MICROFLUIDIC PURIFICATION OF STEM CELLS TO IMPROVE TRANSPLANTS

(71) Applicants: University of Maryland, Baltimore, Baltimore, MD (US); The Trustees of Princeton University, Princeton, NJ (US)

(72) Inventors: Curt I. Civin, Baltimore, MD (US); James C. Sturm, Princeton, NJ (US); Robert H. Austin, Princeton, NJ (US)

(73) Assignees: University of Maryland, Baltimore, Baltimore, MD (US); The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,957

(22) Filed: Nov. 16, 2015

(65) Prior Publication Data

US 2016/0168539 A1 Jun. 16, 2016

Related U.S. Application Data

(63) Continuation of application No. 14/212,885, filed on Mar. 14, 2014, now abandoned.

(60) Provisional application No. 61/799,835, filed on Mar. 15, 2013.

(51) Int. Cl.
| | |
|---|---|
| *A61K 35/17* | (2015.01) |
| *C12N 5/078* | (2010.01) |
| *C12N 5/0789* | (2010.01) |
| *C12N 5/0787* | (2010.01) |
| *A61K 35/15* | (2015.01) |
| *A61K 35/28* | (2015.01) |
| *C12N 5/00* | (2006.01) |

(52) U.S. Cl.
CPC ............ *C12N 5/0634* (2013.01); *A61K 35/15* (2013.01); *A61K 35/17* (2013.01); *A61K 35/28* (2013.01); *C12N 5/0087* (2013.01); *C12N 5/0642* (2013.01); *C12N 5/0647* (2013.01)

(58) Field of Classification Search
CPC .. C12N 5/0634; C12N 5/0087; C12N 5/0647; A61K 35/17
See application file for complete search history.

(56) References Cited

U.S. PATENT DOCUMENTS

| | | |
|---|---|---|
| 4,675,286 A | 6/1987 | Calenoff |
| 4,756,427 A | 7/1988 | Goehde et al. |
| 5,030,002 A | 7/1991 | North, Jr. |
| 5,240,856 A | 8/1993 | Goffe et al. |
| 5,427,663 A | 6/1995 | Austin et al. |
| 5,541,164 A | 7/1996 | Carson et al. |
| 5,676,849 A | 10/1997 | Sammons et al. |
| 5,707,799 A | 1/1998 | Hansmann et al. |
| 5,837,115 A | 11/1998 | Austin et al. |
| 5,872,128 A | 2/1999 | Patel et al. |
| 5,948,278 A | 9/1999 | Sammons et al. |
| 5,968,820 A | 10/1999 | Zborowski et al. |
| 5,981,180 A | 11/1999 | Chandler et al. |
| 6,241,894 B1 | 6/2001 | Briggs et al. |
| 6,268,222 B1 | 7/2001 | Chandler et al. |
| 6,514,295 B1 | 2/2003 | Chandler et al. |
| 6,524,793 B1 | 2/2003 | Chandler et al. |
| 6,528,165 B2 | 3/2003 | Chandler et al. |
| 6,632,652 B1 | 10/2003 | Austin et al. |
| 6,685,841 B2 | 2/2004 | Lopez et al. |
| 6,692,952 B1 | 2/2004 | Braff et al. |
| 6,881,315 B2 | 4/2005 | Iida et al. |
| 6,881,317 B2 | 4/2005 | Huang et al. |
| 6,913,697 B2 | 7/2005 | Lopez et al. |
| 6,949,355 B2 | 9/2005 | Yamanishi et al. |
| 6,960,449 B2 | 11/2005 | Wang et al. |
| 7,150,812 B2 | 12/2006 | Huang et al. |
| 7,276,170 B2 | 10/2007 | Oakey et al. |
| 7,318,902 B2 | 1/2008 | Oakey et al. |
| 7,472,794 B2 | 1/2009 | Oakey et al. |
| 7,682,838 B2 | 3/2010 | Wang et al. |
| 7,735,652 B2 | 6/2010 | Inglis et al. |
| 7,837,944 B2 | 11/2010 | Auner et al. |
| 7,846,393 B2 | 12/2010 | Tai et al. |
| 7,863,012 B2 | 1/2011 | Rao et al. |
| 7,977,095 B2 | 7/2011 | Bonyhadi et al. |
| 7,988,840 B2 | 8/2011 | Huang et al. |
| 7,993,821 B2 | 8/2011 | Chiu et al. |
| 8,008,032 B2 | 8/2011 | Forsyth et al. |
| 8,021,614 B2 | 9/2011 | Huang et al. |
| 8,088,715 B2 | 1/2012 | Bodmer et al. |
| 8,137,912 B2 | 3/2012 | Kapur et al. |
| 8,168,389 B2 | 5/2012 | Shoemaker et al. |
| 8,186,913 B2 | 5/2012 | Toner et al. |
| 8,263,023 B2 | 9/2012 | Le Vot et al. |
| 8,263,404 B2 | 9/2012 | Olken et al. |
| 8,282,799 B2 | 10/2012 | Huang et al. |
| 8,304,230 B2 | 11/2012 | Toner et al. |
| 8,329,422 B2 | 12/2012 | Rao et al. |

(Continued)

FOREIGN PATENT DOCUMENTS

| | | |
|---|---|---|
| CA | 1 248 873 | 1/1989 |
| EP | 1462800 A1 | 9/2004 |

(Continued)

OTHER PUBLICATIONS

Gluckman "Current status of umbilical cord blood hematopoietic stem cell transplanation" 2000 Experimental Hematology, vol. 28, No. 11: 1197-1205.*

(Continued)

*Primary Examiner* — Teresa E Knight
(74) *Attorney, Agent, or Firm* — Law Office of: Michael A. Sanzo, LLC

(57) ABSTRACT

Described herein is a novel, highly efficient system to remove erythrocytes and purify leukocytes would raise the quality of UCB and other transplant grafts, thereby significantly improving patient outcomes.

23 Claims, 22 Drawing Sheets

(56) References Cited

U.S. PATENT DOCUMENTS

| | | |
|---|---|---|
| 8,354,075 B1 | 1/2013 | Tai et al. |
| 8,372,579 B2 | 2/2013 | Toner et al. |
| 8,372,584 B2 | 2/2013 | Shoemaker et al. |
| 8,579,117 B2 | 11/2013 | Sturm et al. |
| 8,585,971 B2 | 11/2013 | Huang et al. |
| 8,783,467 B2 | 7/2014 | Loutherback et al. |
| 8,895,298 B2 | 11/2014 | Toner et al. |
| 8,906,682 B2 | 12/2014 | June et al. |
| 8,921,102 B2 | 12/2014 | Fuchs et al. |
| 8,951,484 B2 | 2/2015 | Bersano-Begey et al. |
| 8,986,966 B2 | 3/2015 | Toner et al. |
| 9,017,942 B2 | 4/2015 | Shoemaker et al. |
| 9,034,658 B2 | 5/2015 | Barber et al. |
| 9,273,355 B2 | 3/2016 | Shoemaker et al. |
| 9,328,156 B2 | 5/2016 | June et al. |
| 9,347,100 B2 | 5/2016 | Shoemaker et al. |
| 9,427,688 B2 | 8/2016 | Reichenbach |
| 9,610,582 B2 | 4/2017 | Kapur et al. |
| 9,629,877 B2 | 4/2017 | Cooper et al. |
| 9,878,327 B2 | 1/2018 | Smith et al. |
| 9,895,694 B2 | 2/2018 | Kapur et al. |
| 9,956,562 B2 | 5/2018 | Huang et al. |
| 10,324,011 B2 | 6/2019 | D'Silva et al. |
| 10,359,429 B2 | 7/2019 | Forsyth et al. |
| 10,391,491 B2 | 8/2019 | Toner |
| 10,844,353 B2 | 11/2020 | Ward et al. |
| 10,852,220 B2 | 12/2020 | D'Silva et al. |
| 10,976,232 B2 | 4/2021 | Ward et al. |
| 10,988,734 B2 | 4/2021 | Ward et al. |
| 2001/0036624 A1 | 11/2001 | Sumita et al. |
| 2002/0005354 A1 | 1/2002 | Spence et al. |
| 2002/0090741 A1 | 7/2002 | Jurgensen et al. |
| 2002/0110835 A1 | 8/2002 | Kumar |
| 2002/0115163 A1 | 8/2002 | Wang et al. |
| 2002/0119482 A1 | 8/2002 | Nelson et al. |
| 2002/0123078 A1 | 9/2002 | Seul et al. |
| 2002/0164825 A1 | 11/2002 | Chen |
| 2003/0049563 A1 | 3/2003 | Iida et al. |
| 2003/0096405 A1 | 5/2003 | Takayama et al. |
| 2003/0113528 A1 | 6/2003 | Moya |
| 2003/0119077 A1 | 6/2003 | Ts'o et al. |
| 2003/0159999 A1 | 8/2003 | Oakey et al. |
| 2003/0180762 A1 | 9/2003 | Tuma et al. |
| 2004/0018116 A1 | 1/2004 | Desmond et al. |
| 2004/0018611 A1 | 1/2004 | Ward et al. |
| 2004/0019300 A1 | 1/2004 | Leonard |
| 2004/0033515 A1 | 2/2004 | Cao |
| 2004/0043506 A1 | 3/2004 | Haussecker et al. |
| 2004/0144651 A1 | 7/2004 | Huang et al. |
| 2004/0166555 A1 | 8/2004 | Braff et al. |
| 2004/0224402 A1 | 11/2004 | Bonyhadi et al. |
| 2004/0229349 A1 | 11/2004 | Daridon |
| 2004/0232074 A1 | 11/2004 | Peters et al. |
| 2005/0061962 A1 | 3/2005 | Mueth et al. |
| 2005/0164158 A1 | 7/2005 | Wang et al. |
| 2005/0207940 A1 | 9/2005 | Butler et al. |
| 2005/0266433 A1 | 12/2005 | Kapur et al. |
| 2005/0272103 A1 | 12/2005 | Chen |
| 2005/0282293 A1 | 12/2005 | Cosman et al. |
| 2006/0035386 A1 | 2/2006 | Hattori et al. |
| 2006/0121624 A1 | 6/2006 | Huang et al. |
| 2006/0128006 A1 | 6/2006 | Gerhardt et al. |
| 2006/0134599 A1 | 6/2006 | Toner et al. |
| 2006/0160243 A1 | 7/2006 | Tang et al. |
| 2006/0223178 A1 | 10/2006 | Barber et al. |
| 2006/0252087 A1 | 11/2006 | Tang et al. |
| 2007/0026381 A1 | 2/2007 | Huang et al. |
| 2007/0026413 A1 | 2/2007 | Fuchs et al. |
| 2007/0026414 A1 | 2/2007 | Fuchs et al. |
| 2007/0026415 A1 | 2/2007 | Fuchs et al. |
| 2007/0026416 A1 | 2/2007 | Fuchs et al. |
| 2007/0026417 A1 | 2/2007 | Fuchs et al. |
| 2007/0026418 A1 | 2/2007 | Fuchs et al. |
| 2007/0026419 A1 | 2/2007 | Fuchs et al. |
| 2007/0026469 A1 | 2/2007 | Fuchs et al. |
| 2007/0042339 A1 | 2/2007 | Toner et al. |
| 2007/0059680 A1 | 3/2007 | Kapur et al. |
| 2007/0059716 A1 | 3/2007 | Balis et al. |
| 2007/0059718 A1 | 3/2007 | Kapur et al. |
| 2007/0059719 A1 | 3/2007 | Kapur et al. |
| 2007/0059774 A1 | 3/2007 | Kapur et al. |
| 2007/0059781 A1 | 3/2007 | Kapur et al. |
| 2007/0072290 A1 | 3/2007 | Hvichia |
| 2007/0099207 A1 | 5/2007 | Fuchs et al. |
| 2007/0160503 A1 | 7/2007 | Sethu et al. |
| 2007/0172903 A1 | 7/2007 | Toner et al. |
| 2007/0187250 A1 | 8/2007 | Huang et al. |
| 2007/0196820 A1 | 8/2007 | Kapur et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2007/0292401 A1 | 12/2007 | Harmon et al. |
| 2008/0070792 A1 | 3/2008 | Stoughton et al. |
| 2008/0090239 A1 | 4/2008 | Shoemaker et al. |
| 2008/0113358 A1 | 5/2008 | Kapur et al. |
| 2008/0124721 A1 | 5/2008 | Fuchs et al. |
| 2008/0248499 A1 | 10/2008 | Chiu et al. |
| 2008/0314161 A1 | 12/2008 | Sparks et al. |
| 2009/0136982 A1 | 5/2009 | Tang et al. |
| 2009/0291443 A1 | 11/2009 | Stoughton et al. |
| 2010/0006479 A1 | 1/2010 | Reichenbach |
| 2010/0055758 A1 | 3/2010 | Kapur et al. |
| 2010/0059414 A1 | 3/2010 | Sturm et al. |
| 2010/0066880 A1 | 3/2010 | Sato et al. |
| 2010/0167337 A1 | 7/2010 | Tsinberg et al. |
| 2010/0233694 A1 | 9/2010 | Kopf-Sill |
| 2010/0234674 A1 | 9/2010 | Wheeler et al. |
| 2010/0291572 A1 | 11/2010 | Stoughton et al. |
| 2010/0297733 A1 | 11/2010 | Lin et al. |
| 2010/0301171 A1 | 12/2010 | Wood |
| 2010/0326916 A1 | 12/2010 | Wrazel et al. |
| 2011/0003293 A1 | 1/2011 | Stoughton et al. |
| 2011/0070642 A1 | 3/2011 | Cayre |
| 2011/0189650 A1 | 8/2011 | Ayliffe et al. |
| 2011/0212440 A1 | 9/2011 | Viovy et al. |
| 2011/0213288 A1 | 9/2011 | Choi et al. |
| 2011/0294186 A1 | 12/2011 | Fuchs et al. |
| 2011/0306043 A1 | 12/2011 | Fuchs et al. |
| 2012/0006728 A1 | 1/2012 | Huang et al. |
| 2012/0006760 A1 | 1/2012 | Toner et al. |
| 2012/0015835 A1 | 1/2012 | Fuchs et al. |
| 2012/0037544 A1* | 2/2012 | Lane ............... B01L 3/502753 209/17 |
| 2012/0063971 A1 | 3/2012 | Carlo et al. |
| 2012/0078531 A1 | 3/2012 | Lo et al. |
| 2012/0100521 A1 | 4/2012 | Soper et al. |
| 2012/0100560 A1 | 4/2012 | Searson et al. |
| 2012/0115755 A1 | 5/2012 | Oh et al. |
| 2012/0171667 A1 | 7/2012 | Shoemaker et al. |
| 2012/0178097 A1 | 7/2012 | Tai et al. |
| 2012/0196273 A1 | 8/2012 | Huang et al. |
| 2012/0258459 A1 | 10/2012 | Huang |
| 2012/0258475 A1 | 10/2012 | Tang et al. |
| 2012/0270209 A1 | 10/2012 | Shah et al. |
| 2012/0295246 A1 | 11/2012 | Faustman et al. |
| 2013/0079251 A1 | 3/2013 | Boles et al. |
| 2013/0083315 A1 | 4/2013 | Lo et al. |
| 2013/0143197 A1 | 6/2013 | Heyneker |
| 2013/0189689 A1 | 7/2013 | Shoemaker et al. |
| 2013/0209988 A1 | 8/2013 | Barber |
| 2013/0210644 A1 | 8/2013 | Stoughton et al. |
| 2013/0260392 A1 | 10/2013 | Forsyth et al. |
| 2013/0288903 A1 | 10/2013 | Kapur et al. |
| 2013/0302796 A1 | 11/2013 | Fuchs et al. |
| 2013/0302797 A1 | 11/2013 | Kopf-Sill et al. |
| 2013/0324418 A1 | 12/2013 | Fuchs et al. |
| 2014/0017776 A1 | 1/2014 | Kopf-Sill |
| 2014/0030788 A1 | 1/2014 | Chen et al. |
| 2014/0051064 A1 | 2/2014 | van den Engh |
| 2014/0093867 A1 | 4/2014 | Burke et al. |
| 2014/0106975 A1 | 4/2014 | Stoughton et al. |
| 2014/0154703 A1 | 6/2014 | Skelley et al. |
| 2014/0227777 A1 | 8/2014 | Choi et al. |
| 2014/0234986 A1 | 8/2014 | Forsyth et al. |

(56) References Cited

U.S. PATENT DOCUMENTS

| | | |
|---|---|---|
| 2014/0342375 A1 | 11/2014 | Grisham et al. |
| 2015/0024482 A1 | 1/2015 | Frigault et al. |
| 2015/0025243 A1 | 1/2015 | Mosher et al. |
| 2015/0064153 A1 | 3/2015 | Civin et al. |
| 2015/0232936 A1 | 8/2015 | Shoemaker et al. |
| 2015/0233931 A1 | 8/2015 | Kopf-Sill et al. |
| 2015/0260711 A1 | 9/2015 | Toner et al. |
| 2015/0268244 A1 | 9/2015 | Cho |
| 2015/0299317 A1 | 10/2015 | Orentas et al. |
| 2015/0316555 A1 | 11/2015 | Fuchs et al. |
| 2015/0344956 A1 | 12/2015 | Kapur et al. |
| 2016/0002737 A1 | 1/2016 | Fuchs et al. |
| 2016/0047735 A1 | 2/2016 | Grisham et al. |
| 2016/0081314 A1 | 3/2016 | Thurston et al. |
| 2016/0103044 A1 | 4/2016 | Kopf-Sill et al. |
| 2016/0139012 A1 | 5/2016 | D'Silva et al. |
| 2016/0244714 A1 | 8/2016 | Spuhler et al. |
| 2016/0339434 A1 | 11/2016 | Toner et al. |
| 2016/0361360 A1 | 12/2016 | Chang et al. |
| 2017/0023578 A1 | 1/2017 | Forsyth et al. |
| 2017/0101680 A1 | 4/2017 | Kopf-Sill et al. |
| 2017/0137515 A1 | 5/2017 | Chang et al. |
| 2017/0166866 A1 | 6/2017 | Lliang et al. |
| 2017/0209864 A1 | 7/2017 | Grisham et al. |
| 2017/0224789 A1 | 8/2017 | Sonavaria et al. |
| 2017/0248508 A1 | 8/2017 | Ward et al. |
| 2017/0255166 A1 | 8/2017 | Toner |
| 2017/0333900 A1 | 11/2017 | Grisham et al. |
| 2018/0038876 A1 | 2/2018 | Arai |
| 2018/0282811 A1 | 10/2018 | Koph-Sill et al. |
| 2019/0071639 A1 | 3/2019 | Ward et al. |
| 2019/0137369 A1 | 5/2019 | D'Silva et al. |
| 2019/0366342 A1 | 12/2019 | Ward et al. |
| 2020/0025656 A1 | 1/2020 | D'Silva et al. |
| 2020/0025657 A1 | 1/2020 | D'Silva et al. |
| 2020/0025669 A1 | 1/2020 | Ward et al. |
| 2020/0056153 A1 | 2/2020 | Ward et al. |
| 2020/0399600 A1 | 12/2020 | Ward et al. |

FOREIGN PATENT DOCUMENTS

| | | |
|---|---|---|
| EP | 1425294 B1 | 7/2008 |
| EP | 1585583 B1 | 4/2010 |
| EP | 1597353 B1 | 11/2010 |
| EP | 2201361 B1 | 5/2011 |
| EP | 1984030 B1 | 5/2013 |
| WO | WO-9116452 A1 | 10/1991 |
| WO | WO-9429707 A1 | 12/1994 |
| WO | WO-0135071 A2 | 5/2001 |
| WO | WO-2004029221 A2 | 4/2004 |
| WO | WO-2004029221 A3 | 5/2004 |
| WO | WO-2004037374 A2 | 5/2004 |
| WO | WO-2004037374 A3 | 10/2004 |
| WO | WO-2004113877 A1 | 12/2004 |
| WO | WO-2005047529 A1 | 5/2005 |
| WO | WO-2005049168 A2 | 6/2005 |
| WO | WO-2005061075 A1 | 7/2005 |
| WO | WO-2005049168 A3 | 9/2005 |
| WO | WO-2006037561 A1 | 4/2006 |
| WO | WO-2006078470 A2 | 7/2006 |
| WO | WO-2006078470 A3 | 9/2006 |
| WO | WO-2006108087 A2 | 10/2006 |
| WO | WO-2006108101 A2 | 10/2006 |
| WO | WO-2006133208 A2 | 12/2006 |
| WO | WO-2007/035585 A2 | 3/2007 |
| WO | WO-2007/035586 A2 | 3/2007 |
| WO | WO-2007035498 A2 | 3/2007 |
| WO | WO-2007079229 A2 | 7/2007 |
| WO | WO-2007079250 A2 | 7/2007 |
| WO | WO-2007147018 A1 | 12/2007 |
| WO | WO-2007147074 A2 | 12/2007 |
| WO | WO-2007147076 A2 | 12/2007 |
| WO | WO-2007147079 A2 | 12/2007 |
| WO | WO-2008008515 A2 | 1/2008 |
| WO | WO-2008017871 A1 | 2/2008 |
| WO | WO-2008111990 A1 | 9/2008 |
| WO | WO-2007079229 A3 | 1/2009 |
| WO | WO-2007079250 A3 | 3/2009 |
| WO | WO-2006108101 A3 | 4/2009 |
| WO | WO-2006108087 A3 | 6/2009 |
| WO | WO-2009076560 A2 | 6/2009 |
| WO | WO 2010/011934 | 1/2010 |
| WO | WO-2010124155 A1 | 10/2010 |
| WO | WO-2010129441 A2 | 11/2010 |
| WO | WO-2010144745 A2 | 12/2010 |
| WO | WO-2011119962 A2 | 9/2011 |
| WO | WO 2012/016136 | 2/2012 |
| WO | WO-2012024194 A2 | 2/2012 |
| WO | WO-2012094642 A2 | 7/2012 |
| WO | WO 2014/004577 A1 | 1/2014 |
| WO | WO-2014046621 A1 | 3/2014 |
| WO | WO-2014116183 A1 | 7/2014 |
| WO | WO-2014145075 A2 | 9/2014 |
| WO | WO-2014145152 A2 | 9/2014 |
| WO | WO 2015/084257 | 6/2015 |
| WO | WO 2015/162211 | 10/2015 |
| WO | WO 2015/164745 | 10/2015 |
| WO | WO-2016019393 A1 | 2/2016 |
| WO | WO 2016/073481 | 5/2016 |
| WO | WO 2017/035262 A1 | 3/2017 |
| WO | WO 2017/176764 | 10/2017 |
| WO | WO 2018/080997 | 5/2018 |
| WO | PCT/US2018/047426 | 8/2018 |
| WO | WO 2019/046052 | 3/2019 |
| WO | WO 2019/222049 | 11/2019 |
| WO | WO 2020/014538 | 1/2020 |

OTHER PUBLICATIONS

Reddy et al. "Isolation of Stem Cells from Human Umbilical Cord Blood" (2007) in Vemuri (eds) Stem Cell Assays. Methods in Molecular Biology, vol. 407, Humana Press , pp. 149-163.*

Al-Fandi, et al. New design for the separation of microorganisms using microfluidic deterministic lateral displacement. Robotics and Computer-Integrated Manufacturing. 2011; 27(2):237-244.

Apocell. ApoStream Technology. Available at http://www.apocell.com/ctc-technology-2/apostreamtm-technology. Accessed Nov. 20, 2015.

CDC. Advanced Abstracting: Breast Cancer Stage of Disease (Part 3). Available at http://www.cdc.gov/cancer/npcr/training/nets/module9/nets9_3.pdf. Accessed Apr. 13, 2015.

Co-pending U.S. Appl. No. 14/717,626, filed May 20, 2015

Co-pending U.S. Appl. No. 14/774,260, filed Sep. 10, 2015.

Co-pending U.S. Appl. No. 14/995,894, filed Jan. 14, 2016.

Cynvenio Technology. LiquidBiopsy Rare Cell Isolation Platform. Available at http://www.cynvenio.com/technology. Accessed on Nov. 20, 2015.

Department of Transport Merchant Shipping Notice No. M.1214. Recommendations to Prevent Contamination of Ships Freshwater Storage and Distribution Systems. Notice to Shipowners, Masters, Fishing Vessel Skippers, Shipbuilders and Repairers. This notice supersedes Notices Nos. M.410, M.633 and M.901. Department of Transport Marine Directorate London WC1V 6LP Jun. 1986. Available at http://www.octomarine.net/mca_flag_regulations/mca_reg_m-1214_contamination_prevention.php. Accessed on Aug. 3, 2015.

D'Silva, et al. Inhibition of clot formation in deterministic lateral displacement arrays for processing large volumes of blood for rare cell capture. Lab Chip. May 21, 2015;15(10):2240-7. doi: 10.1039/c4lc01409j.

Foundation Medicine. Foundation Medicine Initiates Multi-Center Clinical Study Evaluating Its Circulating Tumor DNA (ctDNA) Assay in Multiple Tumor Types. Jul. 28, 2015. Available at http://investors.foundationmedicine.com/releasedetail.cfm?releaseid=924086. Accessed Oct. 27, 2015.

Hodgkinson, et al. Tumorigenicity and genetic profiling of circulating tumor cells in small-cell lung cancer. Nat Med. Aug. 2014;20(8):897-903. doi: 10.1038/nm.3600. Epub Jun. 1, 2014.

ICellate Cancer Cell Detection. Cancer cell detection system for individualized cancer research and detection. Available at http://www.icellate.se. Accessed Oct. 27, 2015.

(56) References Cited

OTHER PUBLICATIONS

International search report and written opinion dated Dec. 29, 2015 for PCT Application No. PCT/US2015/43500.
Maheswaran, et al. Detection of mutations in EGFR in circulating lung-cancer cells. N Engl J Med. Jul. 24, 2008;359(4):366-77. doi: 10.1056/NEJMoa0800668. Epub Jul. 2, 2008.
MedGadget. Clearbridge BioMedics Launching ClearCell FX System for Capturing Circulating Tumor Cell. Available at http://www.medgadget.com/2014/05/clearbridge-biomedics-launching-clearcell-fx-system-for-capturing-circulating-tumor-cell.html. Accessed on Nov. 20, 2015.
Mikolajczyk, et al. Detection of EpCAM-Negative and Cytokeratin-Negative Circulating Tumor Cells in Peripheral Blood. J Oncol. 2011;2011:252361. doi: 10.1155/2011/252361. Epub Apr. 19, 2011.
Office action dated May 18, 2015 for U.S. Appl. No. 14/212,885.
Quirk, W.R. The 2015 Liquid Biopsy Report. Sep. 2015. Piper Jaffray Investment Research.
ReportLinker. Circulating Tumor Cell (CTC) Diagnostics: Technologies and Global Markets. Available at http://www.reportlinker.com/p02009162-summary/Circulating-Tumor-Cell-CTC-Diagnostics-Technologies-and-Global-Markets.html. Accessed Oct. 2, 2015.
Stokstad, Erik. Tests used to ensure ships don't carry deadly cargo draw sharp criticism. Jan. 14, 2015. News.sciencemag.org. Available at http://news.sciencemag.org/biology/2015/01/tests-used-ensure-ships-don-t-carry-deadly-cargo-draw-sharp-criticism. Accessed on Aug. 3, 2015.
Strauss, et al. Abstract P5-10-07: The LiquidBiopsy in metastatic breast cancer (MBC): A novel diagnostic platform for next generation sequencing (NGS) of circulating tumor cells (CTCs). Cancer Research 75, No. 9 Supplement (2015): P5-10.
Vortex Biosciences. Overview: Cancer and CTCs. Available at http://www.vortexbiosciences.com/overview. Accessed Oct. 27, 2015.
Zhang, et al. Electrospun TiO2 Nanofiber-Based Cell Capture Assay for Detecting Circulating Tumor Cells from Colorectal and Gastric Cancer Patients. Adv Mater. May 22, 2012;24(20):2756-60. doi: 10.1002/adma.201200155. Epub Apr. 23, 2012.
Alessandrino, et al. Adverse events occurring during bone marrow or peripheral blood progenitor cell infusion: analysis of 126 cases. Bone Marrow Transplant. Mar. 1999;23(6):533-7.
Alix-Panabieres, et al. Challenges in circulating tumour cell research. Nat Rev Cancer. Sep. 2014;14(9):623-31. doi: 10.1038/nrc3820. Epub Jul. 31, 2014.
Barker, et al. Umbilical cord blood transplantation: current state of the art. Curr Opin Oncol. Mar. 2002;14(2):160-4.
Basford, et al. Umbilical cord blood processing using Prepacyte-CB increases haematopoietic progenitor cell availability over conventional Hetastarch separation. Cell Prolif. Dec. 2009;42(6):751-61. doi: 10.1111/j.1365-2184.2009.00646.x. Epub Sep. 15, 2009.
Bendall, et al. A deep profiler's guide to cytometry. Trends Immunol. Jul. 2012;33(7):323-32. doi: 10.1016/j.it.2012.02.010. Epub Apr. 2, 2012.
Bendall, et al. Single-cell mass cytometry of differential immune and drug responses across a human hematopoietic continuum. Science. May 6, 2011;332(6030):687-96. doi: 10.1126/science.1198704.
Boyum. Isolation of mononuclear cells and granulocytes from human blood. Isolation of monuclear cells by one centrifugation, and of granulocytes by combining centrifugation and sedimentation at 1 g. Scand J Clin Lab Invest Suppl. 1968;97:77-89.
Boyum. Separation of White Blood Cells. Nature. Nov. 21, 1964;204:793-4.
Chen, et al. Rare cell isolation and analysis in microfluidics. Lab Chip. Feb. 21, 2014;14(4):626-45. doi: 10.1039/c3lc90136j.
Chen, et al. Reduction of Output Contamination in On-chip Chemical Treatment and Washing using Separator Walls in Deterministic Lateral Displacement Arrays. Spring Symp Mat Res Soc; San Francisco, CA Apr. 21-25, 2014.
Chou, et al. Sorting by diffusion: an asymmetric obstacle course for continuous molecular separation. Proc Natl Acad Sci U S A. Nov. 23, 1999;96(24):13762-5.
Chow, et al. Whole blood fixation and permeabilization protocol with red blood cell lysis for flow cytometry of intracellular phosphorylated epitopes in leukocyte subpopulations. Cytometry A. Sep. 2005;67(1):4-17.
Colace, et al. Microfluidics and coagulation biology. Annu Rev Biomed Eng. 2013;15:283-303. doi: 10.1146/annurev-bioeng-071812-152406. Epub May 3, 2013.
Copelan. Hematopoietic stem-cell transplantation. N Engl J Med. Apr. 27, 2006;354(17):1813-26.
Coulter® Ac•T diff2™. Safety and Performance at a Remarkable Value. Product information. BeckmanCoulter. Accessed Mar. 13, 2014. https://www.beckmancoulter.com/wsrportal/wsrportal.portal?_nfpb=true&_windowLabel=UCM_RENDERER&_urlType=render&wlpUCM_RENDERER_path=%2Fwsr%2Fdiagnostics%2Fclinical-products%2Fhematology%2Fcoulter-act-diff2-hematology-analyzer%2Findex.htm.
Davis, et al. Deterministic hydrodynamics: taking blood apart. Proc Natl Acad Sci U S A. Oct. 3, 2006;103(40):14779-84. Epub Sep. 25, 2006.
Davis, J. Microfluidic separation of blood components through deterministic lateral displacement. Ph.D. Thesis, Princeton University, 2008 (http://www.princeton.edu/~sturmlab/theses/Davis-Thesis.pdf).
Ernst, et al. Efficacy of High-Dose Bolus Tirofiban Compared to Regular-Dose Glycoprotein IIb/IIIa Inhibitors on Platelet Aggregation Inhibition in Myocardial Infarction Patients Treated with Primary Angioplasty. European Society of Cardiology. Aug. 2003; Abstract 239.
Fiorini, et al. Disposable microfluidic devices: fabrication, function, and application. Biotechniques. Mar. 2005;38(3):429-46.
Flow Cytometry and Sorting Core Facility. One-step fix/perm Protocol. St. Michael's Hospital, Toronto, Ontario, Canada. Accessed Aug. 26, 2014. http://www.stmichaelshospital.com/research/facilities/docs/Protocol1-Onestep-Fix-perm.doc.
Gajkowska, et al. Flow cytometric enumeration of CD34+ hematopoietic stem and progenitor cells in leukapheresis product and bone marrow for clinical transplantation: a comparison of three methods. Folia Histochem Cytobiol. 2006;44(1):53-60.
Geffken, et al. The measurement of fibrinogen in population-based research. Studies on instrumentation and methodology. Arch Pathol Lab Med. Nov. 1994;118(11):1106-9.
Gervais, L. Capillary Microfluidic Chips for Point-of-Care Testing: from Research Tools to Decentralized Medical Diagnostics. Lausanne: EPFL, 2011.
Gluckman, et al. Outcome of cord-blood transplantation from related and unrelated donors. Eurocord Transplant Group and the European Blood and Marrow Transplantation Group. N Engl J Med. Aug. 7, 1997;337(6):373-81.
Gutensohn, et al. Semi-automated flow cytometric analysis of CD34-expressing hematopoietic cells in peripheral blood progenitor cell apheresis products. Transfusion. Nov.-Dec. 1999;39(11-12):1220-6.
Han, et al. Separation of long DNA molecules in a microfabricated entropic trap array. Science. May 12, 2000;288(5468):1026-9.
Hematopoietic Stem Cells . In Stem Cell Information. Bethesda, MD: National Institutes of Health, U.S. Department of Health and Human Services, 2011 [cited Monday, Mar. 10, 2014] Available at <http://stemcells.nih.gov/info/scireport/pages/chapter5.aspx>.
Herault, et al. A rapid single-laser flow cytometric method for discrimination of early apoptotic cells in a heterogenous cell population. Br J Haematol. Mar. 1999;104(3):530-7.
Herold, et al. Lab on a Chip Technology: Biomolecular separation and analysis. (edited) vol. 2. Horizon Scientific Press, 2009.
Holm, et al. Separation of parasites from human blood using deterministic lateral displacement. Lab Chip. Apr. 7, 2011;11(7):1326-32. doi: 10.1039/c0lc00560f. Epub Feb. 18, 2011. Supplemental Information.
Huang, et al. A DNA prism for high-speed continuous fractionation of large DNA molecules. Nat Biotechnol. Oct. 2002;20(10):1048-51. Epub Sep. 3, 2002.

(56) References Cited

OTHER PUBLICATIONS

Huang, et al. A microfluidics approach for the isolation of nucleated red blood cells (NRBCs) from the peripheral blood of pregnant women. Prenat Diagn. Oct. 2008;28(10):892-9. doi: 10.1002/pd.2079.

Huang, et al. Continuous particle separation through deterministic lateral displacement. Science. May 14, 2004;304(5673):987-90.

Huang, et al. Role of molecular size in ratchet fractionation. Phys Rev Lett. Oct. 21, 2002;89(17):178301. Epub Oct. 4, 2002.

Igout, et al. Evaluation of the coulter LH 750 haematology analyzer compared with flow cytometry as the reference method for WBC, platelet and nucleated RBC count. Clin Lab Haematol. Feb. 2004;26(1):1-7.

Inglis, et al. Critical particle size for fractionation by deterministic lateral displacement. Lab Chip. May 2006;6(5):655-8. Epub Mar. 17, 2006.

Inglis, et al. Scaling deterministic lateral displacement arrays for high throughput and dilution-free enrichment of leukocytes. J. Micromech. Microeng. 2011; 21:054024.

International search report and written opinion dated Jan. 9, 2015 for PCT Application No. US2014/029866.

International search report and written opinion dated Aug. 27, 2014 for PCT Application No. US2014/029736.

Karabacak, et al. Microfluidic, marker-free isolation of circulating tumor cells from blood samples. Nat Protoc. Mar. 2014;9(3):694-710. doi: 10.1038/nprot.2014.044. Epub Feb. 27, 2014.

Keung, et al. Cardiac arrhythmia after infusion of cryopreserved stem cells. Bone Marrow Transplant. Sep. 1994;14(3):363-7.

Kurtzberg, et al. Results of the cord blood transplantation (COBLT) study unrelated donor banking program. Transfusion. Jun. 2005;45(6):842-55.

Lasky, et al. In utero or ex utero cord blood collection: which is better? Transfusion. Oct. 2002;42(10):1261-7.

Li, et al. Knock-in of an internal tandem duplication mutation into murine FLT3 confers myeloproliferative disease in a mouse model. Blood. Apr. 1, 2008;111(7):3849-58. doi: 10.1182/blood-2007-08-109942. Epub Feb. 1, 2008.

Loutherback, et al. Critical size, dynamic range, and throughput improvements in sorting by deterministic lateral displacement enabled by triangular posts. Presented at the Symposium of the Materials Research Society, San Francisco, CA, Apr. 2009.

Loutherback, et al. Deterministic microfluidic ratchet. Phys Rev Lett. Jan. 30, 2009;102(4):045301. Epub Jan. 26, 2009.

Loutherback, et al. Deterministic separation of cancer cells from blood at 10 mL/min. AIP Adv. Dec. 2012;2(4):42107. Epub Oct. 3, 2012.

Loutherback, et al. Improved performance of deterministic lateral displacement arrays with triangular posts. Microfluid Nanofluid (2010) 9:1143-1149.

Loutherback. Microfluidic devices for high throughput cell sorting and chemical treatment. Princeton University. Dissertation. Nov. 2011.

Loutherback. Parallelized Microfluidic Separations for Large-scale Dewatering of Biofuel Algae. Symp. Mat. Res. Soc., Nov. 29, 2010, Boston, MA. Abstract # S4.18.

Mandy, et al. Flow Cytometry Principles, Chapter 25. In: Vo-Dinh T, editor. Biomedical Photonics Handbook: CRC Press; 2003. p. 1-20.

Martinez-Lopez, et al. Prognostic value of deep sequencing method for minimal residual disease detection in multiple myeloma. Blood. May 15, 2014;123(20):3073-9. doi: 10.1182/blood-2014-01-550020. Epub Mar. 19, 2014.

Maus, et al. Adoptive immunotherapy for cancer or viruses. Annu Rev Immunol. 2014;32:189-225. doi: 10.1146/annurev-immunol-032713-120136. Epub Jan. 9, 2014.

McGrath, et al. Deterministic lateral displacement for particle separation: a review. Lab Chip. Sep. 30, 2014;14(21):4139-58. doi: 10.1039/c4lc00939h.

Milone, et al. Adverse events after infusions of cryopreserved hematopoietic stem cells depend on non-mononuclear cells in the infused suspension and patient age. Cytotherapy. 2007;9(4):348-55.

Moore, et al. High dimensional flow cytometry comes of age. European Pharmaceutical Review. 2012; 17(4):20-4.

Morton, et al. Crossing microfluidic streamlines to lyse, label and wash cells. Lab Chip. Sep. 2008;8(9):1448-53. doi: 10.1039/b805614e. Epub Jul. 23, 2008.

Nagrath, et al. Isolation of rare circulating tumour cells in cancer patients by microchip technology. Nature. Dec. 20, 2007;450(7173):1235-9.

Office action dated Sep. 2, 2014 for U.S. Appl. No. 13/803,741.

Ozkumur, et al. Inertial Focusing for Tumor Antigen-Dependent and -Independent Sorting of Rare Circulating Tumor Cells. Sci Transl Med. Apr. 3, 2013;5(179):179ra47. doi: 10.1126/scitranslmed.3005616.

Ranjan, et al. DLD pillar shape design for efficient separation of spherical and non-spherical bioparticles. Lab Chip. Sep. 30, 2014;14(21):4250-62. doi: 10.1039/c4lc00578c.

Rocha, et al. Improving outcomes of cord blood transplantation: HLA matching, cell dose and other graft- and transplantation-related factors. Br J Haematol. Oct. 2009;147(2):262-74. doi: 10.1111/j.1365-2141.2009.07883.x.

Rocha, et al. Umbilical cord blood transplantation. Curr Opin Hematol. Nov. 2004;11(6):375-85.

Rubinstein, et al. Outcomes among 562 recipients of placental-blood transplants from unrelated donors. N Engl J Med. Nov. 26, 1998;339(22):1565-77.

Rubinstein, et al. Processing and cryopreservation of placental/umbilical cord blood for unrelated bone marrow reconstitution. Proc Natl Acad Sci U S A. Oct. 24, 1995;92(22):10119-22.

Savage, et al. Functional self-association of von Willebrand factor during platelet adhesion under flow. Proc Natl Acad Sci U S A. Jan. 8, 2002;99(1):425-30. Epub Dec. 26, 2001.

Solves, et al. A new automatic device for routine cord blood banking: critical analysis of different volume reduction methodologies. Cytotherapy. 2009;11(8):1101-7. doi: 10.3109/14653240903253865.

Solves, et al. Comparison between two strategies for umbilical cord blood collection. Bone Marrow Transplant. Feb. 2003;31(4):269-73.

Sommanson. Deterministic lateral separation of cells. Lund University. Master Thesis. 2006.

Spectrolyse blood collection tubes. American Diagnostic Inc. 2010.

Stroncek, et al. Adverse reactions in patients transfused with cryopreserved marrow. Transfusion. Jul.-Aug. 1991;31(6):521-6.

TriTEST CD3 FITC/CD19 PE/CD45 PerCP Reagent. Informational package insert. BD Biosciences. Aug. 2010.

Tsao, et al. Bonding of thermoplastic polymer microfluidics. Microfluidics and Nanofluidics. Jan. 2009, vol. 6, Issue 1, pp. 1-16.

Turner, et al. Confinement-induced entropic recoil of single DNA molecules in a nanofluidic structure. Phys Rev Lett. Mar. 25, 2002;88(12):128103. Epub Mar. 12, 2002.

Van Lochem, et al. Immunophenotypic differentiation patterns of normal hematopoiesis in human bone marrow: reference patterns for age-related changes and disease-induced shifts. Cytometry B Clin Cytom. Jul. 2004;60(1):1-13.

Wagner, et al. Umbilical cord blood transplantation: the first 20 years. Semin Hematol. Jan. 2010;47(1):3-12. doi: 10.1053/j.seminhematol.2009.10.011.

Wang, et al. Single cell analysis: the new frontier in 'omics'. Trends Biotechnol. Jun. 2010;28(6):281-90. doi: 10.1016/j.tibtech.2010.03.002. Epub Apr. 29, 2010.

Wood. Ten-Color Immunophenotyping of Hematopoietic Cells. Current protocols in cytometry. John Wiley & Sons, Inc., 2001.

Yang, et al. Microfluidic device fabrication by thermoplastic hot-embossing. Methods Mol Biol. 2013;949:115-23. doi: 10.1007/978-1-62703-134-9_8.

Yu, et al. A microfluidic approach for whole blood leucocyte isolation for leucocyte immunophenotyping by flow cytometry. Poster submitted to CYTO2012 in Apr. 2012. Cited by permission.

(56) References Cited

OTHER PUBLICATIONS

XXVII Congress of the International Society for Advancement of Cytometry (ISAC) Congress Center Leipzig. Leipzig, Germany. Jun. 23-27, 2012.
Zambelli, et al. Clinical toxicity of cryopreserved circulating progenitor cells infusion. Anticancer Res. Nov.-Dec. 1998;18(6B):4705-8.
Zenhausern, et al. Fatal cardiac arrhythmia after infusion of dimethyl sulfoxide-cryopreserved hematopoietic stem cells in a patient with severe primary cardiac amyloidosis and end-stage renal failure. Ann Hematol. Sep. 2000;79(9):523-6.
Zhang, et al. Applications of Microfluidics in Stem Cell Biology. Bionanoscience. Dec. 1, 2012;2(4):277-286.
Zhang, et al. Label-free enrichment of functional cardiomyocytes using microfluidic deterministic lateral flow displacement. PLoS One. 2012;7(5):e37619. doi: 10.1371/journal.pone.0037619. Epub May 29, 2012.
Zingsem, et al. Cord blood processing with an automated and functionally closed system. Transfusion. Jun. 2003;43(6):806-13, Dec. 25, 2016.
International Preliminary Examination Report for PCT/US2014/029736, which is international stage of co-pending U.S. Appl. No. 14/774,260, dated Sep. 15, 2015.
Amended claims filed for EP 2014763363.0, which is a European counterpart of co-pending U.S. Appl. No. 14/774,260, filed Apr. 28, 2016.
Supplementary European Search Report for EP 2014763363.0 dated Jul. 1, 2016.
European Search Opinion for EP 2014763363.0 dated Jul. 1, 2016.
Amended claims and Response to European Search Opinion for EP 2014763363.0, filed May 4, 2017.
Examination Report for 2014763363.0, dated Sep. 13, 2017.
Translation of amended claims filed in China for CN 2014800285714, which is a Chinese counterpart of co-pending U.S. Appl. No. 14/774,260.
Office Action for CN 2014800285714 with English language summary attached to its front, dated May 5, 2017.
Translation of amended claims filed in response to Office Action for CN 2014800285714, filed Oct. 9, 2017.
U.S. Appl. No. 14/774,260, filed Sep. 10, 2015, 2016/0139012 A1, May 19, 2016, D'Silva, et al.
U.S. Appl. No. 14/774,268, filed Sep. 10, 2015, 2016/0047735 A1, Feb. 18, 2016, Grisham, et al.
U.S. Appl. No. 15/478,405, filed Apr. 4, 2017, 2017/0333900 A1, Nov. 23, 2017, Grisham, et al.
U.S. Appl. No. 15/329,753, filed Jan. 27, 2017, 2017/0209864 A1, Jul. 27, 2017, Grisham, et al.
U.S. Appl. No. 15/204,693, filed Jul. 7, 2016, 2017/0101680 A1, Apr. 13, 2017, Kopf-Sill, et al.
U.S. Appl. No. 14/995,894, filed Jan. 14, 2016, 2017/0023578 A1, Jan. 26, 2017, Forsyth, et al.
U.S. Appl. No. 15/595,548, filed May 15, 2017, 2017/0248508 A1, Aug. 31, 2017, Ward, et al.
Restriction Requirement for co-pending U.S. Appl. No. 14/774,260, dated Oct. 4, 2017.
Response to Restriction Requirement for co-pending U.S. Appl. No. 14/774,260, filed Dec. 9, 2017.
Amendment to Accompany Response to Restriction Requirement for co-pending U.S. Appl. No. 14/774,260, filed Dec. 9, 2017.
U.S. Appl. No. 15/595,548, filed May 15, 2017, Ward.
Bauer, J. Advances in cell separation: recent developments in counterflow centrifugal elutriation and continuous flow cell separation. Journal of Chromatography. 1999;722:55-69.
Beech, et al. Sorting cells by size, shape and deformability. Lab Chip. Mar. 21, 2012;12(6):1048-51. doi: 10.1039/c2lc21083e. Epub Feb. 10, 2012.
Beech, et al. Tipping the balance of deterministic lateral displacement devices using dielectrophoresis. Lab Chip. Sep. 21, 2009;9(18):2698-706. doi: 10.1039/b823275j. Epub Jun. 15, 2009.
Bowman, et al. Inertia and scaling in deterministic lateral displacement. Biomicrofluidics. Dec. 5, 2013;7(6):64111. doi: 10.1063/1.4833955. eCollection 2013.
Chang, et al. A continuous multi-size particle separator using negative dielectrophoretic virtual pillars induced by a planar spot electrode array. Proceedings of the IEEE International Conference on Micro Electro Mechanical Systems (MEMS), Feb. 2007.
Chen, et al. Microfluidic chemical processing with on-chip washing by deterministic lateral displacement arrays with separator walls. Biomicrofluidics. Sep. 9, 2015;9(5):054105. doi: 10.1063/1.4930863. eCollection 2015.
Collins, et al. Particle separation using virtual deterministic lateral displacement (vDLD). Lab Chip. May 7, 2014;14(9):1595-603. doi: 10.1039/c3lc51367j. Epub Mar. 18, 2014.
Expired U.S. Appl. No. 62/032,520, filed Aug. 1, 2014.
Expired U.S. Appl. No. 60/414,065, filed Sep. 27, 2002.
Expired U.S. Appl. No. 60/414,102, filed Sep. 27, 2002.
Expired U.S. Appl. No. 60/420,756, filed Oct. 23, 2002.
Expired U.S. Appl. No. 60/478,299, filed Jun. 13, 2003.
Expired U.S. Appl. No. 60/549,610, filed Mar. 3, 2004.
Expired U.S. Appl. No. 60/703,833, filed Jul. 29, 2005.
Expired U.S. Appl. No. 61/799,835, filed Mar. 15, 2013.
Expired U.S. Appl. No. 61/800,222, filed Mar. 15, 2013.
Devendra, et al. Deterministic fractionation of binary suspensions moving past a line of microposts. Microfluidics and Nanofluidics 17(3):519, Apr. 2014.
D'Silva, Joseph. Post Geometry Design for High-Throughput Harvesting of Nucleated Cells from Blood with Minimal Erythrocyte Contamination Using DLD Arrays. Chapter 4 from High-Throughput Microfluidic Capture of Rare Cells from Large Volumes of Blood. Princeton University, Ph.D. dissertation, May 2016, pp. 53-113.
Holmes, et al. Separation of blood cells with differing deformability using deterministic lateral displacement(†).Interface Focus. Dec. 6, 2014;4(6):20140011. doi: 10.1098/rsfs.2014.0011.
Huh, et al. Gravity-driven microhydrodynamics-based cell sorter (microHYCS) for rapid, inexpensive, and efficient cell separation and size-profiling. 2nd Annual International IEEE-EMBS Special Topic Conference on Microtechnology in Medicine and Biology. Madison, Wisconsin USA; May 2-4, 2002:466-469.
Inglis, et al. Determining blood cell size using microfluidic hydrodynamics. J Immunol Methods. Jan. 1, 2008;329(1-2):151-6. Epub Nov. 1, 2007.
Jiang, et al. Fractionation by shape in deterministic lateral displacement microfluidic devices. Microfluidics and Nanofluidics. Aug. 2015, vol. 19, Issue 2, pp. 427-434.
Kenis, et al. Microfabrication Inside Capillaries Using Multiphase Laminar Flow Patterning. Science. 1999; 285:83-85.
Khodaee, et al. Numerical Simulation of Separation of Circulating Tumor Cells from Blood Stream in Deterministic Lateral Displacement (DLD) Microfluidic Channel. Journal of Mechanics, vol. 32, Issue 04, Aug. 2016, pp. 463-471. Copyright © The Society of Theoretical and Applied Mechanics 2016. Published online: Dec. 21, 2015.
Kruger, et al. Deformability-based red blood cell separation in deterministic lateral displacement devices—A simulation study. Biomicrofluidics. Oct. 13, 2014;8(5):054114. doi: 10.1063/1.4897913. eCollection 2014.
Liu, et al. Rapid isolation of cancer cells using microfluidic deterministic lateral displacement structure. Biomicrofluidics. Jan. 7, 2013;7(1):11801. doi: 10.1063/1.4774308. eCollection 2013.
Long, et al. Multi-directional sorting modes in deterministic lateral displacement devices. Physical Review E 78, 046304 (2008).
Lubbersen, et al. Particle suspension concentration with sparse obstacle arrays in a flow channel. Chemical Engineering and Processing: Process Intensification, 95:90-97, 2015.
Oakey et al. Laminar Flow-Based Separations at the Microscale. Biotechnology Progress. 2002; pp. 1439-1442.
Quek, et al. Separation of deformable particles in deterministic lateral displacement devices. Phys Rev E Stat Nonlin Soft Matter Phys. May 2011;83(5 Pt 2):056301. Epub May 2, 2011.
Sollier et al. Size-selective collection of circulating tumor cells using Vortex technology. Lab Chip 14(1):63-77 (2014).

(56) References Cited

OTHER PUBLICATIONS

Takayama, et al. Patterning Cells and Their Environments Using Multiple Laminar Fluid Flows in Capillary Networks. Proceedings of the National Academy of Sciences of the United States of America. 1999:5545-5548.
Toner, et al. Blood-on-a-Chip. Annu. Rev. Biomed. Eng. 7:77-103, C1-C3 (2005).
Vona, et al. Isolation by size of epthelieal tumor cells. American Journal of Pathology. 2000; 156:57-63.
Yamada, et al. Pinched flow fractionation: continuous size separation of particles utilizing a laminar flow profile in a pinched microchannel. Anal Chem. Sep. 15, 2004;76(18):5465-71.
Ye, et al. Effects of the particle deformability on the critical separation diameter in the deterministic lateral displacement device. Journal of Fluid Mechanics, 743, pp. 60-74 doi:10.1017/jfm.2014.22.
Zeming, et al. Asymmetrical Deterministic Lateral Displacement Gaps for Dual Functions of Enhanced Separation and Throughput of Red Blood Cells. Sci Rep. Mar. 10, 2016;6:22934. doi: 10.1038/srep22934.
Zeming, et al. Rotational separation of non-spherical bioparticles using l-shaped pillar arrays in a microfluidic device. Nat Commun. 2013;4:1625. doi: 10.1038/ncomms2653.
Zhang, et al. Behavior of rigid and deformable particles in deterministic lateral displacement devices with different post shapes. J Chem Phys. Dec. 28, 2015;143(24):243145. doi: 10.1063/1.4937171.
U.S. Appl. No. 60/414,258, filed Apr. 8, 2004 (posted by WIPO), Toner, et al.
International Search Report for PCT/US2016/048455, completed Oct. 17, 2016; which is related to copending U.S. Appl. No. 15/595,548.
Written Opinion for PCT/US2016/048455, completed Oct. 17, 2016; which is related to copending U.S. Appl. No. 15/595,548.
International Preliminary Report on Patentability for PCT/US2016/048455, dated Feb. 17, 2018; which is related to copending U.S. Appl. No. 15/595,548.
International Preliminary Report on Patentability for PCT/US2014/029866; international stage of copending U.S. Appl. No. 14/774,268, dated Sep. 15, 2015.
International Preliminary Report on Patentability for PCT/US2015/043500; dated Feb. 7, 2017; which is related to copending U.S. Appl. No. 15/329,753.
Amended Claims and Response to Examination Report for EP 2014763363.0, filed Mar. 20, 2018; counterpart of copending U.S. Appl. No. 14/774,260.
English translation of Office Action with Response for CN 201480028571.4 due May 17, 2018; counterpart of copending U.S. Appl. No. 14/774,260.
Office Action dated Mar. 6, 2018 for copending U.S. Appl. No. 14/774,260.
Supplementary Search Report for EP 14764615, which is the European counterpart of copending U.S. Appl. No. 14/774,268, dated Jul. 1, 2016.
European Search Opinion for EP 14764615, dated Jul. 1, 2016.
Response to European Search Opinion for EP 14764615, filed May 10, 2017.
Amended Claims with Annotations in response to European Search Opinion for EP 14764615, filed May 10, 2017.
Examination Report for EP 14764615, dated Sep. 13, 2017.
Amended Claims and Response to EP Report for EP 14764615, filed Jan. 23, 2018.
English language translation of First Office Action for CN 201480028570X, which is the Chinese counterpart of copending U.S. Appl. No. 14/774,268, dated Feb. 21, 2017.
Clean copy of claims in response to First Office Action for CN 201480028570X, filed Jul. 5, 2017.
Second Office Action for Chinese application 201480028570X, with English language summary attached to the front of the document, dated Nov. 15, 2017.
Clean copy of amended claims in response to Second Office Action for CN 201480028570X, filed Jan. 30, 2018.
Best, et al., "RNA-Seq of Tumor-Educated Platelets Enables Blood-Based Pan-Cancer, Multiclass, and Molecular Pathway Cancer Diagnostics," *Cancer Cell* 28:666-676 (Nov. 2015).
Deng, et al., "Manipulation of magnetic microbeads in suspension using micromagnetic systems fabricated with soft lithography," *Applied Physics Letters* 78:1775 (Mar. 2001).
Harris, et al., "Single-Molecule DNA Sequencing of a Viral Genome," *Science* 320:106 (Apr. 2008).
Kanwar, et al., "Microfluidic device (ExoChip) for On-Chip isolation, quantification and characterization of circulating exosomes," *Lab Chip* 14(11):1891-1900 (Jun. 2014).
Kwon, et al., "Endothelium." Human Adult Stem Cells. Springer, Dordrecht, 73-89, (2009).
Lee, et al., "Exosomes and microvesicles: extracellular vesicles for genetic information transfer and gene therapy," *Human Molecular Genetics* 21 (rev. issue 1):R125-R134 (Aug. 2012).
Liu, et al., "High throughput capture of circulating tumor cells using an integrated microfluidic system," *Biosensors and Bioelectronics* 47:113-119 (2013).
Margulies, et al., "Genome sequencing in microfabricated high-density picolitre reactors," *Nature* 437:376-380 (Sep. 2005).
Soni, et al., "Progress toward Ultrafast DNA Sequencing Using Solid State Nanopores," *Clin. Chem.* 53:1996-2001 (2007).
Zheng, et al., "Deterministic lateral displacement MEMS device for continuous blood cell separation," Micro Electro Mechanical Systems, 2005. 18th IEEE International Conference.
U.S. Appl. No. 15/870,945, filed Jan. 13, 2018, Kopf-Sill, et al.
European Search Opinion and Search Report for EP 15827324.3, EP counterpart of copending U.S. Appl. No. 15/329,753, dated Dec. 12, 2017.
Response to European Search Opinion and Search Report for EP 15827324.3, EP counterpart of copending U.S. Appl. No. 15/329,753, filed Jul. 12, 2018.
Clean copy of amended claims with Response to Search Opinion and Search Report for EP 15827324.3, EP counterpart of copending U.S. Appl. No. 15/329,753, filed Jul. 12, 2018.
Response to Office Action for co-pending U.S. Appl. No. 14/774,260, filed Jun. 6, 2018.
Amended claims filed in Response to $2^{nd}$ Office Action, filed May 16, 2018; (CN 20140028714; Chinese counterpart of copending U.S. Appl. No. 14/774,260).
Restriction Requirement for copending U.S. Appl. No. 14/774,268, dated May 21, 2018.
Response to Restriction Requirement for copending U.S. Appl. No. 14/774,268, filed Aug. 21, 2018.
English language summary of $3^{rd}$ Office Action for CN 201480028570X, which is the Chinese counterpart of copending U.S. Appl. No. 14/774,268, dated May 28, 2018.
English translation of clean copy of amended claims filed in response to 3rd Office Action for CN 201480028570X, which is the Chinese counterpart of copending U.S. Appl. No. 14/774,268, filed Aug. 13, 2018.
Restriction Requirement for copending U.S. Appl. No. 15/329,753, dated Jul. 24, 2018.
Restriction Requirement for copending U.S. Appl. No. 15/478,405, dated Jun. 12, 2018.
Response to Restriction Requirement with accompanying amendment attached for copending U.S. Appl. No. 15/478,405, filed Sep. 12, 2018.
Radisic, et al., "Micro- and nanotechnology in cell separation," *International Journal of Nanomedicine* 1(1):3-14 (2006).
Reddy, et al., "Isolation of Stem Cells from Human Umbical Cord Blood," in Vemuri (eds) Stem Cell Assays. Methods in Molecular Biology vol. 407, Human Press, pp. 149-163 (2007).
Yi, et al., "Microfluidics technology for manipulation and analysis of biological cells," *Analytica Chimica Acta* 560: 1-23 (2006).
U.S. Appl. No. 16/123,056, filed Sep. 6, 2018, D'Silva, et al.
Partial English translation summarizing 3rd Office Action, dated Nov. 5, 2018; (CN 20140028714; Chinese counterpart of U.S. Appl. No. 14/774,260).

(56) References Cited

OTHER PUBLICATIONS

Communication from EPO regarding intention to grant and grant text for EP 2014764615 dated Sep. 25, 2018. EP counterpart of copending U.S. Appl. No. 14/774,268.
Request for Continued Examination for copending U.S. Appl. No. 14/774,260, filed Dec. 18, 2018.
Office Action for copending U.S. Appl. No. 14/774,268, dated Nov. 13, 2018.
Office Action for copending U.S. Appl. No. 15/329,753, dated Oct. 15, 2018.
Office Action for copending U.S. Appl. No. 15/478,405, dated Nov. 19, 2018.
Agrawal, et al., "PDGF upregulates CLEC-2 to induce T regulatory cells," *Oncotarget* 6(30):28621-28632 (Sep. 2015).
Campos-Gonzalez, et al., "Deterministic Lateral Displacement: The Next Generation Car T-Cell Processing?" *SLAS* 23(4): (Jan. 2018).
Chiche-Lapierre, et al., "Comparative analysis of Sepax S-100, COBE 2991, and Manual DMSO Removal Techniques From Cryopreserved Hematopoietic Stem Cell Apheresis Product," *Cytotherapy* 18(6):S47 (2016).
Civin, et al., "Automated Leukocyte Processing by Microfluidic Deterministic Lateral Displacement," *Cytometry A* 89:1073-1083 (2016).
Couzin-Frankel, et al., "Supply of Promising T-Cell Therapy is Strained," *Science* 356:1112 (Jun. 2017).
Disilva, J., "Throughout Microfluidic Capture of Rare Cells from Large Volumes of Blood," A Dissertation Presented to the Faculty of Princeton University in Candidacy for the Degree of Doctor of Philosophy, (May 2016).
Feng, et al., "Maximizing particle concentration in deterministic lateral displacement arrays," *Biomicrofluidics* 11:024121 (published online Apr. 2017).
Fousek, et al., "The Evolution of T-cell Therapies for Solid Malignancies," *Clinical Cancer Research* 21(5):3384-3392 (Aug. 2015).
Hokland, et al., "The Isopaque-Ficoll Method Re-evaluated: Selective Loss of Autologous Rosette-forming Lymphocytes During Isolation of Mononuclear Cells from Human Peripheral Blood," *Scand. J.Immunol.* 11(3):353-356 (Mar. 1980).
Johnson, et al., "Driving Gene-engineered T-cell Immunotherapy of Cancer," *Cell Res.* 27:38-58 (2017).
Koesdjojo, et al., "DLD Microfluidic Purification and Characterization of Intact and Viable Circulating Tumor Cells in Peripheral Blood," *AACR Annual Meeting* Abstract #3956 (2016).
Kurihara, et al., "Imaging Brain Tumors by Targeting Peptide Radiopharmaceuticals through the Blood-Brain Barrier," *Cancer Research* 59(24):6159-6163 (Dec. 1999).
Levine, et al., "Global Manufacturing of CAR T-cell Therapy," *Mol. Therapy: Meth. Clin. Dev.* 4:92-101 (2017).
Li, et al., "Comparison of anti-CD3 and anti-CD28-coated beads with soluble anti-CD3 for expanding Human T-cells: Differing impact on CD8 T-cell phenotype and responsiveness to restimulation," *J. Transl. Med.* 8:104-118 (2010).
Mahnke, et al., "The who's who of T-cell differentiation: Human memory T-cell subsets," *Eur. J. Immunol.* 43:2797-2809 (2013).
Marktkamcham, et al., "The Effects of Anti-CD3/CD28 Coated Beads and IL-2 on Expanded T Cell for Immunotherapy," *Adv. Clin. Exp. Med.* 25:821-828 (2016).
National Cell Manufacturing Consortium. Achieving Large-Scale, Cost-Effective, Reproducible Manufacturing of High Quality Cells. A Technology Roadmap to 20205. (Feb. 2016).
Powell, et al., "Efficient clinical-scale enrichment of lymphocytes for use in adoptive immunotherapy using a modified counterflow centrifugal elutriation program," *Cytotherapy* 11(7):923-935 (2009).
Rhee, M., "Advanced Components of Microfluidic Systems for Bioanalytical Applications," A dissertation submitted in partial fulfillment of the requirements for the degree of Doctor of Philosophy in The University of Michigan, 2009.
Sadelain, et al., "Therapeutic T cell engineering," *Nature* 545:423-431 (May 2017).

Stroncek, et al., "Counter-flow elutriation of clinical peripheral blood mononuclear cell concentrates for the production of dendritic and T cell therapies," *J. Transl. Med.*12:241 (2014).
Trickett, et al., "T-cell Stimulation and Expansion Using Anti-CD3/CD28 Beads," *J/Immunol. Meth.* 275:251-255 (Apr. 2003).
Vonderheide, et al., "Engineering T cells for cancer: our synthetic future," *Immunol. Rev.* 257:7-13 (2014).
Wang, et al., "Clinical manufacturing of CAR T cells: a foundation of promising therapy," *Mol. Ther. Oncolytics* 3:16015 (2016).
Zhang, et al., "Optimized DNA electroporation for primary human T cell engineering," *BMC Biotechnology* 18:4 (2018).
Zhu, et al., "Platelets Provoke Distinct Dynamics of Immune Response by Differentially Regulating $CD4^+$ T-cell Proliferation," *J. Throm. Haem.* 12:1156-1165 (2014).
U.S. Appl. No. 16/108,365, filed Aug. 22, 2018, Ward, et al.
Response to Restriction Requirement with accompanying amendment for copending U.S. Appl. No. 15/329,753, filed Sep. 24, 2018.
Notice of Allowance dated Sep. 19, 2018 for copending U.S. Appl. No. 14/774,260.
Response to Rule 71 Communication for EP 14764615.2, filed by Applicant Jan. 28, 2019; European counterpart of copending U.S. Appl. No. 14/774,268.
Second Communication Under Rule 71(3) for EP 14764615.2, sent by the EPO dated Mar. 7, 2019; European counterpart of copending U.S. Appl. No. 14/774,268.
Proposed Text for Grant for EP 14764615.2, dated Mar. 7, 2019; European counterpart of copending U.S. Appl. No. 14/774,268.
Notice of Allowance for CN 201480028570X (in Chinese); Chinese counterpart of copending U.S. Appl. No. 14/774,268.
Translation of Certificate of Invention Patent for Application CN 201480028570X, sent Apr. 9, 2019; Chinese counterpart of copending U.S. Appl. No. 14/774,268.
Claims for Patent for CN 201480028570X, of Apr. 9, 2019; Chinese counterpart of copending U.S. Appl. No. 14/774,268.
Translation of Filing Information for Divisional of CN 201480028570X, sent Apr. 26, 2019; Chinese counterpart of copending U.S. Appl. No. 14/774,268.
Communication Under Rule 71(3) for EP 14 763 363.0, dated May 24, 2019; European counterpart of copending U.S. Appl. No. 14/774,260.
Proposed text for grant for EP 14 763 363.0, dated May 24, 2019; European counterpart of copending U.S. Appl. No. 14/774,260.
Amended claims filed for CN 20140028714 in response to the 3rd Office Action filed Jan. 23, 2019; Chinese counterpart of copending U.S. Appl. No. 14/774,260.
First Examination Report For EP 15 827 324.3, dated May 24, 2019; European counterpart of copending U.S. Appl. No. 15/329,753.
Supplemental Amendment for copending U.S. Appl. No. 14/774,260, filed Jan. 1, 2019.
Notice of Allowance for copending U.S. Appl. No. 14/774,260, dated Jan. 30, 2019.
Amendment Under 37 CFR 1.312 filed Apr. 21, 2019, for copending U.S. Appl. No. 14/774,260.
Response and Amendment Under 37 CFR 1.312 sent to the USPTO dated Apr. 25, 2019, for copending U.S. Appl. No. 14/774,260.
Issue Notification notifying applicant that patent now U.S. Pat. No. 10,324,011 dated May 29, 2019, for copending U.S. Appl. No. 14/774,260.
Amendment and Response to Office Action filed Apr. 5, 2019, for copending U.S. Appl. No. 14/774,268.
Final Rejection dated May 31, 2019, for copending U.S. Appl. No. 14/774,268.
Amendment and Response to Office Action for copending U.S. Appl. No. 15/478,405, filed Apr. 5, 2019.
Restriction Requirement dated May 30, 2019, for copending U.S. Appl. No. 15/478,405.
Amendment and Response to Office Action for copending U.S. Appl. No. 15/329,753, filed Jan. 30, 2018.
Final Rejection dated May 15, 2019, for copending U.S. Appl. No. 15/329,753.
U.S. Appl. No. 16/343,754, filed Apr. 20, 2019, Ward, et al.
Second Examination Report for EP 15827324.3, dated Jan. 21, 2020; European counterpart of copending U.S. Appl. No. 15/329,753.

(56) References Cited

OTHER PUBLICATIONS

Response to Second Examnination Report for EP 15827324.3, filed Apr. 6, 2020; European counterpart of copending U.S. Appl. No. 15/329,753.
Amended Description filed with the Response to Second Examnination Report for EP 15827324.3, filed Apr. 6, 2020; European counterpart of copending U.S. Appl. No. 15/329,753.
Amended claims filed with the Response to Second Examnination Report for EP 15827324.3, filed Apr. 6, 2020; European counterpart of copending U.S. Appl. No. 15/329,753.
Communication Under Rule 71(3) for EP 15827324.3, dated May 14, 2020; European counterpart of copending U.S. Appl. No. 15/329,753.
Text proposed for Grant for EP 15827324.3, dated May 14, 2020; European counterpart of copending U.S. Appl. No. 15/329,753.
Office Action in Canada for CA 2,942,831, dated Feb. 6, 2020; Canadian counterpart of copending U.S. Appl. No. 14/774,260.
Response to Office Action in Canada for CA 2,942,831, filed Jun. 5, 2020; Canadian counterpart of copending U.S. Appl. No. 14/774,260.
Clean copy of claims filed with Response to Office Action in Canada for CA 2,942,831, filed Jun. 5, 2020; Canadian counterpart of copending U.S. Appl. No. 14/774,260.
Brief English language Summary of Office Action in China for CN 2014800285714, dated Jun. 5, 2020; Chinese counterpart of copending U.S. Appl. No. 14/774,260.
English language copy of claims in CN 2014800285714 at time of Office Action, dated Jun. 5, 2020; Chinese counterpart of copending U.S. Appl. No. 14/774,260.
European Search Report for EP 19199294.0, dated Jan. 8, 2020; European counterpart of copending U.S. Appl. No. 14/774,260.
Claims in EP 19199294.0, filed Jun. 8, 2020, European counterpart of copending U.S. Appl. No. 14/774,260.
Response to Rule 69 Communication for EP 19182687.4, filed May 18, 2020; European counterpart of copending U.S. Appl. No. 14/774,268.
Clean copy of amended claims for EP 19182687.4, filed May 18, 2020; European counterpart of copending U.S. Appl. No. 14/774,268.
Response to Restriction Requirement filed Apr. 10, 2020 for copending U.S. Appl. No. 16/588,137.
Notice of Allowance dated May 11, 2020 for copending U.S. Appl. No. 16/588,137.
Amendment and Response filed Apr. 21, 2020 for copending U.S. Appl. No. 14/774,268.
Amendment and Response filed Apr. 24, 2020 for copending U.S. Appl. No. 14/329,753.
Inglis, David, "Microfluidic Devices for Cell Separation," A Dissertation presented to the faculty of Princeton University, Sep. 2007.
Amended claims for CN 2019103452215 filed with Request for Substantive Examination on Jun. 26, 2019; European counterpart of U.S. Appl. No. 14/774,268.
Request to file divisional of EP 14764615.2, filed Jun. 26, 2019; European counterpart of U.S. Appl. No. 14/774,268.
EPO form for filing of divisional of EP 14764615.2, filed Jun. 26, 2019; European counterpart of U.S. Appl. No. 14/774,268.
Specification and claims for divisional of EP 14764615.2, filed Jun. 26, 2019; European counterpart of U.S. Appl. No. 14/774,268.
Filing receipt for divisional assigning it EP 19182687.4, generated Jun. 26, 2019; European counterpart of U.S. Appl. No. 14/774,268.
Extended European Search Report for EP 19182687.4 dated Oct. 7, 2019; European counterpart of U.S. Appl. No. 14/774,268.
Rule 69 Communication for EP 19182687.4 dated Nov. 25, 2019; European counterpart of U.S. Appl. No. 14/774,268.
Response to Examination Report for EP 15 827 324.3, filed on Aug. 22, 2019; European counterpart of copending U.S. Appl. No. 15/329,753.
Amended claims submitted with Response to Examination Report for EP 15 827 324.3, filed on Aug. 22, 2019; European counterpart of copending U.S. Appl. No. 15/329,753.
Canadian Search Report for CA 2942831 dated Feb. 5, 2019; Canadian counterpart of U.S. Appl. No. 14/774,260.

Response to Final Rejection and RCE filed Sep. 21, 2019 for copending U.S. Appl. No. 15/329,753.
Non Final Office Action dated Jan. 2, 2020 for copending U.S. Appl. No. 15/329,753.
Response to Final Rejection and RCE filed Sep. 21, 2019 for copending U.S. Appl. No. 14/774,268.
Non Final Office Action dated Jan. 2, 2020 for copending U.S. Appl. No. 14/774,268.
Amendment and Response to Restriction Requirement filed Aug. 30, 2019 for copending U.S. Appl. No. 15/478,405.
Final Office Action dated Dec. 4, 2019 for copending U.S. Appl. No. 15/478,405.
Restriction Requirement dated Feb. 12, 2020 for copending U.S. Appl. No. 16/588,137.
Lee, et al., "Continuous medium exchange and optically induced electroporation of cells in an integrated microfluidic system," *Microsystems and Nanoengineering* 1:1-9 (2015).
Song, et al., "Automatic detecting and counting magnetic based-labeled target cells from a suspension in a microfluidic chip," *Electrophoresis* 40:897-905 (2019).
U.S. Appl. No. 16/587,022, filed Sep. 29, 2019, US-2020/0025656 A1, Jan. 23, 2020, D'Silva.
U.S. Appl. No. 16/587,057, filed Sep. 30, 2020, US-2020/0025669 A1, Jan. 23, 2020, Ward.
U.S. Appl. No. 16/588,137, filed Sep. 30, 2020, US-2020/0025657 A1, Jan. 23, 2020, D'Silva.
U.S. Appl. No. 16/662,033, filed Oct. 24, 2020, US-2020/0056153 A1, Feb. 20, 2020, Ward.
Response to European Search Report for EP 19199294.0, with clean copy of the claims attached, filed Aug. 10, 2020, European counterpart of U.S. Appl. No. 14/774,260.
Amended claims filed in Response to Chinese Office Action dated Jun. 5, 2020 for CN 201480028714 (counterpart of U.S. Appl. No. 14/774,260 and U.S. Appl. No. 16/123,056) filed on Oct. 20, 2020.
Decision to grant European patent for EP 15827324.3 (counterpart of U.S. Appl. No. 15/329,753) dated Oct. 1, 2020.
Proposed text for grant for EP 15827324.3 (counterpart of U.S. Appl. No. 15/329,753) dated Oct. 1, 2020.
Allowed claims for EP 15827324.3 (counterpart of U.S. Appl. No. 15/329,753) dated Oct. 1, 2020.
Final Office for copending U.S. Appl. No. 15/329,753, dated Sep. 10, 2020.
Restriction Requirement for copending U.S. Appl. No. 16/123,056, dated Oct. 20, 2020.
Response to Restriction Requirement for copending U.S. Appl. No. 16/123,056, filed Dec. 20, 2020.
Amendment to Accompany Response to Restriction Requirement for copending U.S. Appl. No. 16/123,056, filed Dec. 20, 2020.
Request for Continued Examination for copending U.S. Appl. No. 15/329,753, filed Dec. 24, 2020.
Amendment & Response to Accompany RCE for copending U.S. Appl. No. 15/329,753, filed Dec. 24, 2020.
U.S. Appl. No. 17/009,797, filed Sep. 2, 2020, Ward.
Non-Final Office Action for copending U.S. Appl. No. 15/329,753, dated Feb. 5, 2021.
Final Office Action for copending U.S. Appl. No. 14/774,268, dated Apr. 9, 2021.
Office Action for Canadian application 2,942,831, which is a counterpart of copending U.S. Appl. No. 14/774,260, dated Mar. 12, 2021.
Claims pending in Canadian application 2,942,831 when the Office Action was dated Mar. 12, 2021.
U.S. Appl. No. 17/192,691, filed Mar. 4, 2021, Ward.
English translation of Certificate of Invention for Chinese patent ZL2014800285714 (counterpart of copending U.S. Appl. No. 14/774,260), dated Jun. 11, 2021.
English language summary of Office Action for Chinese CN 2019103452215 with copy of claims attached (counterpart of copending U.S. Appl. No. 14/774,268), dated May 25, 2021.
Notification of filing of divisional application in China; division of CN 2014800285714 with claims attached (corresponding to copending U.S. Appl. No. 14/774,260), filed Jun. 23, 2021.

(56) References Cited

OTHER PUBLICATIONS

Response to Notice of Incomplete Reply for copending U.S. Appl. No. 16/123,056, filed Jun. 30, 2021.
Amendment to Accompany Response to Notice of Incomplete Reply for copending U.S. Appl. No. 16/123,056, filed Jun. 30, 2021.
Response to Non-Final Office Action for copending U.S. Appl. No. 15/329,753, filed Jul. 3, 2021.
Response to Office Action for Canadian application 2,942,831, which is a counterpart of copending U.S. Appl. No. 14/774,260, filed in Canada dated Jul. 8, 2021.

* cited by examiner

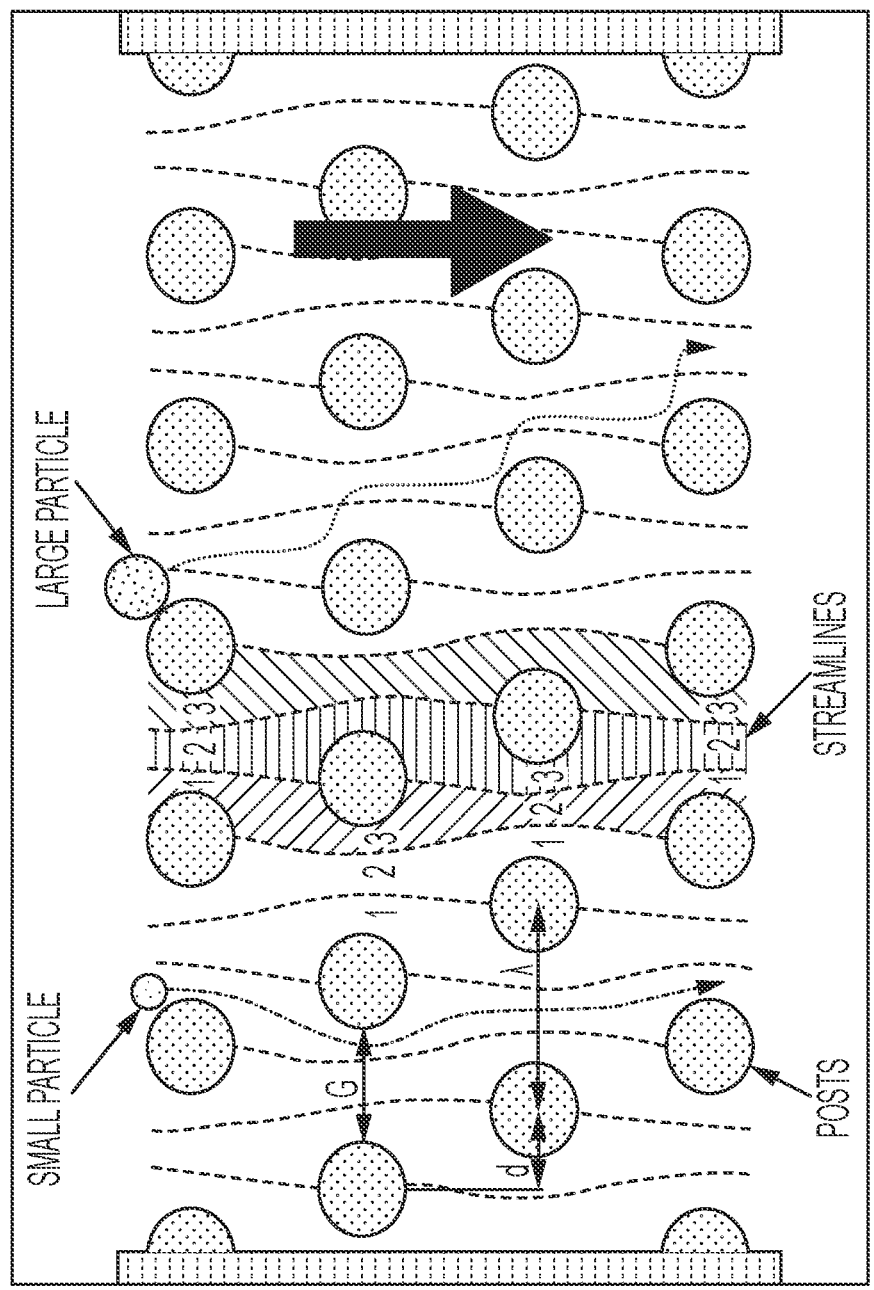

HIGH EFFICIENCY MICROFLUIDIC PURIFICATION OF STEM CELLS TO IMPROVE TRANSPLANTS

CROSS-REFERENCE

This application is a continuation of U.S. application Ser. No. 14/212,885, filed on Mar. 14, 2014; which claims the benefit of U.S. Provisional Application No. 61/799,835, filed Mar. 15, 2013, which are incorporated herein by reference.

STATEMENT AS TO FEDERALLY SPONSORED RESEARCH

This invention was made with government support under Grant No. CA174121, Grant No. HL110574 and Grant No. CA143803 awarded by the National Institutes of Health. The government has certain rights in the invention.

BACKGROUND OF THE INVENTION

There is a critical unmet need for rapid, efficient methods to deplete erythrocytes and recover leukocytes from G-CSF mobilized peripheral blood (PBSC), bone marrow (BM), and especially umbilical cord blood (UCB), prior to cryopreservation. Incomplete erythrocyte removal from transplant grafts increases the risk of harmful side effects in hematopoietic stem cell transplants, while poor recovery of viable leukocytes and CD34+ cells reduces engraftment success and limits the treatable patient population.

SUMMARY OF THE INVENTION

Described herein is a novel, highly efficient system to remove erythrocytes and purify leukocytes would raise the quality of UCB and other transplant grafts, thereby significantly improving patient outcomes.

An aspect of the present disclosure provides a method for isolating stem cells from a sample for transplantation, the method comprising: (a) providing a sample comprising erythrocytes and leukocytes, the sample having a volume of less than 300 mL; (b) depleting the erythrocytes; and (c) enriching the leukocytes to a purity of at least 90%.

In some embodiments, the method further comprises using the stem cells in a transplantation procedure.

In some embodiments, the sample is umbilical cord blood.

In some embodiments, the umbilical cord blood is not cryopreserved.

In some embodiments, the yield of leukocytes is at least 90%.

In some embodiments, the viability of the leukocytes is at least 90%.

In some embodiments, the method is performed in less than 1 hour.

In some embodiments, the method is performed in less than 10 minutes.

In some embodiments, the sample has at least 1000-fold more erythrocytes than leukocytes.

In some embodiments, the method does not use centrifugation, Ficoll-Paque or HES In some embodiments, neither the erythrocytes nor the leukocytes are derivatized or labeled.

In some embodiments, the sample is flowed through a biochip having a plurality of microscopic obstructions that sort the erythrocytes from the leukocytes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In FIG. 2C, small arrows indicate the direction of the fluid along the particle path; the particles generally follow the fluid direction when the fluid flow direction is left-to-right and generally follow the array direction when the fluid flow direction is right-to-left.

FIG. 3A shows simulated trajectories of 1.0-micrometer diameter particles. FIG. 3B shows simulated trajectories of 3.6-micrometer diameter particles. FIG. 3C shows simulated trajectories of 3.2-micrometer diameter particles. In these diagrams, the 1.0-micrometer diameter particles are smaller than the critical size of the array in both fluid flow directions, the 3.6-micrometer diameter particles are larger than the critical size of the array in both fluid flow directions, and the 3.2-micrometer diameter particles are smaller than the critical size of the array in one (right-to-left) flow direction, but larger than the critical size of the array in the other (left-to-right) flow direction.

FIG. 16A shows a schematic top view drawing of the chip;

DETAILED DESCRIPTION OF THE INVENTION

The disclosure relates generally to the field of separation of particles such as spheres, cells, viruses, and molecules. In particular, the disclosure relates to separation of particles based on their flow behavior in a fluid-filled field of obstacles in which advective transport of particles by a moving fluid overwhelms the effects of diffusive particle transport.

Separation of particles by size or mass is a fundamental analytical and preparative technique in biology, medicine, chemistry, and industry. Conventional methods include gel electrophoresis, field-flow fractionation, sedimentation and size exclusion chromatography. More recently, separation of particles and charged biopolymers has been described using arrays of obstacles through particles pass under the influence of fluid flow or an applied electrical field. Separation of particles by these obstacle-array devices is mediated by interactions among the biopolymers and the obstacles and by the flow behavior of fluid passing between the obstacles.

A variety of microfabricated sieving matrices have been disclosed for separating particles (Chou et. al., 1999, Proc. Natl. Acad. Sci. 96:13762; Han, et al., 2000, Science 288: 1026; Huang et al., 2002, Nat. Biotechnol. 20:1048; Turner et al., 2002, Phys. Rev. Lett. 88(12):128103; Huang et al., 2002, Phys. Rev. Lett. 89:178301; U.S. Pat. Nos. 5,427,663; 7,150,812; 6,881,317). These matrices depend on accurate fabrication of small features (e.g., posts in a microfluidic channel) The accuracy with which small features can be fabricated is limited in all micro-fabrication methods, especially as feature size decreases. The strength and rigidity of materials in which small features of fabricated can also limit the practical usefulness of the fabricated device. Furthermore, the small size of the gaps between obstacles in such matrices can render the matrices susceptible to clogging by particles too large to fit between the obstacles. Micrometer- and nanometer-scale manufacturing also require state-of-the-art fabrication techniques, and devices fabricated using such methods can have high cost.

Previous bump array (also known as "obstacle array") devices have been described, and their basic operation is explained, for example in U.S. Pat. No. 7,150,812, which is incorporated herein by reference in its entirety. Referring to FIGS. 3 and 4 of U.S. Pat. No. 7,150,812, a bump array operates essentially by segregating particles passing through an array (generally, a periodically-ordered array) of obstacles, with segregation occurring between particles that follow an "array direction" that is offset from the direction of bulk fluid flow or from the direction of an applied field.

Figure 8:
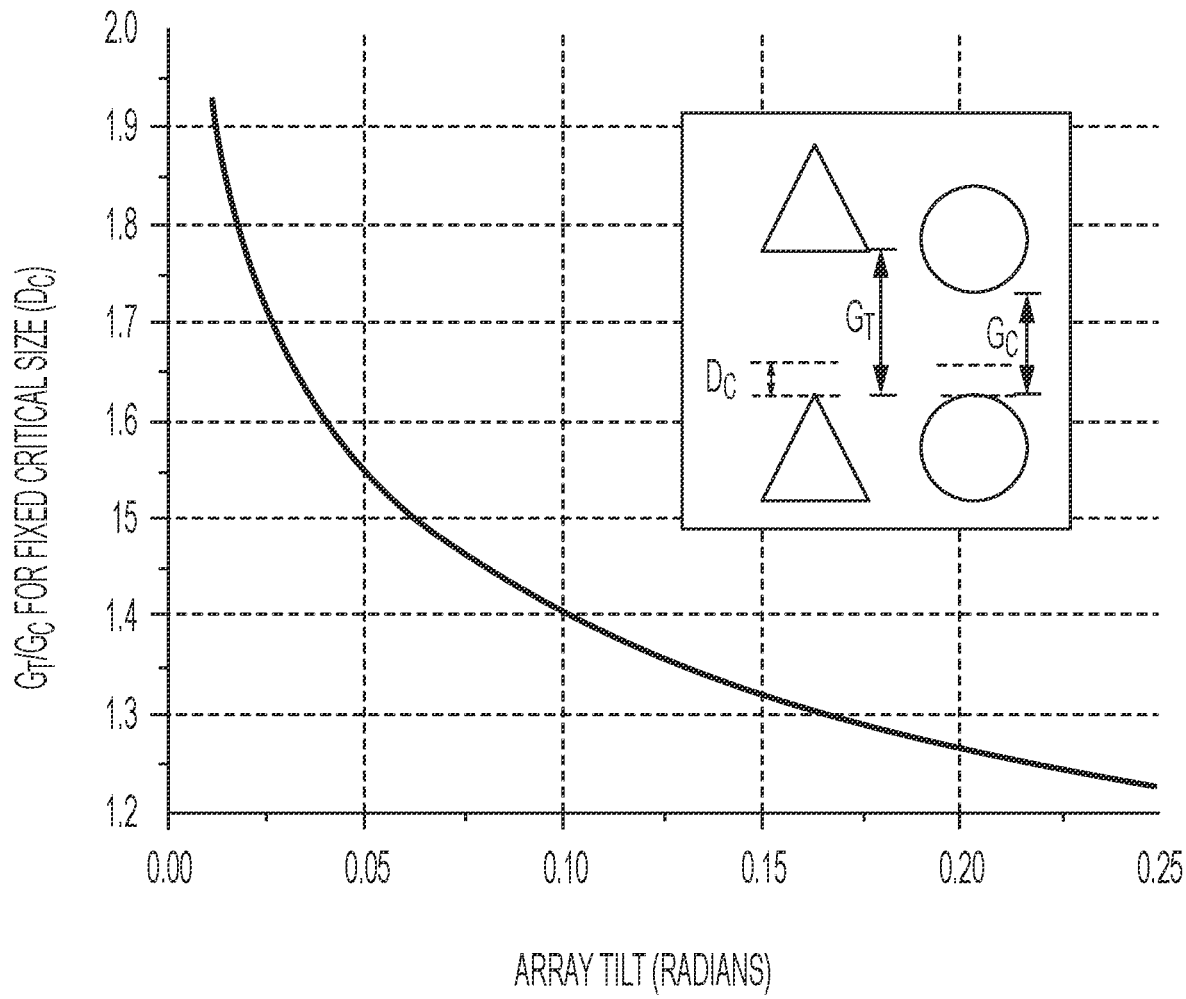
FIG. 8 is a graph illustrating the effect of the tilt angle ("Array Tilt" in FIG. 8) on gap length G. $G_T$ refers to the gap length between triangular posts, and $G_C$ refers to the gap length between round posts.

At the level of flow between two adjacent obstacles under conditions of relatively low Reynold's number, fluid flow generally occurs in a laminar fashion. Considering the volumetric flow between two obstacles in hypothetical layers (e.g., modeling the flow by considering multiple adjacent stream tubes of equal volumetric flow between the obstacles, as shown in FIG. 8 of U.S. Pat. No. 7,150,812), the likelihood that fluid in a layer will pass on one side or the other of the next (i.e., downstream) obstacle is calculable by standard methods (see, e.g., Inglis et al., 2006, Lab Chip 6:655-658). For an ordered array of obstacles offset from the direction of bulk fluid flow, the arrangement of the obstacles will define an array direction corresponding to the direction in which the majority of fluid layers between two obstacles travels. A minority of fluid layers will travel around the downstream obstacle in a direction other than the array direction.

The path that a particle passing between the two obstacles will take depends the flow of the fluid in the layers occupied by the particle. Conceptually, for a particle having a size equal to one of the hypothetical fluid layers described in the preceding paragraph, the particle will follow the path of the fluid layer in which it occurs, unless it diffuses to a different layer. For particles larger than a single fluid layer, the particle will take the path corresponding to the majority of the fluid layers acting upon it. Particles having a size greater than twice the sum of the thicknesses of the minority of layers that travel around a downstream obstacle in the direction other than the array direction will necessarily be acted upon by more fluid layers moving in the array direction, meaning that such particles will travel in the array direction. This concept is also illustrated in FIGS. 5-11 of U.S. Pat. No. 7,150,812. Thus, there is a "critical size" for particles passing between two obstacles in such an array, such that particles having a size greater to that critical size will travel in the array direction, rather than in the direction of bulk fluid flow and particles having a size less than the critical size will travel in the direction of bulk fluid flow. Particles having a size precisely equal to the critical size have an equal chance of flowing in either of the two directions. By operating such a device at a high Peclet number (i.e., such that advective particle transport by fluid layers greatly outweighs diffusive particle between layers), the effects of diffusion of particles between fluid layers can be ignored.

A method of improving the separating ability of obstacle arrays without requiring a decrease in the size of the array features or the accuracy of microfabrication techniques used to make them would be highly beneficial. The present invention relates to such methods and obstacles arrays made using such methods.

Bump Arrays

The invention relates to ways of structuring and operating obstacle arrays for separating particles. In previous obstacle arrays described by others, obstacles had shapes and were arranged such that the profile of fluid flow through gaps between adjacent obstacles was symmetrical about the center line of the gap. Viewed another way, the geometry of the adjacent obstacles in such older obstacle arrays is such that the portions of the obstacles defining the gap are symmetrical about the axis of the gap that extends in the direction of bulk fluid flow. The velocity or volumetric profile of fluid flow through such gaps is approximately parabolic across the gap, with fluid velocity and flux being zero at the surface of each obstacle defining the gap (assuming no-slip flow conditions) and reaches a maximum value at the center point of the gap. The profile being parabolic, a fluid layer of a given width adjacent to one of the obstacles defining the gap will contain an equal proportion of fluid flux as a fluid layer of the same width adjacent the other obstacle that defines the gap meaning that the critical size of particles that are 'bumped' during passage through the gap is equal regardless of which obstacle the particle travels near.

The present invention relates, in part, to the discovery that the particle size-segregating performance of an obstacle array can be improved by shaping and disposing the obstacles such that the portions of adjacent obstacles that deflect fluid flow into a gap between obstacles are not symmetrical about the axis of the gap that extends in the direction of bulk fluid flow. Such lack of flow symmetry into the gap leads to a non-symmetrical fluid flow profile within the gap. Concentration of fluid flow toward one side of a gap (i.e., a consequence of the non-symmetrical fluid flow profile through the gap) reduces the critical size of particles that are induced to travel in the array direction, rather than in the direction of bulk fluid flow. This is so because the non-symmetry of the flow profile causes differences between the width of the flow layer adjacent to one obstacle that contains a selected proportion of fluid flux through the gap and the width of the flow layer that contains the same proportion of fluid flux and that is adjacent the other obstacle that defines the gap. The different widths of the fluid layers adjacent the obstacles defining a gap that exhibits two different critical particle sizes. A particle traversing the gap will be bumped (i.e., travel in the array direction, rather than the bulk fluid flow direction) if it exceeds the critical size of the fluid layer in which it is carried. Thus, it is possible for a particle traversing a gap having a non-symmetrical flow profile to be bumped if the particle travels in the fluid layer adjacent one obstacle, but to be not-bumped if it travels in the fluid layer adjacent the other obstacle defining the gap.

Particles traversing an obstacle array pass through multiple gaps between obstacles, and have multiple opportunities to be bumped. When a particle traverses a gap having a non-symmetrical flow profile, the particle will always be bumped if the size of the particle exceeds the (different) critical sizes defined by the flow layers adjacent the two obstacles defining the gap. However, the particle will only sometimes be bumped if the size of the particle exceeds the critical size defined by the flow layer adjacent one of the two obstacles, but does not exceed the critical size defined by the flow layer adjacent the other obstacle. Particles that do not exceed the critical size defined by the flow layer adjacent either of the obstacles will not be bumped. There are at least two implications that follow from this observation.

Figure 1:
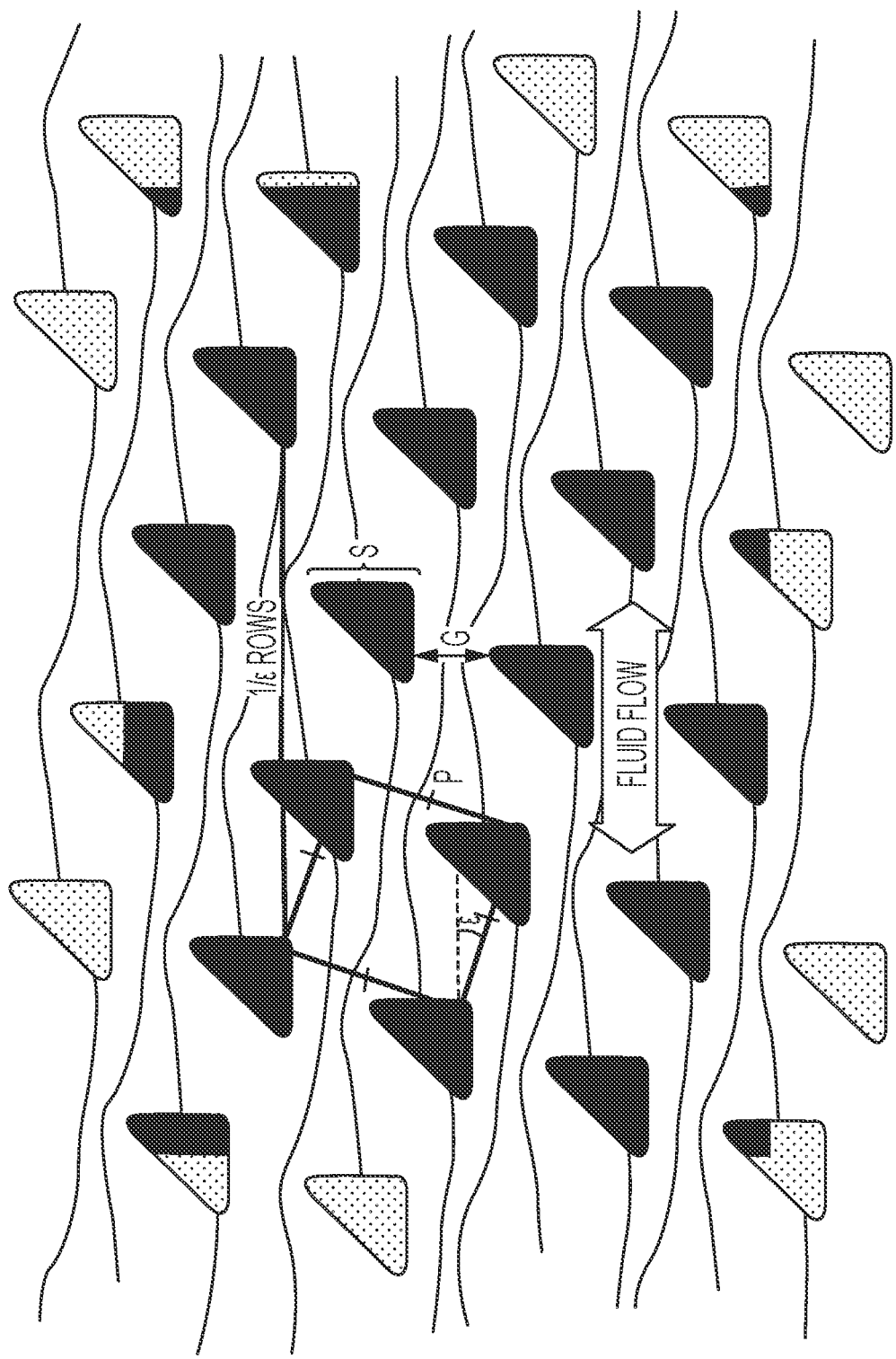
FIG. 1 is a schematic diagram of cross-section of a "bump array" device having right triangularly-shaped obstacles disposed in a microfluidic channel. In the figure, fluid flow alternates between the right-to-left and left-to-right directions, as indicated by the double-headed arrow marked, "Fluid Flow." In this array, right triangular posts are disposed in a square lattice arrangement that is tilted with respect directions of fluid flow. The tilt angle (epsilon) is chosen so the device is periodic. In this embodiment, a tilt angle of 18.4 degrees (⅓ radian) makes the device periodic after three rows. The gap between posts is denoted G with triangle side length S and array pitch P. Streamlines are shown extending between the posts, dividing the fluid flow between the posts into three regions ("stream tubes") of equal volumetric flow.

First, in an obstacle array in which the obstacles define gaps having a non-symmetrical flow profile, particles having a size that exceeds the smaller of the two critical sizes defined by the flow layers adjacent the obstacles will be separated from particles having a size smaller than that smaller critical size Significantly, this means that the critical size defined by a gap can be decreased by altering the symmetry of flow through the gap without necessarily decreasing the size of the gap ("G" in FIG. 1). This is important in that decreasing gap size can significantly increase the cost and difficulty of producing the array. Conversely, for a given critical size, the size of the gap defining that critical size can be increased by altering the symmetry of flow through the gap. Because smaller gaps are more likely to clog than larger ones, this is significant for improving the operability of the arrays, allowing greater throughput and lower likelihood of clogging.

Second, in an obstacle array in which the obstacles define gaps having a non-symmetrical flow profile, particles can be separated into three populations: i) particles having a size smaller than either of the critical sizes defined by the flow layers adjacent the obstacles; ii) particles having a size intermediate between the two critical sizes defined by the flow layers adjacent the obstacles; and iii) particles having a size larger than either of the critical sizes defined by the flow layers adjacent the obstacles.

In another aspect of the invention, it has been discovered that decreasing the roundness of edges of obstacles that define gaps can improve the particle size-segregating performance of an obstacle array. By way of example, arrays of obstacles having a triangular cross-section with sharp vertices exhibit a lower critical particle size than do arrays of identically-sized and -spaced triangular obstacles having rounded vertices.

Thus, by sharpening the edges of obstacles defining gaps in an obstacle array, the critical size of particles deflected in the array direction under the influence of bulk fluid flow can be decreased without necessarily reducing the size of the obstacles. Conversely, obstacles having sharper edges can be spaced farther apart than, but still yield particle segregation properties equivalent to, identically-sized obstacles having less sharp edges.

In yet another aspect of the invention, it has been discovered that shaping the obstacles in an obstacle array in such a way that the geometry of the obstacles encountered by fluid flowing through the array in one direction differs (and defines a different critical particle size) from the geometry of the obstacles encountered by fluid flowing through the array in a second direction. For example, fluid flowing through the array illustrated in FIG. 1 in a left-to-right direction encounters and flows around the rounded vertices of the right triangular posts of the array (in this flow direction, the profile of fluid flow through the gaps is asymmetric about the axis of the gaps). However, fluid flowing through the same array in a right-to-left direction encounters and flows around the flat edges of the right triangular posts of the array (in this flow direction, the profile of fluid flow through the gaps is symmetric about the axis of the gaps, being essentially parabolic).

Bump Arrays Having Gaps with Asymmetrical Flow Profiles

This disclosure relates to bump array devices that are useful for segregating particles by size. In one embodiment, the device includes a body defining a microfluidic flow channel for containing fluid flow. An array of obstacles is disposed within the flow channel, such that fluid flowing through the channel flows around the obstacles. The obstacles extend across the flow channel, generally being either fixed to, integral with, or abutting the surface of the flow channel at each end of the obstacle.

The obstacles are arranged in rows and columns, in such a configuration that the rows define an array direction that differs from the direction of fluid flow in the flow channel by a tilt angle (E) that has a magnitude greater than zero. The maximum operable value of ϵ is ⅓ radian. The value of ϵ is preferably ⅕ radian or less, and a value of ¹⁄₁₀ radian has been found to be suitable in various embodiments of the arrays described herein. The obstacles that are in columns define gaps between themselves, and fluid flowing through the flow channel is able to pass between these gaps, in a direction that is generally transverse with respect to the columns (i.e., generally perpendicular to the long axis of the obstacles in the column and generally perpendicular to a plane extending through the obstacles in the column).

The obstacles have shapes so that the surfaces (upstream of, downstream of, or bridging the gap, relative to the direction of bulk fluid flow) of two obstacles defining a gap are asymmetrically oriented about the plane that extends through the center of the gap and that is parallel to the direction of bulk fluid flow through the channel That is, portions of the two obstacles cause asssymetric fluid flow through the gap. The result is that the velocity profile of fluid flow through the gap is asymmetrically oriented about the plane. As a result of this, the critical particle size for particles passing through the gap adjacent to one of the obstacles is different than the critical particle size for particles passing through the gap adjacent to the other of the obstacles.

The materials and number of pieces from which the body is constructed is immaterial. The body can be made from any of the materials from which micro- and nano-scale fluid handling devices are typically fabricated, including silicon, glasses, plastics, and hybrid materials. For ease of fabrication, the flow channel can be constructed using two or more pieces which, when assembled, form a closed cavity (preferably one having orifices for adding or withdrawing fluids) having the obstacles disposed within it. The obstacles can be fabricated on one or more pieces that are assembled to form the flow channel, or they can be fabricated in the form of an insert that is sandwiched between two or more pieces that define the boundaries of the flow channel Materials and methods for fabricating such devices are known in the art.

In order to facilitate modeling and predictable operation of the bump array devices described herein, the flow channel is preferably formed between two parallel, substantially planar surfaces, with the obstacles formed in one of the two surfaces (e.g., by etching the surface to remove material that originally surrounded the non-etched portions that remain as obstacles). The obstacles preferably have a substantially constant cross-section along their length, it being recognized that techniques used to fabricate the obstacles can limit the uniformity of the cross section.

The obstacles are solid bodies that extend across the flow channel, preferably from one face of the flow channel to an opposite face of the flow channel Where an obstacle is integral with (or an extension of) one of the faces of the flow channel at one end of the obstacle, the other end of the obstacle is preferably sealed to or pressed against the opposite face of the flow channel A small space (preferably too small to accommodate any of particles of interest for an intended use) is tolerable between one end of an obstacle and a face of the flow channel, provided the space does not adversely affect the structural stability of the obstacle or the relevant flow properties of the device. In some embodiments described herein, obstacles are defined by a cross-sectional shape (e.g., round or triangular). Methods of imparting a shape to an obstacle formed from a monolithic material are well known (e.g., photolithography and various micromachining techniques) and substantially any such techniques may be used to fabricate the obstacles described herein. The sizes of the gaps, obstacles, and other features of the arrays described herein depend on the identity and size of the particles to be handled and separated in the device, as described elsewhere herein. Typical dimensions are on the order of micrometers or hundreds of nanometers, but larger and smaller dimensions are possible, subject to the limitations of fabrication techniques.

As described herein, certain advantages can be realized by forming obstacles having sharp (i.e., non-rounded) edges, especially at the narrowest part of a gap between two obstacles. In order to take advantage of the benefits of sharp edges, a skilled artisan will recognize that certain microfabrication techniques are preferable to others for forming such edges. Sharpness of edges can be described in any of a number of ways. By way of example, the radius of curvature of an edge (e.g., the vertex of a triangular post) can be measured or estimated and that radius can be compared with a characteristic dimension of the obstacle (e.g., the shorter side adjacent the vertex of a triangular, square, or rectangular post, or the radius of a round post having a pointed section). Sharpness can be described, for example, as a ratio of the radius of curvature to the characteristic dimension. Using equilateral triangular posts as an example, suitable ratios include those not greater than 0.25, and preverably not greater than 0.2.

The number of obstacles that occur in an array is not critical, but the obstacles should be sufficiently numerous that the particle-separating properties of the arrays that are described herein can be realized. Similarly, other than as described herein, the precise layout and shape of the array is not critical. In view of the disclosures described herein, a skilled artisan in this field is able to design the layout and number of obstacles necessary to make bump arrays capable of separating particles, taking into account the sizes and identities of particles to be separated, the volume of fluid in which the particles to be separated are contained, the strength and rigidity of the materials used to fabricate the array, the pressure capacity of fluid handling devices to be used with the array, and other ordinary design features.

As discussed herein, the shape and spacing of obstacles are important design parameters for the arrays. The obstacles are generally organized into rows and columns (use of the terms rows and columns does not mean or imply that the rows and columns are perpendicular to one another). Obstacles that are generally aligned in a direction transverse to fluid flow in the flow channel are referred to as obstacles in a column. Obstacles adjacent to one another in a column define a gap through which fluid flows. Typically, obstacles in adjacent columns are offset from one another by a degree characterized by a tilt angle, designated $\epsilon$ (epsilon). Thus, for several columns adjacent one another (i.e., several columns of obstacles that are passed consecutively by fluid flow in a single direction generally transverse to the columns), corresponding obstacles in the columns are offset from one another such that the corresponding obstacles form a row of obstacles that extends at the angle $\epsilon$ relative to the direction of fluid flow past the columns. The tilt angle can be selected and the columns can be spaced apart from each other such that $1/\epsilon$ (when $\epsilon$ is expressed in radians) is an integer, and the columns of obstacles repeat periodically. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of $\epsilon$.

The shape of the individual obstacles is important, and it has been discovered that improved bump array function can be achieved by shaping one or more portions of two obstacles that define a gap in such a way that the portions of the obstacles that are upstream from, downstream from, or briding (or some combination of these, with reference to the direction of bulk fluid flow through the flow channel) the narrowest portion of the gap between the obstacles are asymmetrical about the plane that bisects the gap and is parallel to the direction of bulk fluid flow. Both for simplicity of fabrication and to aid modeling of array behavior, all obstacles in an array are preferably identical in size and shape, although this need not be the case. Furthermore, arrays having portions in which obstacles are identical to one another within a single portion, but different than obstacles in other portions can be made.

Without being bound by any particular theory of operation, it is believed that asymmetry in one or more portions of one or both of the obstacles defining a gap leads to increased fluid flow on one side or the other of the gap. A particle is bumped upon passage through a gap only if the particle exceeds the critical particle size corresponding to the gap. The critical particle size is determined by the density of fluid flux near the boundaries of the gap (i.e., the edges of the obstacles that define the gap). Increased fluid flow on one side of a gap (i.e., against one of the two obstacles defining the narrowest portion of the gap) intensifies flux density near that side, reducing the size of the particle that will be bumped upon passage through that side of the gap.

In one embodiment of the device, the shape of each of multiple obstacles in a column is substantially identical and symmetrical about the plane that bisects each of the multiple obstacles. That is, for any one column of obstacles, the geometry encountered by particles traveling in fluid flowing through the gaps between the obstacles in the column is identical when the fluid is traveling in a first direction and when the fluid is travelling in a second direction that is separated from the first direction by 180 degrees (i.e., flow in the opposite direction).

In another important embodiment, the geometry encountered by particles traveling in fluid flowing through the gaps between the obstacles in the column is different when the fluid is traveling in a first direction than the geometry encountered when the fluid is travelling in a second direction that is different from the first direction by 90-180 degrees. In this embodiment, fluid flow can, for example, be oscillated between the two flow directions, and the particles in the fluid will encounter the different obstacle geometry. If these geometrical differences result in different fluid profiles through the gaps (compare the panels in FIG. 6B, for example), then the gap can exhibit different critical particle sizes in the two directions. If a gap exhibits different critical sizes for flow in the two directions, then the populations of particles that will be bumped upon passing through the gap will differ depending on the direction of flow. This difference in the populations bumped in the two directions can be used to effect segregation of the differently-acting particles.

For example, consider a gap that exhibits a first critical size for bulk fluid flow in one direction, but exhibits a different critical size for bulk fluid flow in a second direction. For fluid flow in the first direction, particles having a size greater than the first critical size will be bumped, and particles having a size less than the first critical size will not be bumped. Similarly, for fluid flow in the second direction, particles having a size greater than the second critical size will be bumped, and particles having a size less than the second critical size will not be bumped. If flow is oscillated between the first and second directions, then particles having a size larger than both the first and the second critical sizes will be bumped in both directions. Similarly, particles having a size smaller than both the first and the second critical sizes will not be bumped in either direction. For these two populations of particles, flow oscillations of approximately equal quantities in both directions will leave these particles substantially at their initial position. However, particles having a size intermediate between the two critical sizes will be bumped when bulk fluid flow is in one direction, but will not be bumped when bulk fluid flow is in the other direction. Thus, when flow oscillations of approximately equal quantities in both directions are performed, these particles will not be left in their initial position, but will instead have been displaced from that original position by an amount equal to (the size of an obstacle+the gap distance G)×the number of oscillations. In this way, these particles (the ones having a size intermediate between the two critical sizes) can be segregated from the other particles with which they were initially intermixed.

In the special case of when the first and second directions differ by 180 degrees (i.e., the flows are in opposite directions, the particles having a size intermediate between the two critical sizes will be displace at an angle of 90 degrees relative to the direction of oscillating flow.

The behavior of particles in a bump array is not a function of the absolute direction in which the particles (or the fluid in which they are suspended) move, but rather is a function of the array geometry that the particles encounter. As an alternative to operating a bump array with alternating flow between first and second directions, the same particle-displacing effects can be obtained using flow only in the first direction by increasing the size of the array by two times the number of oscillations, maintaining one portion of the array in its original arrangement, but altering the second portion of the array such that the geometry of the array is identical to the geometry encountered by particles in fluid moving in the second direction in the original array (even though the fluid moves in the first direction only. Using the array illustrated in FIG. 1 by way of example, the same displacement effects on particles can be obtained by two oscillations of flow in this array (i.e., two units of flow left-to-right and two units of flow right-to-left) as can be obtained by four units of left-to-right flow through an array having four times the (left-to-right) length of the array in FIG. 1, so long as two lengths of the array are arranged as shown in FIG. 1 and two lengths of the array are arranged as the mirror image (left-to-right) of the array shown in FIG. 1.

The invention relates to a microfluidic device designed to separate objects on the basis of physical size. The objects can be cells, biomolecules, inorganic beads, or other objects of round or other shape. Typical sizes fractionated to date range from 100 nanometers to 50 micrometers, although smaller or larger sizes are possible. Prior work with these arrays involved continuous flows in one direction, and particles are separated from the flow direction by an angle which is a monotonic function of their size.

This invention is a modification on bump array design that adds functionality. By changing the shape of the posts from circles to a shape that is asymmetric about an axis parallel to the fluid flow, two new functionalities may be added:

1. The critical particle size for bumping may be different depending on which direction a particle moves through the array. This has been experimentally verified with right triangular posts, and extends to arbitrary shapes that are asymmetric about the flow axis.

2. With such designs, the angle of displacement from the fluid flow of particles may be designed not to be monotonic—e.g. peaked at a certain particle size.

Such bump arrays have multiple uses, including all of the uses for which bump arrays were previously known.

The device can be used to separate particles in a selected size band out of a mixture by deterministic lateral displacement. The mechanism for separation is the same as the bump array, but it works under oscillatory flow (AC conditions; i.e., bulk fluid flow alternating between two directions) rather than continuous flow (DC conditions; i.e., bulk fluid flow in only a single direction). Under oscillatory flow, particles of a given size range can be separated perpendicularly from an input stream (perpendicular to the alternating flow axis when the alternating flows differ in direction by 180 degrees) without any net displacement of the bulk fluid or net displacement of particles outside the desired range. Thus, by injecting a sample including particles of the given range into an obstacle array and thereafter alternating fluid flow through the obstacle array in opposite directions (i.e., in directions separated from one another by 180 degrees), particles that are exceed the critical size in one flow direction but do not exceed the critical size in the other flow direction can be separated from other particles in the sample by the bumping induced by the array. Such particles are bumped (and follow the array direction) when fluid flows in one direction, but are not bumped (and follow the bulk fluid flow direction) when fluid flows in the opposite direction. Particles that do not exceed the critical size in either flow direction will not be bumped by the array (will follow the bulk fluid in both directions), and will remain with the sample bolus. Particles that exceed the critical size in both flow directions will be bumped by the array (will follow the array direction) when fluid flows in one direction, and are also bumped (will follow the array direction in the opposite direction) when fluid flows in the opposite direction, and will therefore remain with the sample bolus.

That is, in devices of this sort, critical particle size depends on direction of fluid flow. Intermediate sized particles can be made to ratchet up a device under oscillatory flow.

Second, in a continuous flow mode, particles of a desired size can be induced to move to one side of a fluid stream, and particles above or below that size to the other side or not displaced at all. Thus collection of desired particles may be easier. In conventional devices, particles above a desired range are also displaced from the fluid flow to the same side of the flow, so separating the desired from undesired larger ones may be harder. In this embodiment, obstacles defining different critical sizes for fluid flow in opposite directions are employed in two configurations that are mirror images of one another. For example, with reference to FIG. 1, such an array would include right triangular posts arranged as shown in FIG. 1 (i.e., hypotenuse sloping from lower right to upper left and the tilt angle ϵ extending from the horizontal toward the bottom of the figure) and would also include right triangular posts arranged as they would appear in a mirror held perpendicularly at the right or left side of the array shown in FIG. 1 (i.e., right triangular posts having their hypotenuse sloping from upper right to lower left and the tilt angle ϵ extending from the horizontal toward the top of the figure). Particle separation achieved by bulk fluid flow in a single direction (i.e., either from left-to-right or right-to-left) through such an array would be equivalent to back-and-forth flow through the array illustrated in FIG. 1. Particles in the selected size range would be bumped toward the top of the array (as shown in FIG. 1), while particles having larger or smaller sizes would remain at the vertical level at which they enter the array (assuming approximately equal numbers of obstacles in each of the two configurations are encountered).

We have also discovered that reduction in critical particle size as a ratio of gap, compared to circular posts, occurs when particles bump off sharp edges. This allows larger separation angle without fear of clogging the device faster separations.

These developments potentially reduces the necessary chip area compared to a continuous flow bump array.

Device is a microfabricated post array constructed using standard photolithography. A single mask layer is etched into silicon or used to make a template for PDMS molding. Post arrays are usually sealed with a PDMS coated cover slip to provide closed channels The new methods may require more careful control of the post shape than a conventional device.

Oscillatory flow operation may require more complicated fluid control drivers and interfaces than continuous flow operation.

Both aspects of the invention have been experimentally verified in bump array with right triangular posts.

Figure 11:
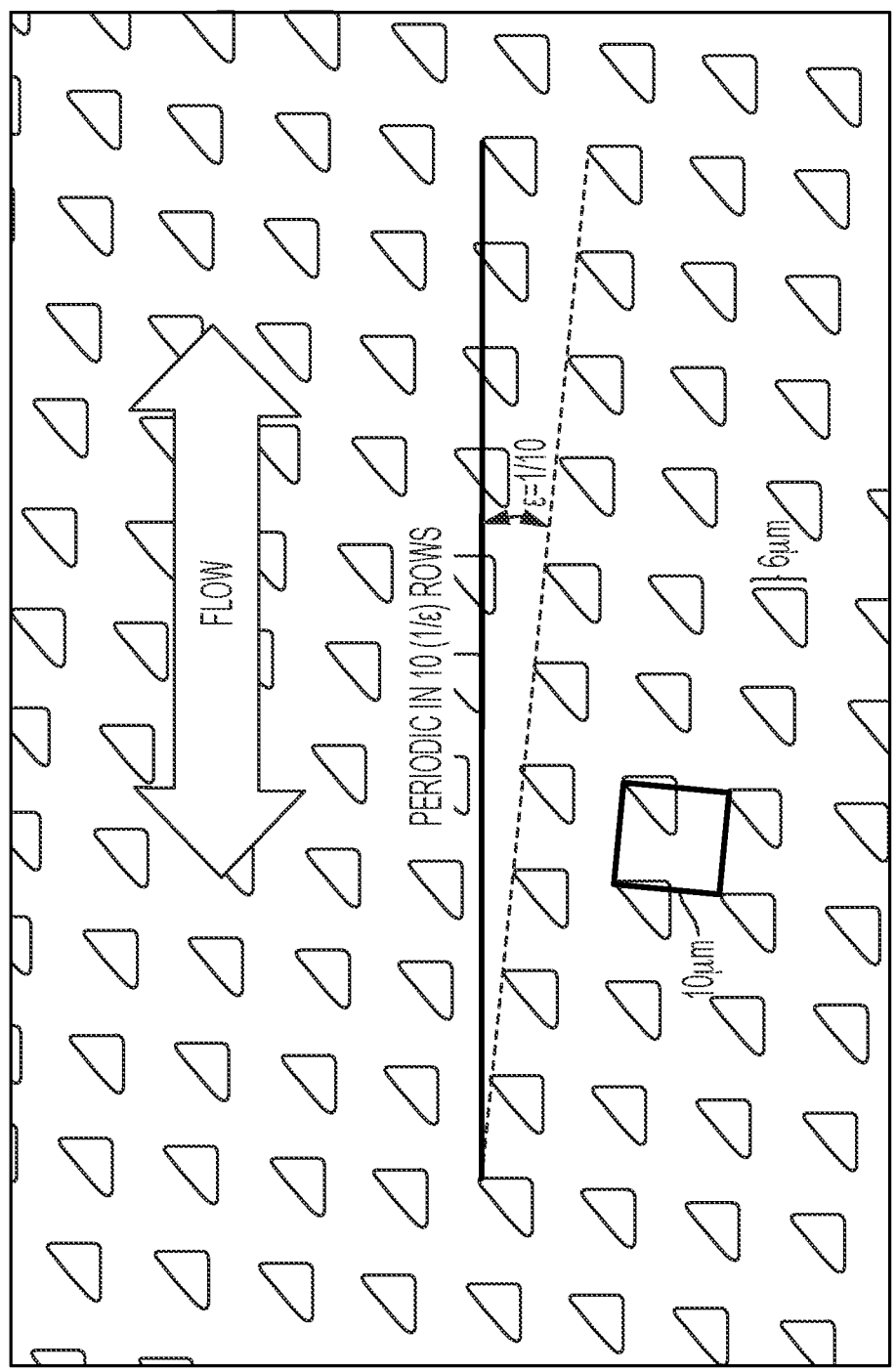
FIG. 11 is an image of an array constructed as described herein.

FIG. 11 is a scanning electron microscope image of posts in an obstacle array of the type described herein. Right isosceles triangular posts, 6 microns on a side, were placed on a square lattice with spacing of 10 microns, giving a gap of approximately 4 microns. The square lattice was tilted 5.71 degrees (0.1 radians) with respect to the device sidewalls to provide necessary asymmetry. Fluid flows along the horizontal axis.

In FIG. 1, the total fluid flux through each gap can be divided into n=1/ε' flow streams (stream tubes), where n is a whole number. Each flow stream carries equal fluid flux, shown schematically in FIG. 1 for n=3. The stream tubes are separated by stall lines, each stall line beginning and ending on a post. The stream tubes shift their positions cyclically so that after n rows each streamline returns to its initial position within the gap.

The width of the stream closest a post determines the critical particle size. If the particle's radius is smaller than the width of the stream, then the particle's trajectory is undisturbed by the posts and travels in the same direction of the flow. If the particle's radius is larger than the width of the closest stream, then it is displaced across the stall line and it's trajectory follows the tilted axis of the array (i.e., the array direction).

The width of the stream closest to the post can be determined by assuming that the velocity profile through a gap is parabolic—the case for fully-developed flow in a rectangular channel Since each stream carries equal flux and there are n streams, we can integrate over the flow profile such that the flux through a stream of width Dc/2 (Dc is the critical diameter of a particle) closest to the post is equal to the total flux through the gap divided by n. That is, the integral from 0 to Dc/2 of u(x) dx (u being a function of flux at any position x within the gap) being equal to 1/n times the integral of u(x) dx over the entire gap.

Thus, the critical particle size can be determined from the flow profile. For the case of circular posts, a parabolic flow profile closely approximates the flow profile through the gap and the critical particle size can be determined analytically.

Figure 4A:
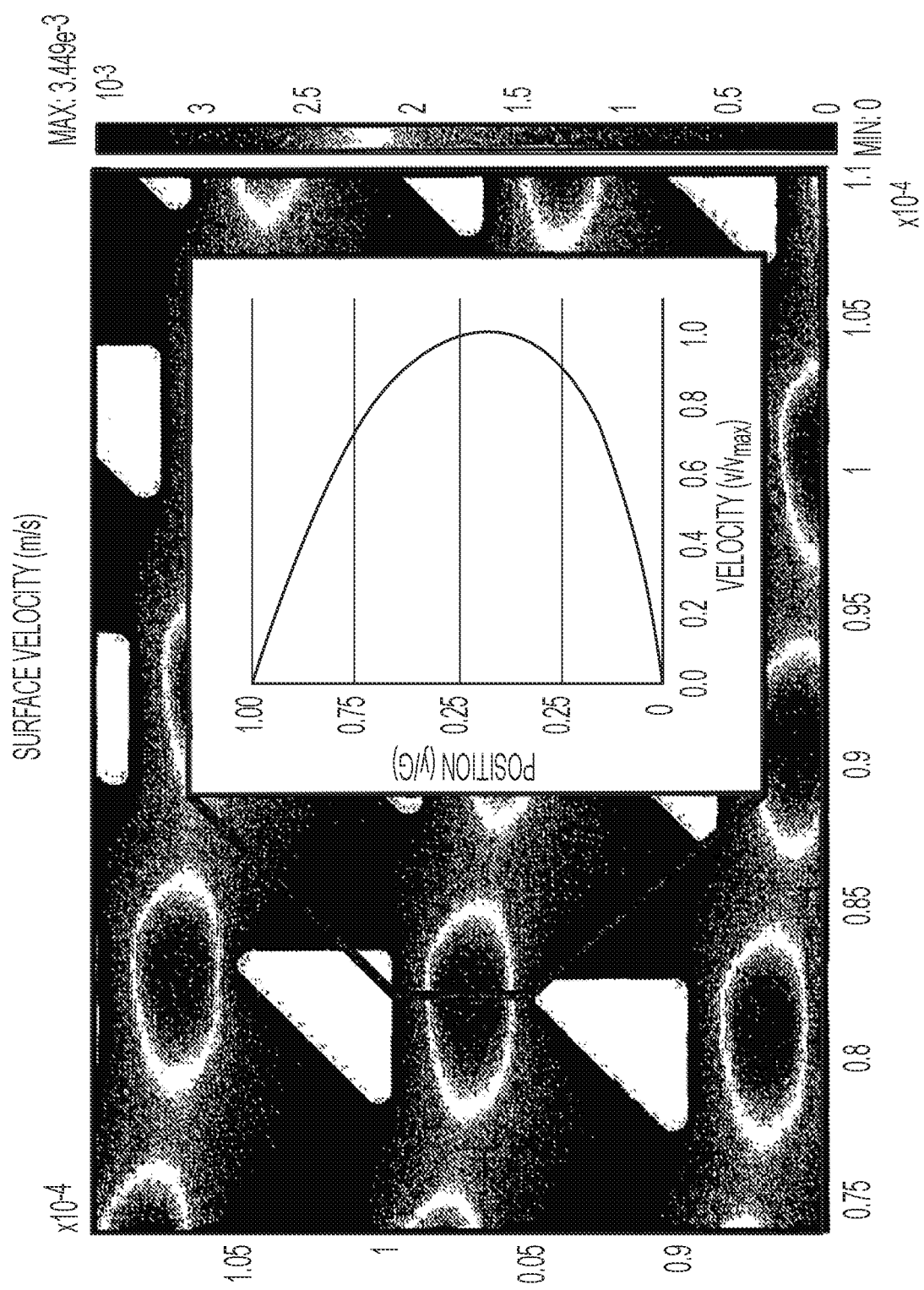
FIG. 4A is a graph showing simulated normalized velocity flow between two right triangular posts.

FIG. 4A shows a numerical simulation of flow profile for an array of triangular posts. We cannot assume that flow profile through triangular posts is parabolic because of the broken symmetry. Therefore, flow profile through gap of triangular posts was extracted from numerical simulation (program—COMSOL) of flow through an array with same size and spacing as devices actually made.

Figure 4B:
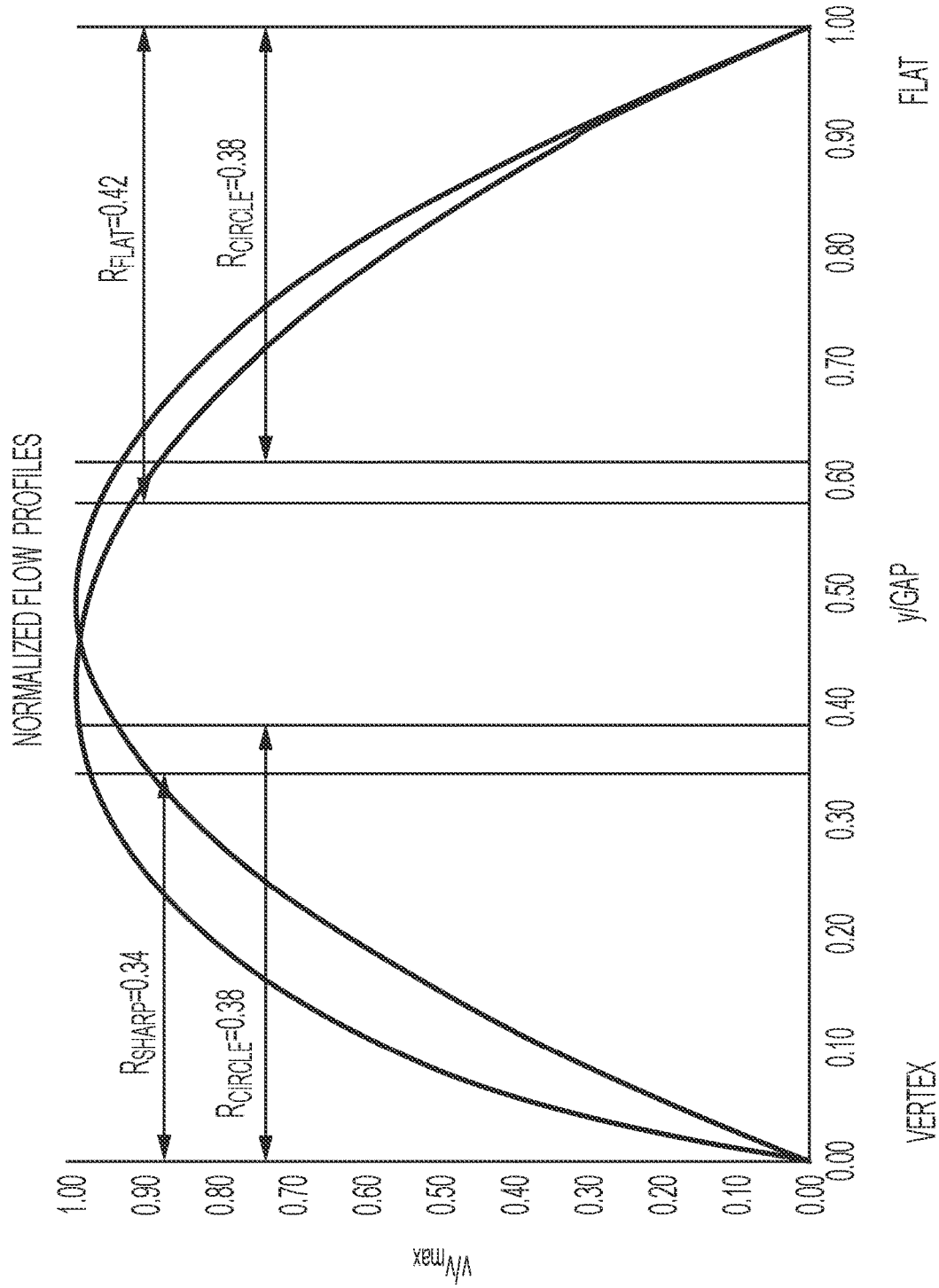
FIG. 4B is a graph showing normalized velocity profiles through gaps between round obstacles (curve that is symmetrical about Y/Gap=0.5) and right triangularly-shaped obstacles in an array of the type shown in FIG. 1 (ϵ=⅓ radian). In these profiles, vertical lines delineate the areas under each curve into thirds, representing three stream tubes of equal volumetric flow. The curve for the round obstacles demonstrates that one third of the volumetric flow between round obstacles occurs in a stream tube that is adjacent to either obstacle and has a width that is 38% of the gap width. The curve for the triangular obstacles demonstrates that one third of the volumetric flow between triangular occurs in a stream tube that is adjacent to the flat side of one of the two triangular obstacles and has a width that is 42% of the gap width and that an additional one third occurs in a stream tube that is adjacent the sharp side of the pair of triangular obstacles and has a width that is 34% of the gap width.

FIG. 4B illustrates a comparison of velocity flow profiles between circular and triangular posts. Normalized velocity profiles through gap for triangular and circular posts are shown. As shown, the flow profile for the triangle posts is asymmetric about the center of the gap; more fluid flows along the vertex of the triangle than along the flat edge.

Figure 12:
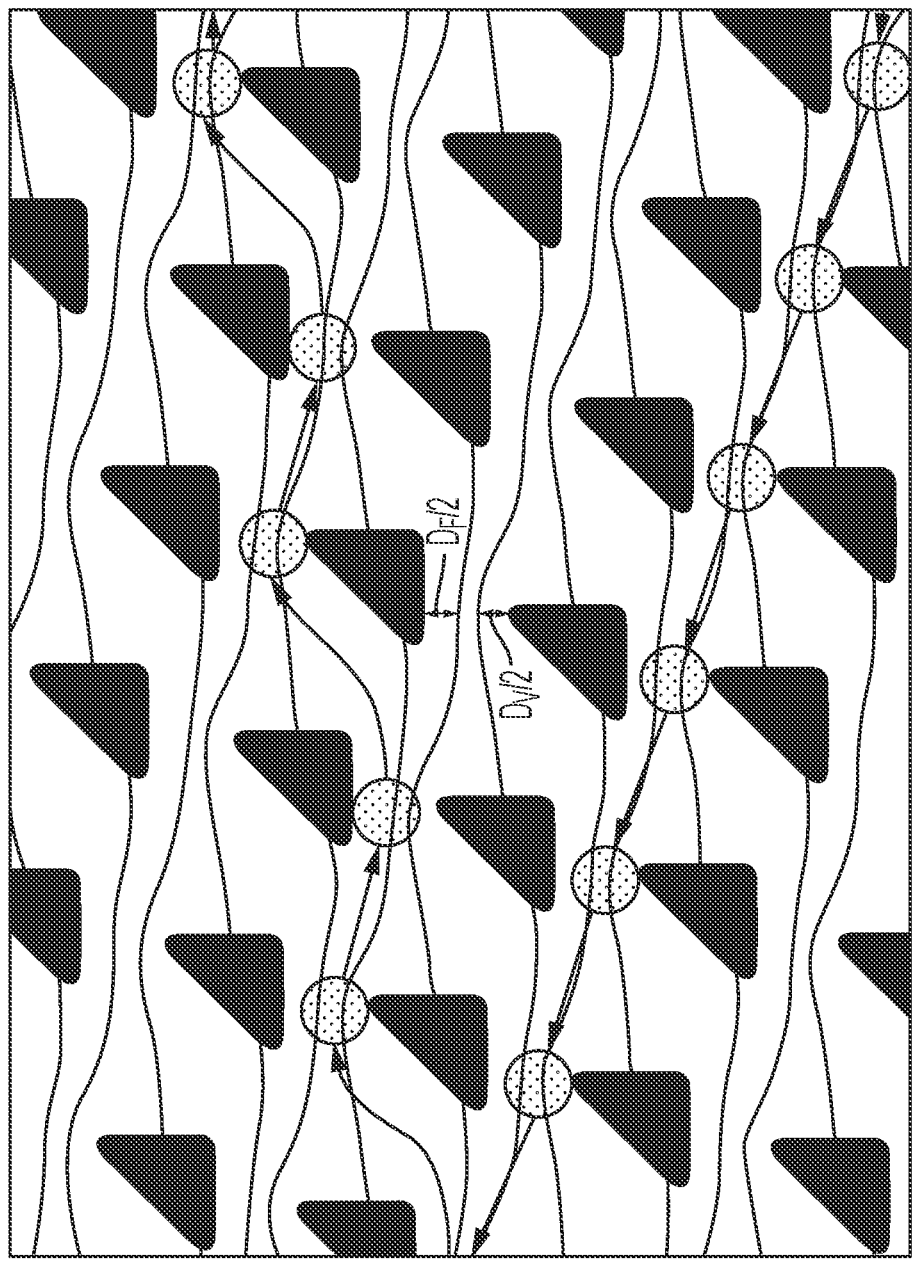
FIG. 12 illustrates particle motion in a ratchet bump array of the type described herein.
Figure 13:
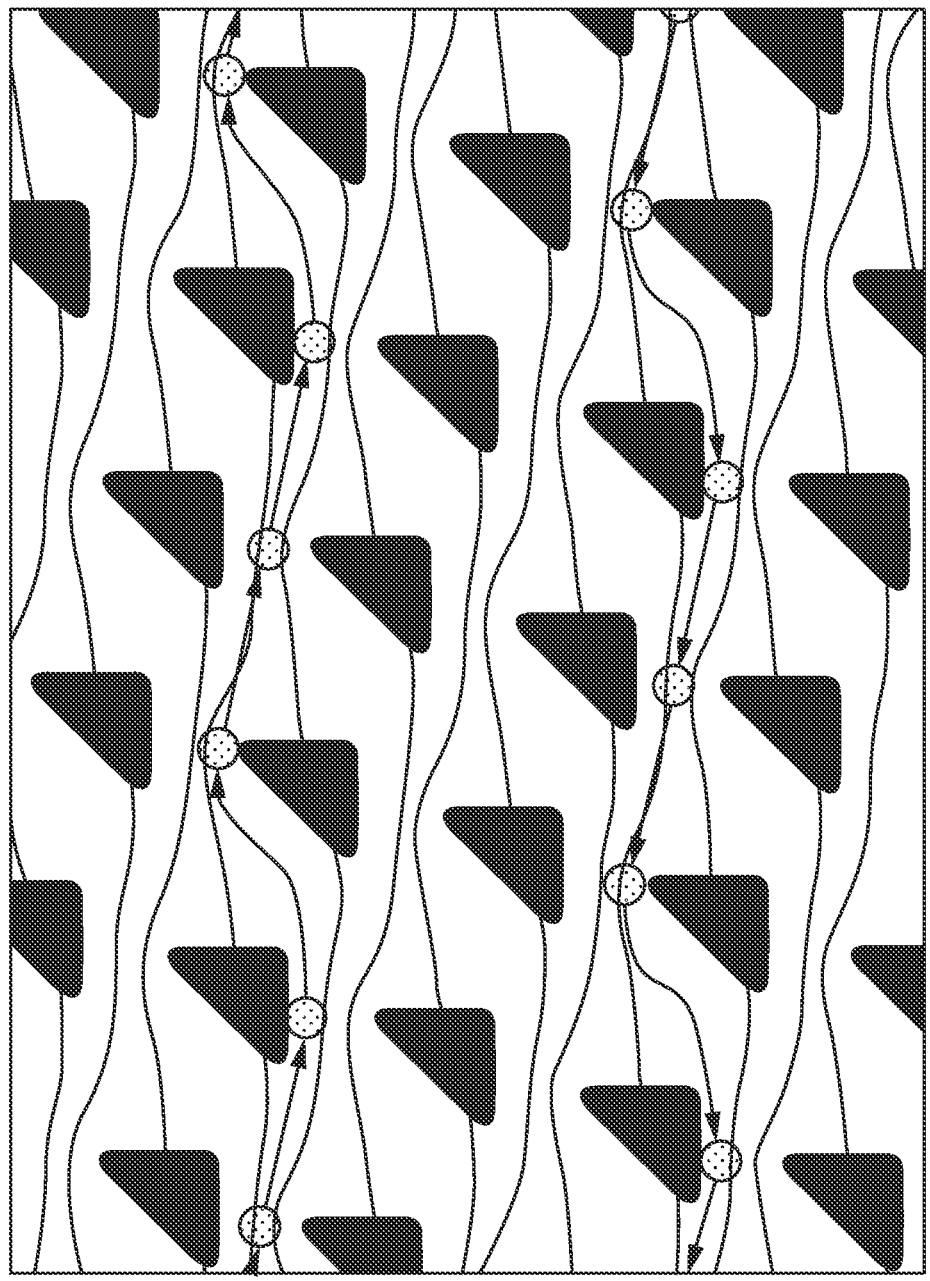
FIG. 13 illustrates particle motion in a ratchet bump array of the type described herein.
Figure 14:
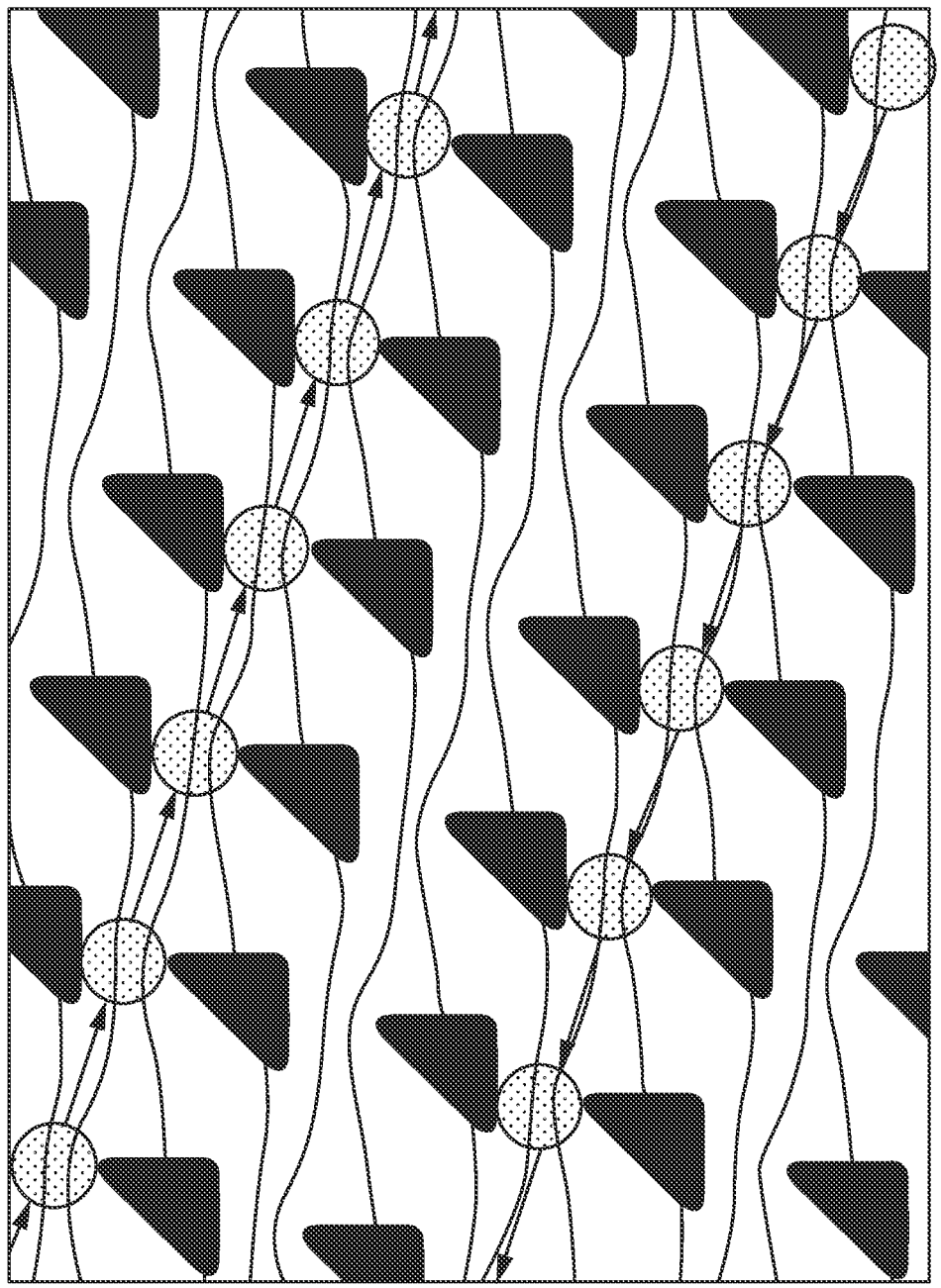
FIG. 14 illustrates particle motion in a ratchet bump array of the type described herein.

FIGS. 12-14 illustrate particle motion in a ratchet bump array of the type described herein. When particles move through the array, the side of the post they interact with depends on which direction they are moving in the array. In this case, when the particles are moving from right-to-left, they bump off the flat edge of the triangular posts. When the particles are moving from left-to-right, they bump off the sharp vertex of the triangular posts. Thus, since the flow profile is asymmetric, we cannot expect particles to follow the same trajectory when travelling in both directions through the array.

Figure 15:
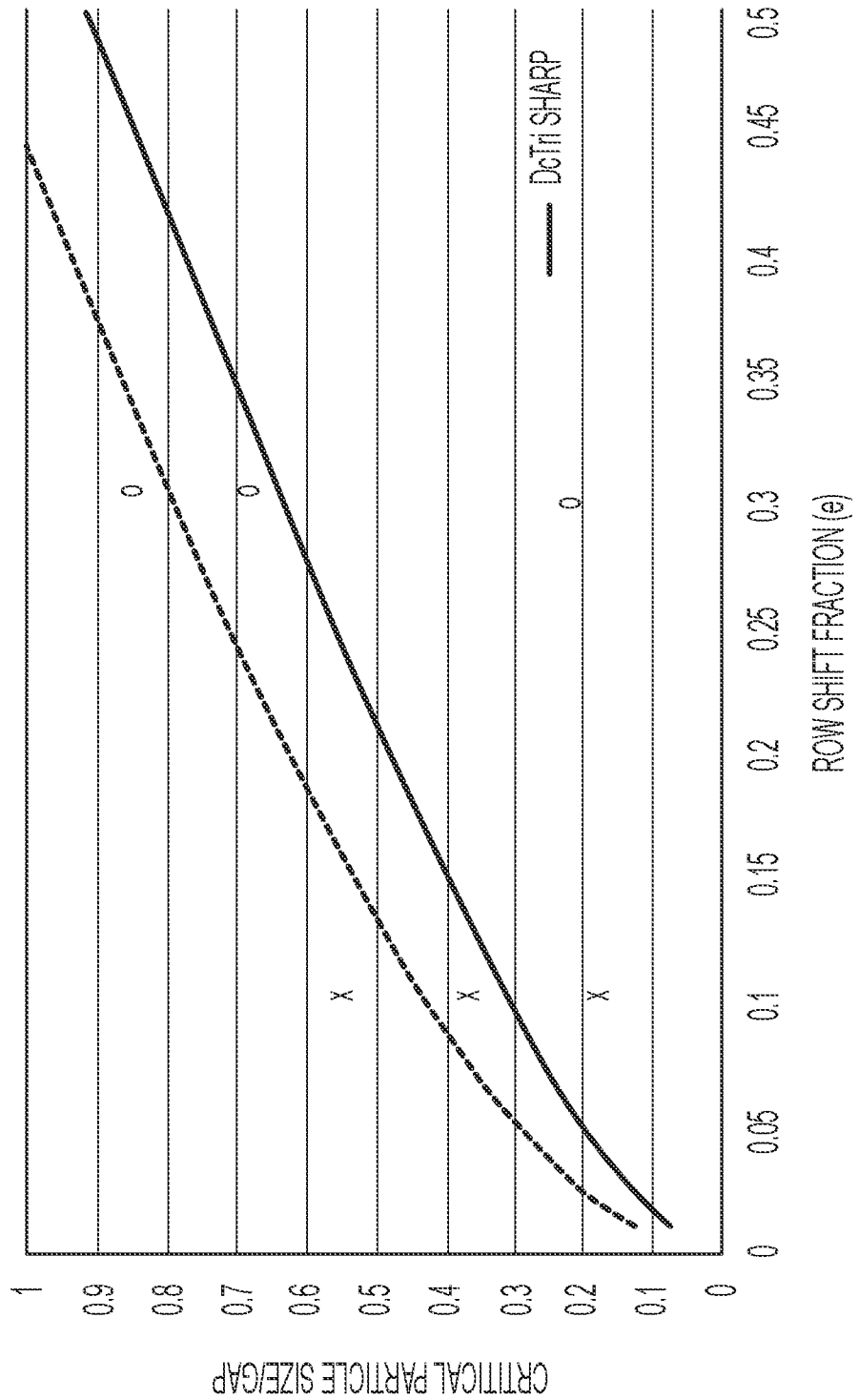
FIG. 15 is a graph comparing the critical size characteristics of round and triangular posts.

Critical Particle Size for Triangular Posts—Employing the same kind of analysis described in the Inglis et al., 2006, Lab Chip 6:655-658, we can integrate over the flow profile to find the width of characteristic streams. However, since the flow profile is asymmetric about the center of the gap, the stream width, and hence the critical particle size will be different depending on which side we examine. As shown in FIG. 4B, the result of the asymmetry introduced by the triangular posts is that the critical particle size is different depending on which side of the triangular obstacle particles interact with. If they are moving along the sharp vertex, then the critical particle size is smaller than if they are moving along the flat edge. Critical particle size vs. array angle (ε) are plotted in FIG. 15 compared to circular posts. The critical particle size for bumping along the sharp vertex of the triangle is substantially smaller than for that of circular posts or the flat edge. This allows higher angles of separation to be used without fear of clogging the devices. When the particle diameter is larger than the gap size (G in FIG. 1), there is substantial risk that the array will become clogged if particle density is high.

Figure 3A:
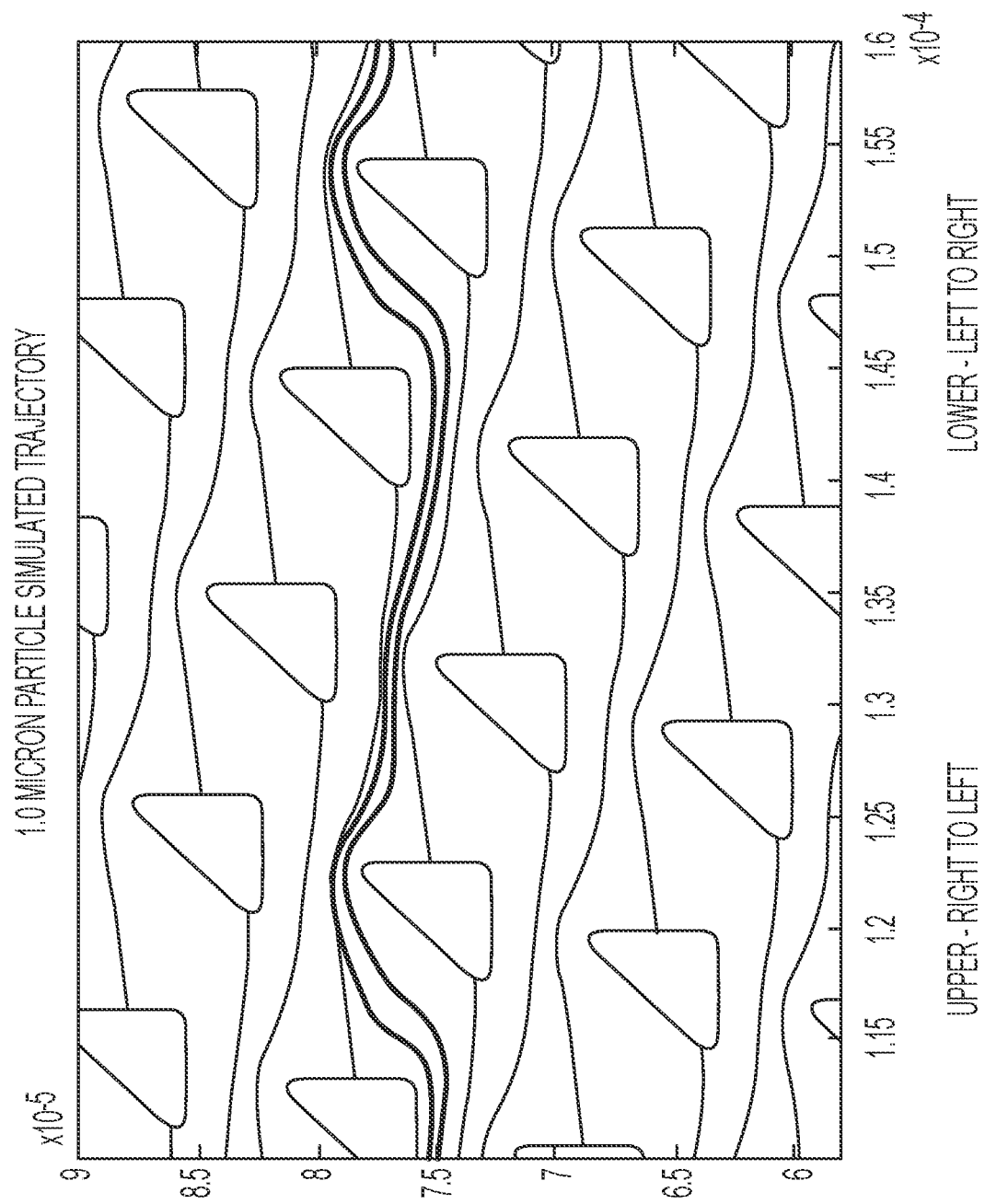
FIGS. 3A, 3B and 3C show diagrams of the simulated trajectories of particles moving through an array of right triangular posts disposed in a microfluidic flow channel in which fluid flow alternates between the right-to-left and left to-right directions.
Figure 3B:
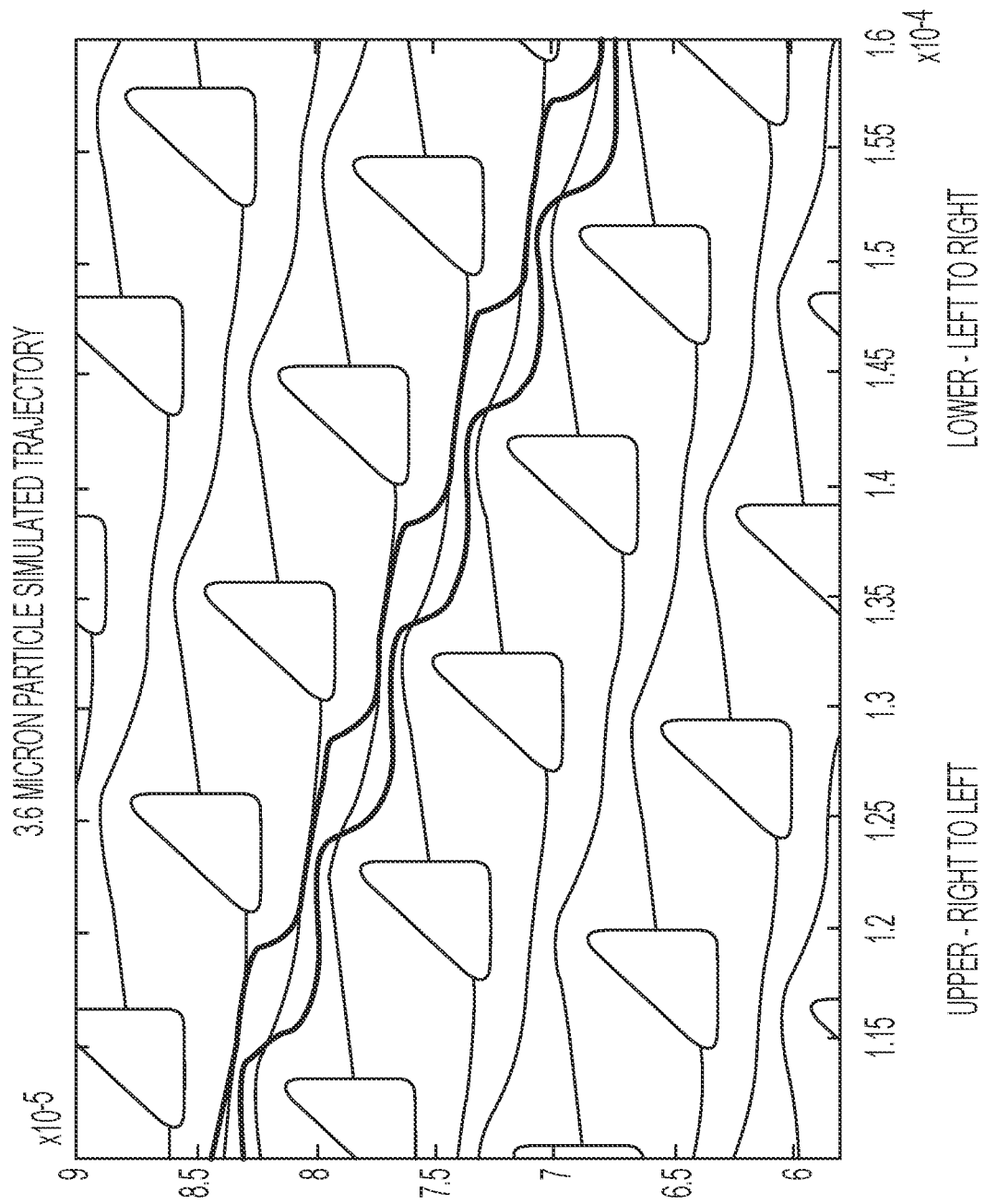
Figure 3C:
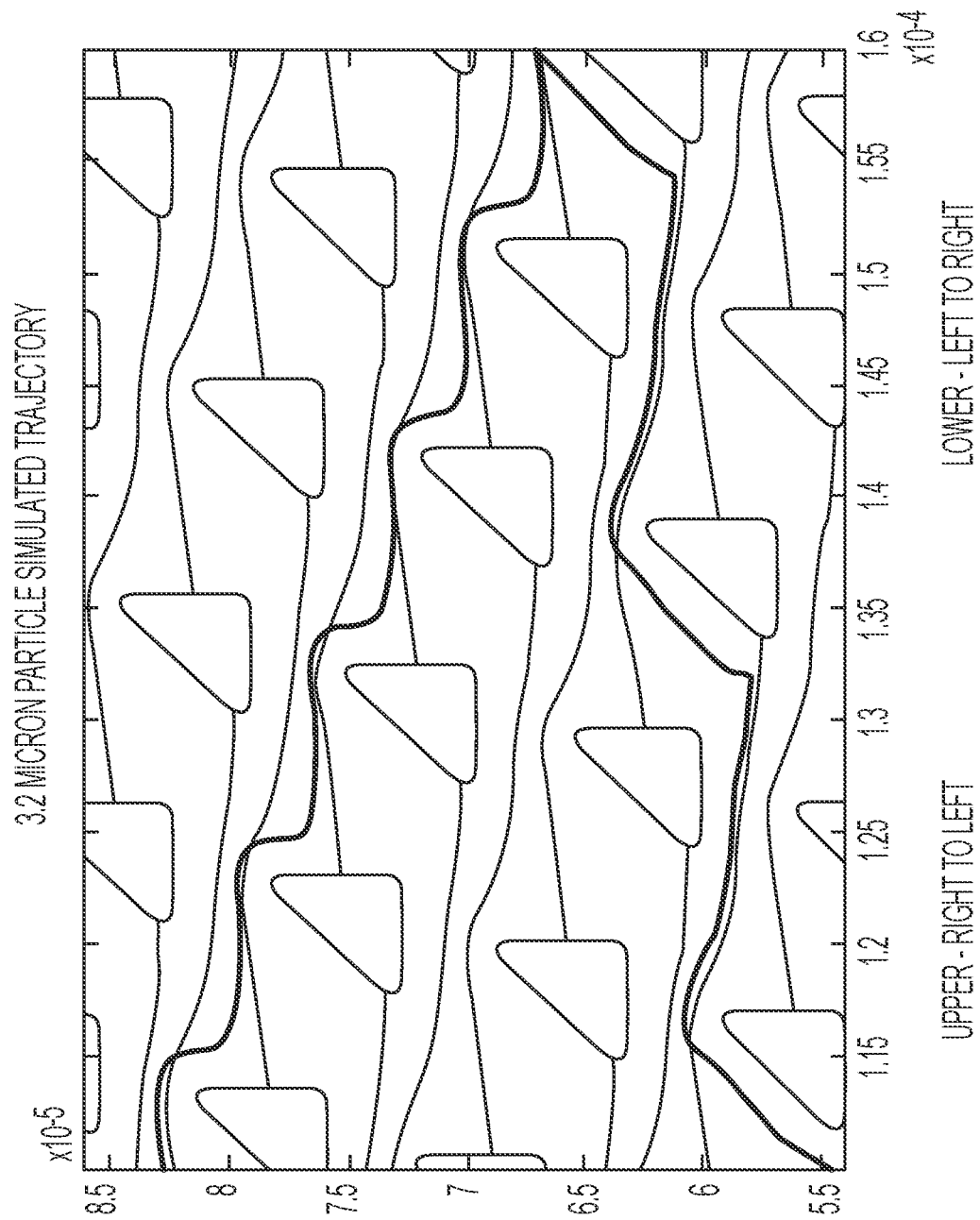

FIGS. 3A-3C illustrate representative particle behavior in a ratchet bump array. For a device constructed as shown in FIG. 11, three representative particles were chosen for this illustration. One particle (illustrated in FIG. 3B) was chosen larger than both critical particle sizes (i.e., larger than the critical particle sizes defined by right-to-left and left-to right fluid flows). One particle (illustrated in FIG. 3A) was chosen smaller than both critical particle sizes Finally, one particle (illustrated in FIG. 3C) was chosen in the intermediate range smaller than the critical particle size ($D_F$ in FIG. 12) along the flat edge, but larger than the critical particle size ($D_V$ in FIG. 12) along the sharp edge. These figures illustrate the behavior of particles that were put into the device and their trajectory under oscillatory flow was observed.

Large Particle (FIG. 3B): Since the particle is larger than the critical particle size along both edges, it follows the array tilt axis (E) in both directions and shows no net displacement under oscillatory flow.

Small Particle (FIG. 3A): Since the particle is smaller than the critical particle size along both edges, it follows the fluid trajectory in both directions and shows no net displacement.

Intermediate Particle (FIG. 3C): When the particle moves to the right, it bumps off the flat edge of the triangular posts. Since it is smaller than the critical particle size ($D_F$), it follows the fluid trajectory. When the particle moves to the left, it bumps off the sharp vertex of the triangular posts. Since it is larger than the critical particle size on this side ($D_V$), it follows the array tilt axis and is displaced upward. As shown, under oscillatory flow, particles in the intermediate range are displaced perpendicular to the direction of the flow. After three cycles of moving back and forth, the bulk fluid has not been displaced, but the particle has moved over 200 microns.

If all three particle types were mixed and placed in a single array under oscillatory flow (i.e., fluid flow oscillating between the right-to-left and left-to-right directions), the intermediate particles would be displaced toward the top of these figures while the small and large particles would have no net motion.

In FIGS. 12-14, representations of intermediate, small, and large particles (respectively) were overlaid on top of numerical simulation of stream tubes to show motion of particles more clearly. n=1/ϵ Was chosen to be 3 to allow periodicity to be more easily seen.

When intermediate particles (FIG. 12) travel along the sharp edge, they bump like expected. However, when the particles travel along the flat edge, their motion is different than that of the small particles. When they perform their characteristic zig to keep going with the direction of the fluid, they are too large to stay in that stream that is close to the sharp vertex and are displaced across the first stall line. The result is that their motion is periodic in two rows instead of three. With any other tilt angle, the motion is similar and the periodicity is n−1. The result of this n−1 periodicity is that the intermediate sized particles are actually displaced against the axis tilt angle. Thus a mixture of large, small and intermediate particles will be separated into three streams. Small particles will go straight through (see FIG. 13). Large particles will follow the array tilt axis (see FIG. 14). Intermediate particles will follow a separate path that is dependent on the post geometry.

The applications for which devices described herein are useful include the same ones described in the Huang patent (U.S. Pat. No. 7,150,812): biotechnology and other microfluidic operations involving particle separation.

Continuous-flow fractionation of small particles in a liquid based on their size in a micropost "bump array" by deterministic lateral displacement was demonstrated previously (e.g., Huang et al., 2004, Science 304:987-990). The ratchet bump array described herein possesses all the same advantages of the previous work, but adds two new functionalities:

First, the devices can be used to separate particles in a selected size band out of a mixture by deterministic lateral displacement under oscillatory flow (AC conditions) rather than continuous flow (DC conditions). Under oscillatory flow, particles of a given size range can be separated perpendicularly from an input stream (perpendicular to the AC flow axis) without any net displacement of the bulk fluid or particles outside the desired range.

Second, in continuous flow mode, the device exhibits trimodal behavior. Particles of a desired size range can be induced to move to one side of a fluid stream, and particles above or below that size to the other side or not displaced at all. Thus collection of these desired particles may be easier. In conventional devices, the devices were bimodal and all particles above a desired size range are displaced from the fluid flow to the same side of the flow, so separating the desired from undesired larger ones requires multiple stages whereas the ratchet bump array requires only one.

As used herein, each of the following terms has the meaning associated with it in this section.

The terms "bump array" and "obstacle array" are used synonymously herein to describe an ordered array of obstacles that are disposed in a flow channel through which a particle-bearing fluid can be passed.

A "substantially planar" surface is a surface that has been made about as flat as a surface can be made in view of the fabrication techniques used to obtain a flat surface. It is understood that no fabrication technique will yield a perfectly flat surface. So long as non-flat portions of a surface do not significantly alter the behavior of fluids and particles moving at or near the surface, the surface should be considered substantially planar.

In a bump array device, "fluid flow" and "bulk fluid flow" are used synonymously to refer to the macroscopic movement of fluid in a general direction across an obstacle array. These terms do not take into account the temporary displacements of fluid streams that are necessitated in order for fluid to move around an obstacle in order for the fluid to continue to move in the general direction.

In a bump array device, the tilt angle ϵ is the angle between the direction of bulk fluid flow and the direction defined by alignment of rows of sequential (in the direction of bulk fluid flow) obstacles in the array. This angle is illustrated in FIGS. 1, 6, and 11, for example.

In a bump array device, the "array direction" is a direction defined by the defined by alignment of rows of sequential (in the direction of bulk fluid flow) obstacles in the array.

A "critical size" of particles passing through an obstacle array is a parameter that describes the size limit of particles that are able to follow the laminar flow of fluid nearest one side of a gap through which the particles are travelling when flow of that fluid diverges from the majority of fluid flow through the gap. Particles larger than the critical size will be 'bumped' from the flow path of the fluid nearest that side of the gap into the flow path of the majority of the fluid flowing through the gap. In a bump array device, such a particle will be displace by the distance of (the size of one obstacle+the size of the gap between obstacles) upon passing through the gap and encountering the downstream column of obstacles, while particles having sizes lower than the critical size will not necessarily be so displaced Significantly, when the profile of fluid flow through a gap is symmetrical about the plane that bisects the gap in the direction of bulk fluid flow, the critical size will be identical for both sides of the gap; however when the profile is asymmetrical, the critical sizes of the two sides of the gap can differ. When assessing a non-spherical particle, its size can be considered to be the spherical exclusion volume swept out by rotation of the particle about a center of gravity in a fluid, at least for particles moving rapidly in solution. Of course, the size characteristics of non-spherical particles can be determined empirically using a variety of known methods, and such determinations can be used in selecting or designing appropriate obstacle arrays for use as described herein. Calculation, measurement, and estimation of exclusion volumes for particles of all sorts are well known.

A particle is "bumped" in a bump array if, upon passing through a gap and encountering a downstream obstacle, the particle's overall trajectory follows the array direction of the bump array (i.e., travels at the tilt angle ϵ relative to bulk fluid flow). A particle is not bumped if its overall trajectory follows the direction of bulk fluid flow under those circumstances. Conceptually, if flow through a gap is visualized as being composed of multiple individual layers of fluid (i.e., stream tubes, if thought of in a cross-section of fluid flowing through the gap), a particle is "bumped" if the particle is displaced by a post out of its incident flow tube into an adjacent flow tube as it traverses a gap bounded by the post.

"The direction of bulk fluid flow" in an obstacle array device refers to the average (e.g., macroscopic) direction of fluid flow through the device (i.e., ignoring local flow deviations necessitated by flow around obstacles in the fluid channel)

A Deterministic Microfluidic Ratchet

This example describes a microfluidic device in which the trajectory of particles within a certain size range varies with the direction the particles move through the device. This ratcheting effect is produced by employing triangular rather than the conventional circular posts in a deterministic lateral displacement device where an array of posts selectively displaces particles as they move through the array. This effect is then used to demonstrate a fractionation technique where particles can be separated from a fluid plug without any net motion of the original fluid plug. The underlying mechanism of this method is based on an asymmetric fluid velocity distribution through the gap between posts.

Microfluidic devices, such as those used in "lab on a chip" applications, typically operate at low Reynolds number ("low" Reynolds number refers to Reynolds number not greater than 1, and preferably smaller, such as 0.1, $10^{-3}$, or smaller). In this regime, the fluid flow through an arbitrary geometry can be considered to be time-invariant reversing the applied pressure gradient that drives the fluid will reverse the flow field because inertial effects are negligible. At high Peclet number ("high" Peclet number refers to Peclet number greater than 1, and preferably much greater, such as 10, 100, or more), this can be extended to say that diffusive effects can be ignored and objects in the fluid will deterministically flow along a stream tube unless some other interaction, such as displacement by steric repulsion from a channel wall, disrupts their path and moves them to an adjacent stream tube. The degree to which the particle trajectory is shifted from its original path depends directly on its size; larger particles will be displaced farther than smaller particles and will consequently follow different stream tubes as they progress through the device. This phenomenon, which we call deterministic lateral displacement, has been used in several schemes to perform microscale particle separations.

The "bump array" is a microfluidic device that relies on deterministic lateral displacement to separate particles with high resolution. This device relies on asymmetric bifurcation of fluid streams in a post array that is tilted at an angle ϵ (epsilon; typically on the order of 0.1 radians) with respect to the direction of the overall fluid flow. The fluid flowing through a gap splits around a post in the next row, with 1/ϵ of the fluid going through the gap on one side of the next post, while the other ϵ of fluid goes around the other side of the next post. As a result, the fluid motion can be characterized by 1/ϵ streams that cycle through positions in the gap, but travel straight on average. If a particle suspended in the fluid is small compared to the width of a stream in a gap, the posts will not affect it as it moves through the array and it will travel straight with the fluid flow. However, if the particle is large relative to the width of a stream, it will be displaced into an adjacent stream when the stream it occupies is nearest a post as it moves through a gap. Because of the cyclical way the streams move through gaps, this displacement or "bump" will occur at every row and the particle will travel at an angle with respect to the fluid and other small particles. With a sufficiently long device, significant separation can be obtained between large and small particles.

Figures 2A, 2B, 2C:
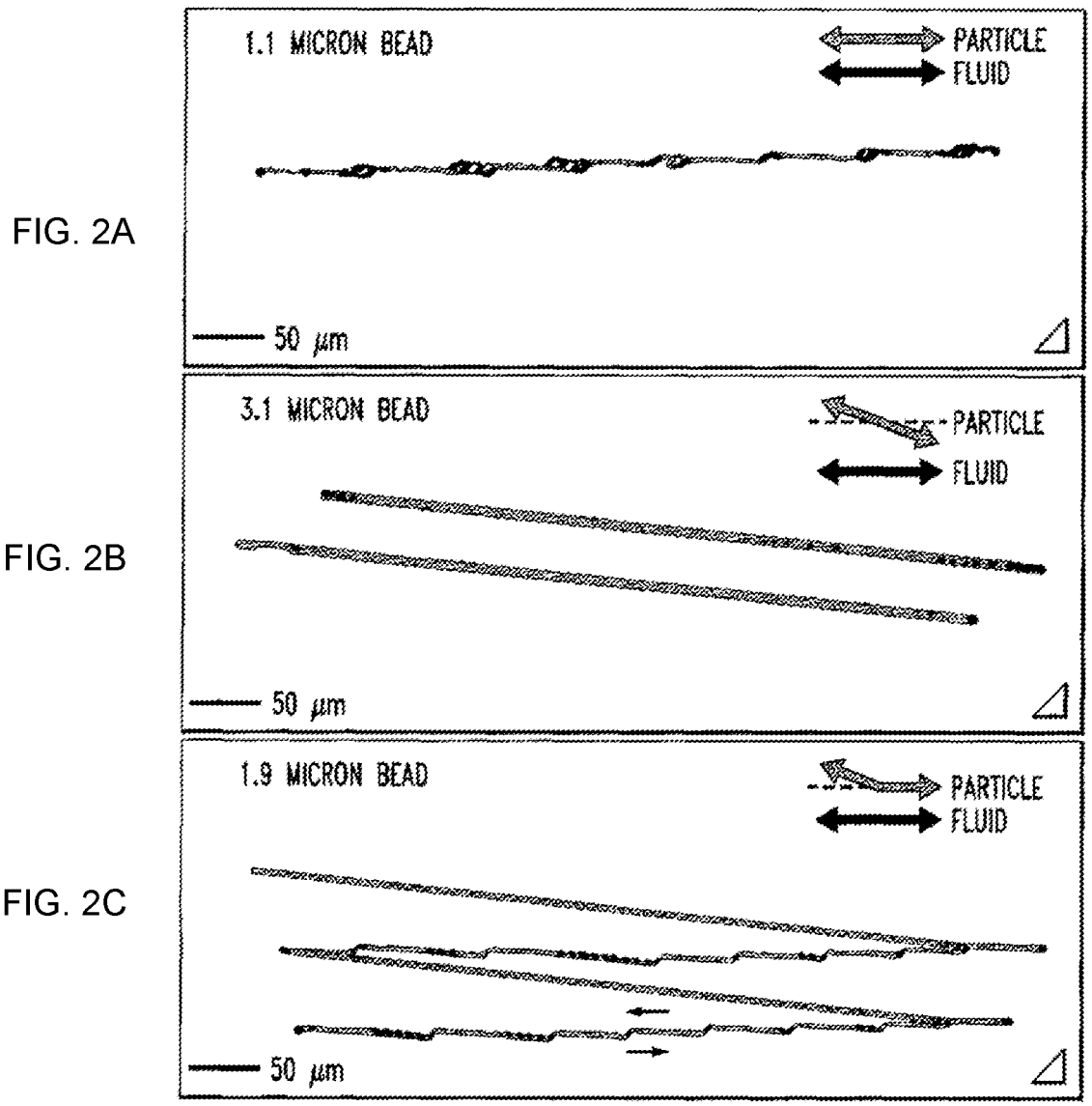
FIGS. 2A, 2B, and 2C show the trajectories of spherical polystyrene beads of three different sizes in an array of the type shown in FIG. 1 as the direction of fluid flow is cycled back and forth twice. The orientation of the right triangular posts is denoted in the lower right of each figure. Right isosceles triangles are 6 microns on a side with post to post separation of 10 microns and a tilt angle of 5.71 degrees (0.1 radian). Particle sizes are 1.1 microns in FIG. 2A, 3.1 microns in FIG. 2B, and 1.9 microns in FIG. 2C. Particles shown in FIGS. 2A and 2B retrace their paths when the direction of the fluid is switched, with the particles in FIG. 2A generally following the fluid direction in each fluid flow direction and the particles in FIG. 2B generally following the array direction in each fluid flow direction. By contrast, the trajectory of the particles shown in FIG. 2C varies with the direction of the fluid flow.

FIG. 2A shows a time fluorescent time-lapse image of a small particle (1.1 micron diameter polystyrene bead) flowing through such an array at a typical speed of 100 microns/sec. As the particle moves forward, it takes many small steps parallel to the array axis as it moves through, followed by one larger step perpendicular to the motion of the fluid (in what we refer to as "zig-zag mode"), so that the overall motion is to follow the plug of fluid which originally contained the particle. In taking the image of FIG. 2A, the fluid flow was cycled back and forth (by reversing the pressure) twice. The particle retraced its path, as expected from flows at low Reynolds and high Peclet number in a deterministic device not relying on diffusion.

FIG. 2B shows a similar image but for a larger particle (3.1 microns). In this case the particle clearly follows the array axis (i.e., travels in the array direction) and not the fluid flow. Because the particle is displaced from its flow path by the posts in each row, we refer to this as "bumping mode." This difference in flow direction as a function particle size has been exploited to make fractionation devices for both polystyrene beads as well as biological particles. As in FIG. 2A, the time lapse image shows the path of the particle over two cycles of flowing forward and back, and again the path of the particles is reversible (i.e., the particles end up where they began).

FIG. 2C shows the same experiment in the same array for a particle of intermediate size (1.9 microns). The results are very different than those shown if FIGS. 2A and 2B. This particle "zig-zags" when going to the right (i.e., moving from left-to-right) to follow the fluid flow but "bumps" when going to the left to follow the post array axis. Its path is not reversed when the fluid flow direction is reversed, with the net result that such particles are separated from a plug of fluid in a perpendicular direction when the fluid is subjected to an oscillatory flow.

The displacement of a particle off of a post is an inherently irreversible interaction, but particle trajectories in a circular post bump array are ostensibly reversible because of symmetry. There is no controversy in this statement for small particles which follow the fluid because the fluid flow must be reversible in the low Reynolds number regime (typical Re 10e-3 for fluid velocity 100 microns/sec and length scale 10 microns). However, large particles do not follow the fluid; instead, they are displaced off posts by steric repulsion so even though the fluid may reverse direction, the trajectory of particles which interact with the posts will not necessarily be reversible unless their interaction with the posts is symmetric with the direction of the fluid. In the schematic in FIG. 3A, particles moving to the left are displaced downward by the top row of posts while particles moving to the right are displaced the same amount by the bottom row of posts. However, if we rotate the image 180 degrees, which is analogous to switching the direction of the fluid, the situation is exactly switched, so the result must be the same in either direction. This rotation works because both the lattice points and post shape are invariant under 180 degree rotation. As a result, both large and small particles in bump array with a circular posts will retrace their steps if the flow is switched back and forth.

Numerical simulations showed that the velocity profile through a gap between triangular posts was shifted towards the side of the gap with the vertex. The fluid velocity profile through a gap between posts depends strongly on the local geometry at the gap. For the case of the triangular posts presented here, where there is a sharp vertex on the bottom and a flat edge on the top, a significant deviation from the parabolic flow profile used to describe pressure-driven flow through circular posts should be expected. FIG. 4A shows a numerical simulation of the fluid velocity in an array like that used to produce the particle trajectories in FIGS. 2A, 2B, and 2C, along with a cross section of the velocity profile across the gap. The line was placed across the smallest spacing between posts to corresponds with the narrowest stream widths where crossing stall lines is most likely to occur. The vertices of the triangle were rounded off with a curvature of 500 nm to approximate the rounding off of a sharp point that results from optical lithography. It was found that the flow profile was invariant under changes in the array tilt so this flow profile can be assumed to be the general flow profile for triangular posts arranged in this way.

FIG. 4B shows a comparison between the flow profiles of triangular and circular posts. For round posts, the profile is nearly parabolic as expected for Poiseuille flow through an infinitely long one-dimensional channel. For triangular posts, however, the flow profile is biased towards the sharp triangular corner pointing up into the flow stream. In other words, the streams bunch closer together near this vertex and the critical particle size for a particle to be bumped across a stall line is smaller than it would be for an array with the same gap size but with round obstacles. Along the flat edge, the opposite is true. Because the fluid travels preferentially along the vertex, the width of the stream along the flat edge is wider than for circular posts. The effect of the triangular posts is to create two separate critical particle sizes, one for moving along the vertex of the triangle and another for moving along the flat edge. Therefore, particles in between these two critical particle sizes should exhibit different behavior depending on which direction they are moving through the array. To show this, we employed the technique used by Inglis et al., 2006, Lab Chip 6:655-658 to estimate the critical particle size for circular posts by using the extracted velocity profile instead of the parabola assumed for circular posts.

Figure 5:
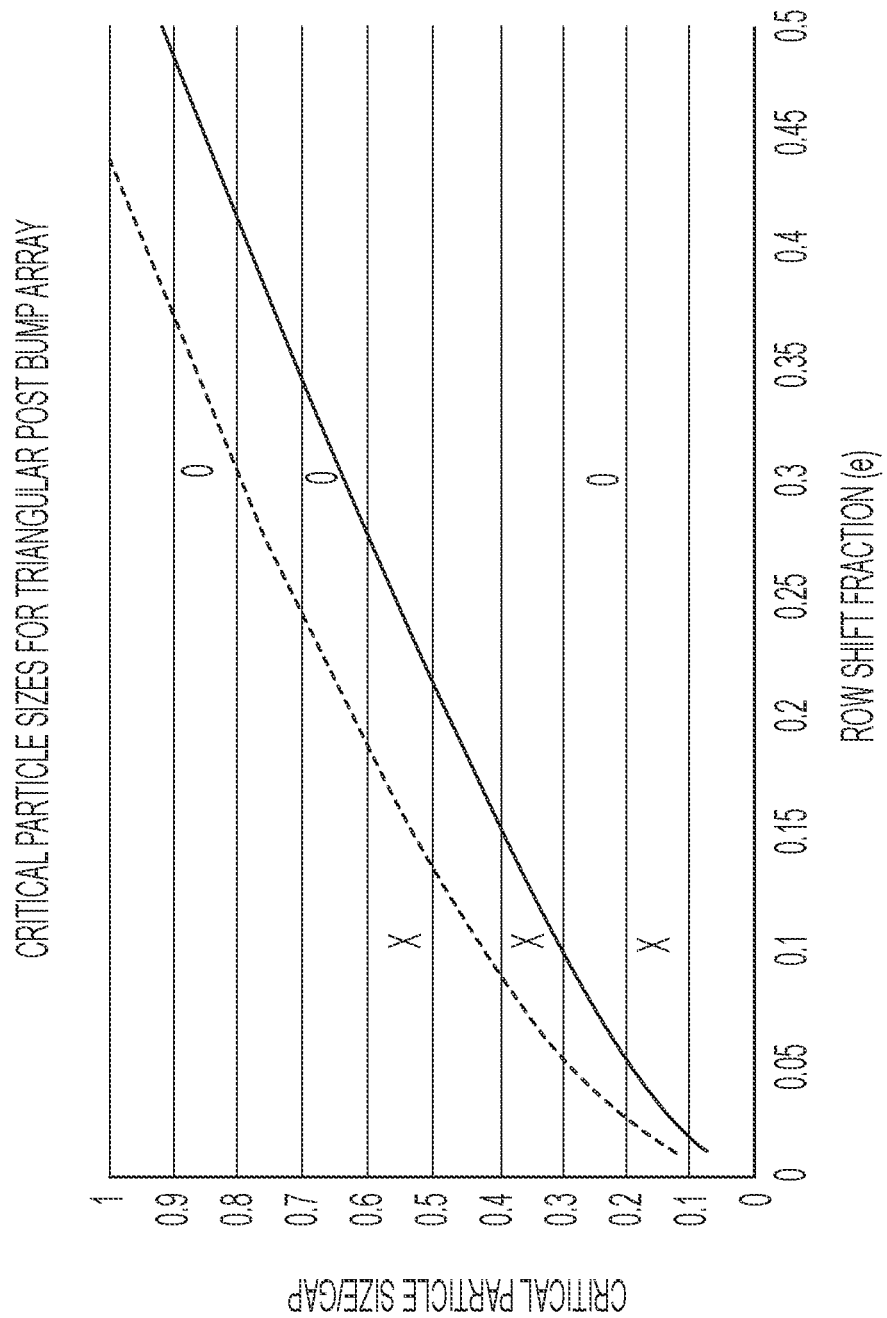
FIG. 5 is a graph of predicted critical diameter versus the array tilt angle (ϵ) for arrays of triangular (lower line) and circular (upper line) obstacles.

FIG. 5 shows this calculation of the critical particle size as a ratio of the gap for the vertex and flat of the triangle as well as for circular posts versus array tilt angle. The particles shown in figure two are shown as circles on the plot. They show good agreement with the predicted behavior. The 1.1 micron bead is smaller than both critical particle sizes so it travels with the fluid in both directions and shows no net displacement when the fluid direction is cycled. The 3.1 micron particle is bigger than both critical particle sizes so it is displaced along the array axis in both directions and shows no net displacement when the fluid direction is cycled. The 1.9 micron particle is in between the two critical particle sizes so it travels with the fluid when it moves along the flat edge of the triangle and with the array axis when it moves along the vertex of the triangle. As a result, it shows a net displacement when the fluid flow is cycled. This is characteristic of a ratcheting behavior. With no net displacement of the fluid, particles in the intermediate range of an array show a net displacement after several fluid flow oscillations. This ratchet differs from other ratchets in that the ratcheting motion does not occur along the axis of the applied force corresponding to fluid flow in either direction. Rather, it is perpendicular to the motion of the fluid.

Bump Array Employing Triangular Posts

This example describes microfluidic arrays which sort particles based on size according to the deterministic lateral displacement method, by using triangular posts instead of the usual round posts. When triangular posts are used rather than round posts, and the triangular posts are properly oriented (i.e., such that the surfaces defining the gap are asymmetric), the critical size is decreased for a given gap size between the posts. This is because the different post geometry on either side of the gap causes an asymmetric flow profile through the gap, with flux shifting towards the vertex of the triangle. This shift in fluid flux reduces the width of the stream that determines the critical particle size. In this example, both experiment and modeling are used to show that changing the post shape from circular to triangular results in several practical advantages over similar arrays with circular posts including increased dynamic range and throughput.

Figure 6A:
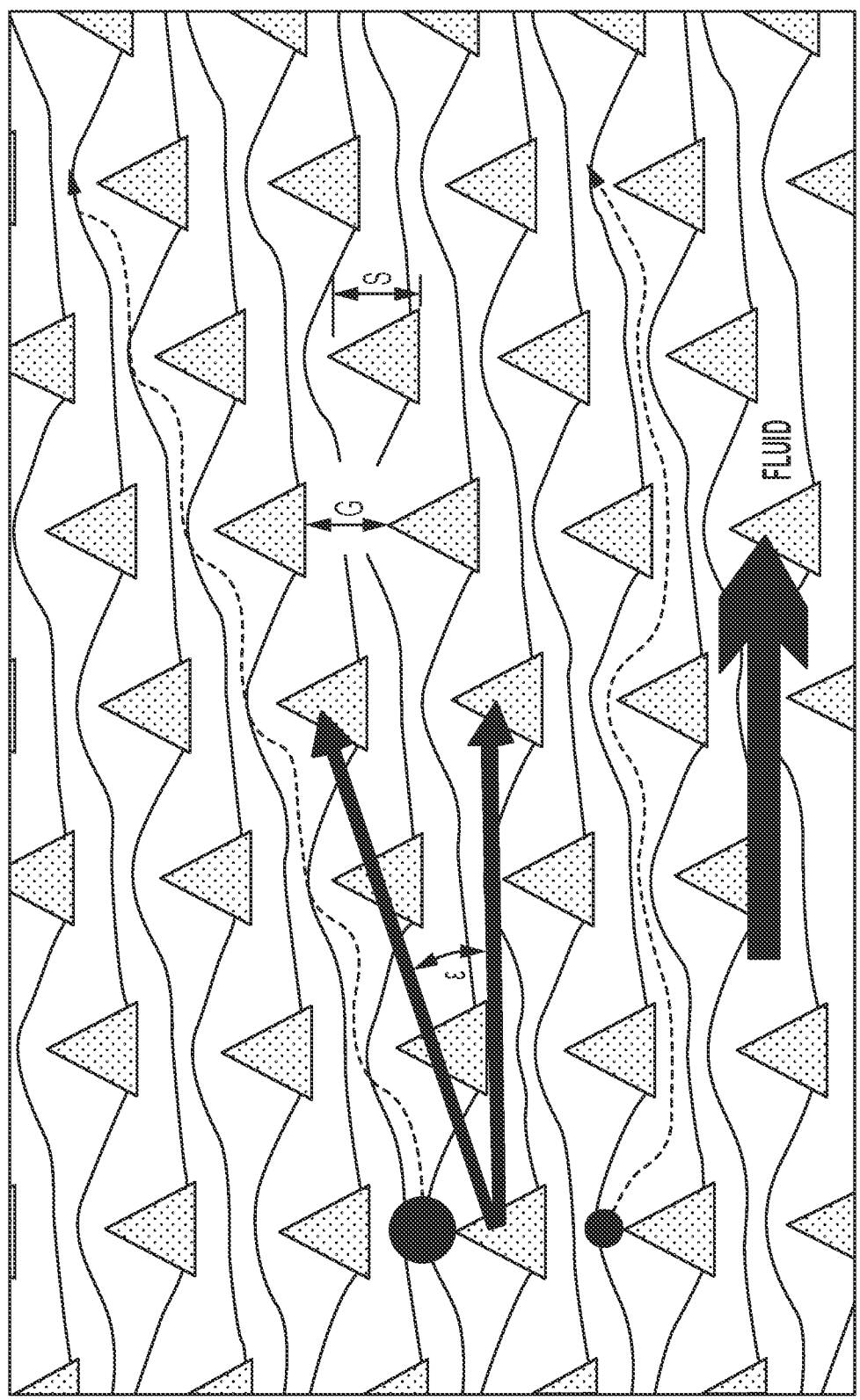
FIG. 6A is a schematic diagram of cross-section of a "bump array" device having equilateral triangularly-shaped obstacles disposed in a microfluidic channel. In the figure, fluid flows in the left- to right direction, as indicated by the arrow marked, "Fluid." In this array, equilateral triangular posts are disposed in a parallelogram lattice arrangement that is tilted with respect directions of fluid flow. Other lattice arrangements (e.g., square, rectangular, trapezoidal, hexagonal, etc. lattices) can also be used. The tilt angle ϵ (epsilon) is chosen so the device is periodic. In this embodiment, a tilt angle of 18.4 degrees (⅓ radian) makes the device periodic after three rows. The tilt angle ϵ also represents the angle by which the array direction is offset from the fluid flow direction. The gap between posts is denoted G with equilateral triangle side length S. Streamlines are shown extending between the posts, dividing the fluid flow between the posts into three regions ("stream tubes") of equal volumetric flow. A relatively large particle (having a size greater than the critical size for the array) follows the array tilt angle when fluid flow is in the direction shown. A relatively small particle (having a size smaller than the critical size for the array) follows the direction of fluid flow.

Deterministic lateral displacement is a size-based particle separation technique that relies on selective displacement of particles by an array of obstacles disposed in a flowing fluid. FIG. 6A illustrates a schematic of the relevant array parameters and important features of the devices described in this example. The obstacle array is composed of columns of posts in which each adjacent column is offset a small distance with respect to larger channel walls that dictate the direction of bulk fluid flow ("FLUID" in FIG. 6A). In this case, the posts are equilateral triangles with side length S (contrary to FIG. 6A, S is the side length, not the distance from a vertex of the triangle to the base opposite that vertex). This offset produces an array where an axis along which the obstacles are situated is situated at a tilt angle $\epsilon$ with respect to the direction of fluid flow. The tilt angle is selected such that the array is periodic after $1/\epsilon$ rows. In this case, the fluid flowing through gaps between posts (length of gap is designated G in FIG. 6A) can be partitioned into an integer number of stream tubes delineated by stagnation streamlines. Constrained by the periodicity and the direction of average fluid flow, each of these stream tubes carries an equal volumetric flux.

Particles suspended in the fluid exhibit one of two behaviors depending on their size relative to the width of stream tube nearest to the post as they move through a gap. Unperturbed by other effects, particles will roughly follow the stream tubes in the fluid flow. This behavior is observed for particles having radii narrower than the stream tube width. These particles, shown as the lower particle and dotted trajectory in FIG. 6A, are not affected by the posts and weave through the array while remain within the bounds of a single stream. As a result, they travel on average in the same direction as the bulk fluid flow. Particles having radii larger than the stream tube width, denoted as the upper particle and dotted trajectory in FIG. 6A, do not fit within a single stream tube as they travel through the gap. Those larger particles are deterministically displaced by the post across the stagnation streamline into the adjacent stream tube. Because of the way the stream tubes cycle through their position in the gap, this displacement will occur at every column of posts and the larger particle will travel along the array axis (i.e., in the array direction, which differs from the bulk fluid direction by the tilt angle E). This binary behavior leads us to describe a critical size which separates these two behaviors. As the particles to be separated are most frequently described by their diameter, we denote the critical size as twice the width of the stream tube nearest to the post in the gap between posts.

Figure 6B:
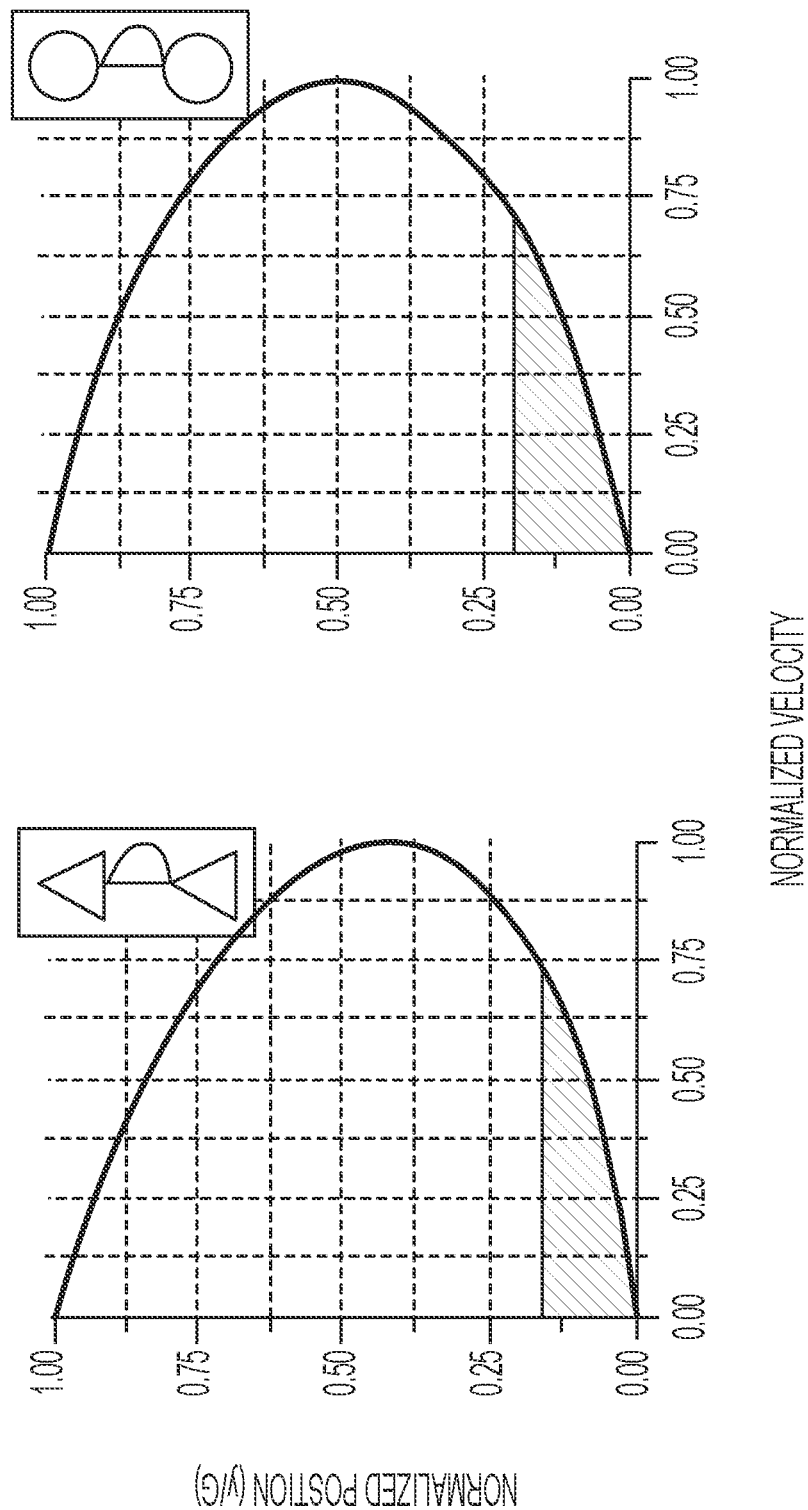
FIG. 6B is a comparison of normalized velocity flow between two equilateral triangular posts (left panel) and normalized velocity flow between two circular posts (right panel). The shaded portions represent an equal proportion of area-under-the-curve, demonstrating that the critical radius for particles flowing past the point of the triangle is significantly smaller (<15% gap width) than the critical radius for particles flowing past the round post (>20% gap width).

Changing the post shape can have a strong effect on the critical particle size by changing the shape of the flow profile through the gap. Alterations to the flow profile alter the width of the stream tubes nearest the posts that define a gap. Because critical particle size is directly related to these widths, alteration to the flow profile within a gap also alters the critical size(s) defined by the gap. By changing the cross sectional shape of the posts from the typical circular shape to equilateral triangles, an asymmetry is created in the flow profile through the gap that shifts more fluid flux towards the triangle vertex, as shown in FIG. 6B. This results in different stream tube widths at the top (adjacent the flat edge of a triangular post) and bottom (adjacent the vertex of a triangular post) of the gap and gives the array two distinct critical particle sizes.

The shift in flux towards the vertex of the triangle leads to a reduced stream tube width along this edge and hence reduces the critical particle size corresponding to that stream tube and edge, relative to a similar array with circular posts. This is demonstrated in the two panels of FIG. 6B, which shows numerically simulated flow profiles across the gaps. The two flow profiles, normalized to the width of the gap between posts and the maximum velocity, are plotted side by side for comparison. The fluid constituting the first stream tube for tilt angle $\epsilon=\frac{1}{10}$ has been shaded to emphasize the difference in stream width, decreasing from about 20% of the gap bounded by circular posts to about 15% of the gap bounded by triangular posts. This shift is central to the reduction in critical particle size behavior exhibited by devices with triangular posts. The shifted flow profile created by triangular posts can be used to create a deterministic microfluidic ratchet, as discussed in Example 1. In the information discussed in this example, the focus is on improvement to continuous flow particle separation devices and the deterministic lateral displacement of particles within them that are enabled by changing the post shape.

Figure 7:
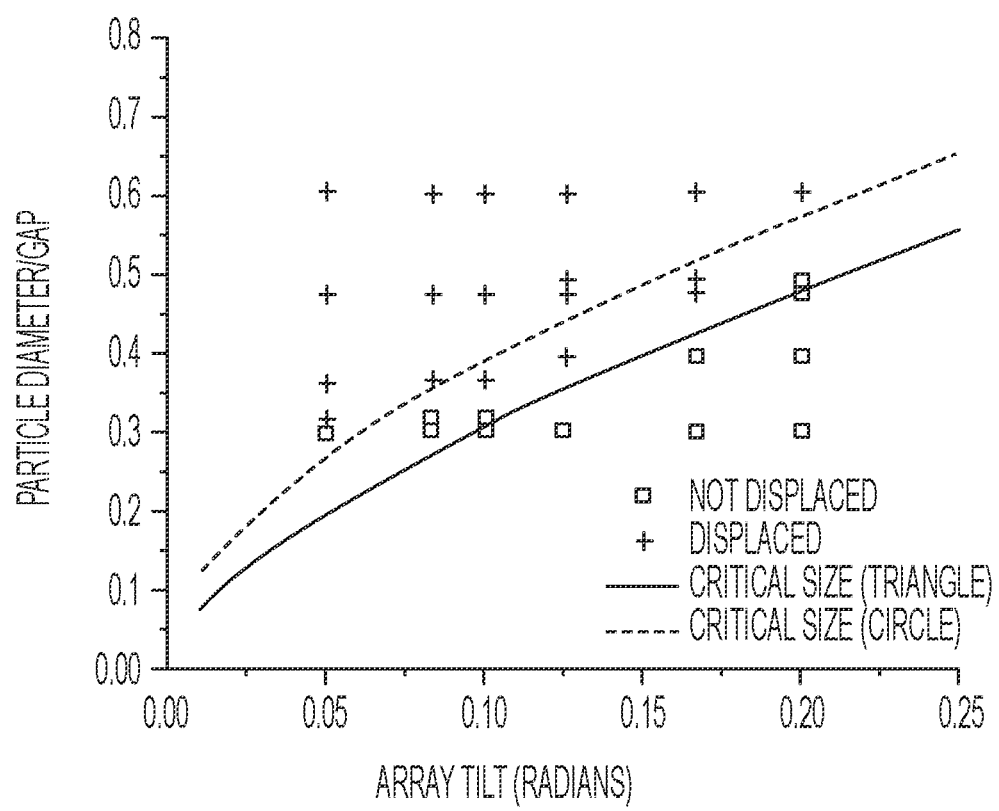
FIG. 7 is a graph illustrating hypothetical and experimental effects of the tilt angle ("Array Tilt" in FIG. 7) on particle displacement.

The reduction in critical particle size enabled by triangular posts was characterized by examining the behavior of fluorescent beads of in arrays with various amounts of array tilt and comparing the results to theoretically predictions. FIG. 7 shows observed particle behavior (displaced by the array or not displaced by the array) normalized to the gap size versus array tilt as well as predicted critical particle sizes using the method described by Inglis et al., 2006, Lab Chip 6:655-658. The lines in FIG. 7 represent the predicted critical particle size for a given tilt angle the solid line representing predictions for arrays with triangular posts and the dotted line representing predictions for arrays with round posts. Particles above the line are expected to be displaced by the array, particles below the line are not expected to be displaced. The data demonstrated that there is reasonable agreement with the predicted behavior for higher tilt angles while there is some deviation at the shallower tilt angles, especially at a tilt angle $\epsilon$ of $\frac{1}{20}$ radians. This deviation could be caused by the flow through the array not being completely horizontal, which will have a large affect at shallower array tilts, or because of rounding of the triangular post edges, which will be discussed later in this example.

The predicted particle behavior for circular posts, signified by the dotted line, has been added as a comparison. For any practical tilt angle (between $\frac{1}{5}$ and $\frac{1}{100}$), the critical size in an array with triangular posts is substantially smaller than the critical size in a similar array with circular posts, the difference amounting to up to 10% of the gap for the steeper tilt angles. These properties allow smaller particles to be separated by an array of triangular posts than can be separated by an array of round posts having the same gap spacing. These properties also mean that the gap spacing for triangular posts that is necessary to separate particles of a selected size is larger than the corresponding gap spacing for round posts that would be necessary to separate the same particles.

In either case, a reduced critical particle size as a fraction of the gap is useful in reducing clogging in the array. One of the major limitations of these arrays is that particles larger than the gap will clog the entrance, causing loss of function. Biological samples often contain species with a broad range of sizes so careful filtering or multiple separation stages are necessary to ensure that the array continues to function. Using triangular posts allows one to increase the size of the gap for a given critical particle size and reduce the chances that the array will clog. FIG. 8 illustrates how much larger the gap between posts can be made as a function of the array tilt. Plotted as a ratio of the two gaps for a fixed critical particle size, a minimum 20% improvement can be seen with increasing gap size as the tilt is reduced, with a ratio of 1.25 for a tilt angle of $\frac{1}{4}$ and a ratio of 1.94 for a tilt angle of $\frac{1}{100}$. Thus, shallower tilt angles facilitate use of larger gaps at the cost of a smaller separation angle and increased array size. However, larger gaps provide another benefit in terms of increased array throughput.

A throughput comparison between an array with triangular and circular posts showed a substantial increase in average velocity for a given pressure drop in the array with triangular posts. Arrays with triangular posts or with circular posts were constructed with nearly identical characteristics. They each had the same overall channel width and length, depth, tilt angle ($\frac{1}{10}$), and post size (the diameters of round posts were equal to the side lengths of the equilateral triangular posts). The single variation was the gap between posts, which was designed and verified with numerical simulation to give a critical particle diameter of approximately 3.2 microns for both arrays. Those numerical simulations indicated that the critical particle diameter was achieved using a gap of 10.5 microns in arrays with triangular posts and a gap of 8.3 microns in arrays with circular posts.

The trajectories of 500 nanometer fluorescent beads were recorded with an electron multiplying charged coupled device (EMCCD) camera capturing video at 10 frames per second and then analyzed using MATLAB™ software for a given pressure gradient across the array.

Small particles that would not be displaced (i.e., bumped) by the array were chosen so they would sample each of the flow streams evenly and provide an accurate representation of the overall average fluid velocity.

Figure 9:
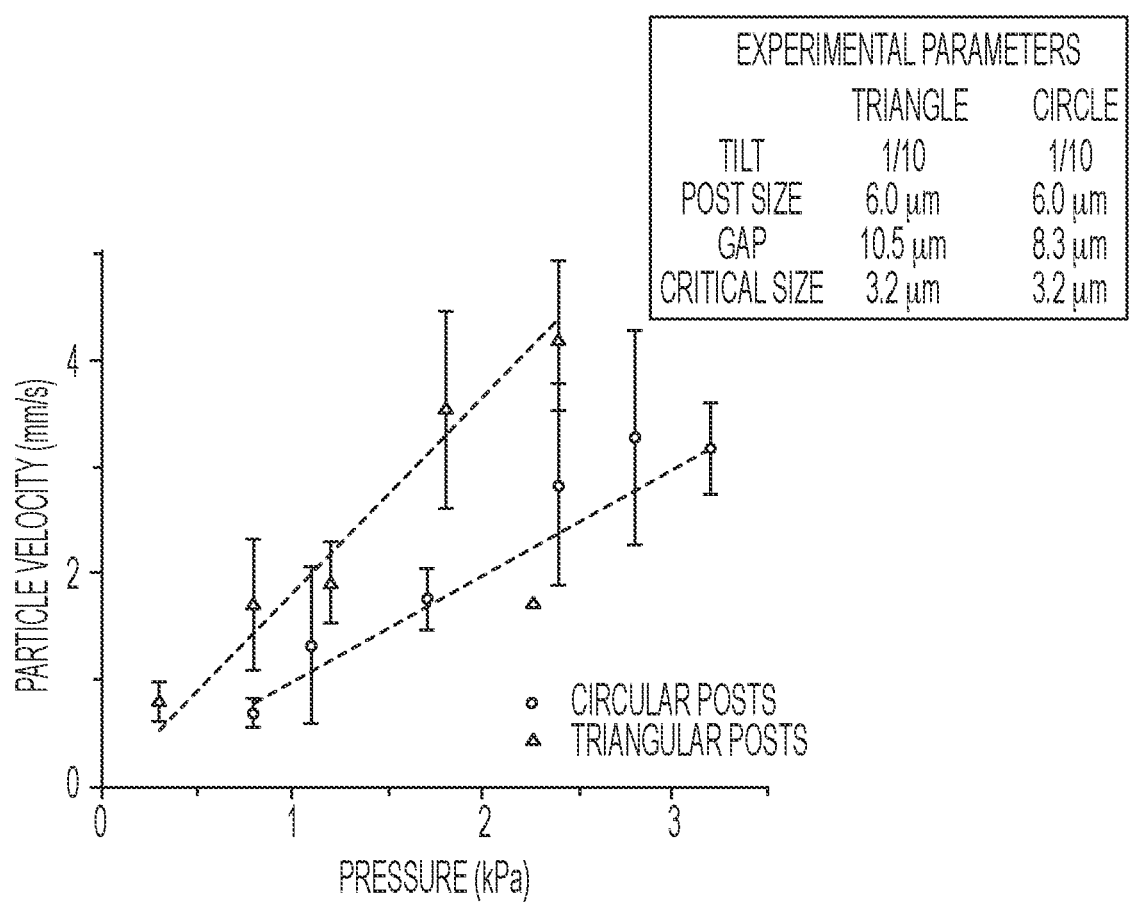
FIG. 9 is a graph illustrating the effect of applied pressure on particle velocity in bump arrays having triangular posts (data shown as triangles) and bump arrays having circular posts (data shown as circles).

The average particle velocities are plotted in FIG. 9 as a function of pressure gradient along with a weighted linear fit. The fitted lines demonstrate that particles in the triangular post array moved much faster. The upper range of pressures was limited by the field of view of the microscope and the capture speed of the camera. Beyond several kPa in pressure, the particles traversed the entire field of view within one or two frames of the video and no accurate estimate of velocity could be made. However, since the Reynolds number in these experiments is on the order of $10^{-2}$, the linear fit can safely be extended into the tens of kPa range to match the expected linear relationship between velocity and pressure that is seen for low Reynolds number flows. The posts need not be triangular in cross-section. Posts having other (square, oblong, or irregular) cross-sectional profiles can also be used, so long as the shape of the obstacles causes the gap to be asymmetric.

Comparing the slopes of the two linear fits in FIG. 9, it can be seen that particles in the array with triangular posts traveled 85% faster on average than those in an array with circular posts. This result agrees with numerical simulation performed with COMSOL™ software that showed that the average velocity for was 82% faster for triangular posts. The mechanism behind these findings can be understood by drawing an analogy to Poiseuille flow between two parallel plates, where the average velocity for a fixed pressure gradient is proportional to the smallest distance between the plates squared. The analogy is not exact because the confining structure is an array of posts instead of two parallel plates, but underscores the benefits of increasing the width of the gap, where just a few microns yields a substantial increase in throughput.

Figure 10:
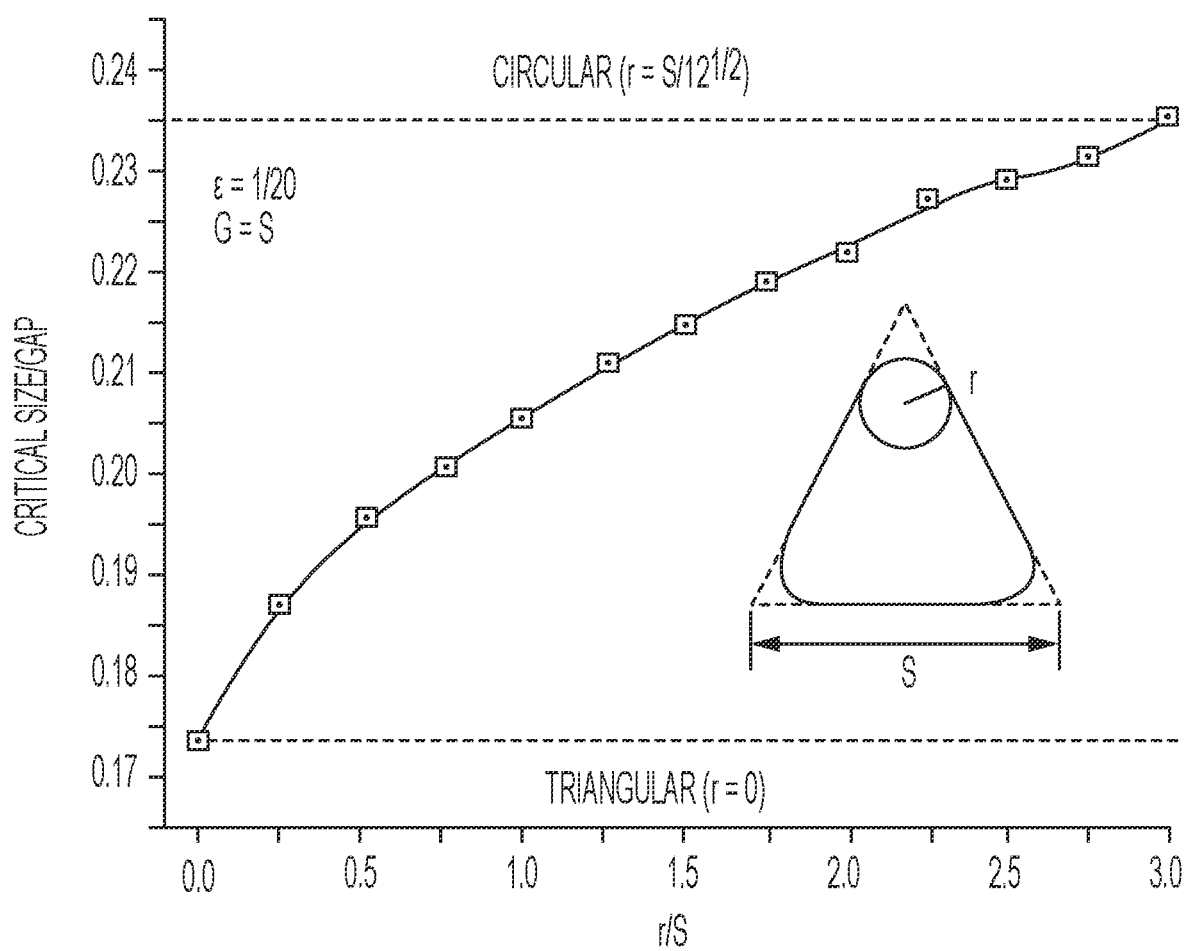
FIG. 10 is a graph illustrating the effect of obstacle edge roundness (expressed as r/S) on the critical size exhibited on the side of a gap bounded by the edge.

The gains achieved by changing the post shape are degraded if care is not taken to maintain sharp post vertices. FIG. 10 shows the effect of rounding triangular post edges on the critical particle size. An array with 10 micron posts, 10 micron gaps between posts, and tilt angle of $\frac{1}{30}$ was simulated using COMSOL™ software, with the vertices rounded to various radii of curvature ranging from none (r=0) to complete rounding where the final shape is a circle (r=S/$12^{1/2}$). Flow profiles across the gaps were extracted for each rounding and the critical size for the given tilt was calculated using previously stated methods. As shown in FIG. 10, there is a dramatic increase in the critical particle size as the post shape transitions from triangular to circular. Starting at 0.174 G when the post is completely triangular (i.e., r=0), critical particle size increases 35% to 0.235 G when the post is completely circular (r=S/12$^{1/2}$). The transition suggests that if a fabrication process that produces an undesirable vertex rounding, using larger posts (increasing S) will help to maintain the decreased critical particle size that results from using triangular posts.

This observation also helps to explain the deviation from expected behavior observed for some of the fluorescent beads in FIG. 7. SEM images of the posts show vertex rounding (r/S) of 0.118±0.006, which corresponds to an increase in the critical particle size from 0.93 microns to 1.12 microns.

ment. Further details can be found in "Sealing and bonding techniques for polymer-based microfluidic devices" by Abdirahman Yussuf, Igor Sbarski, Jason Hayes and Matthew Solomon, which is herby incorporated by reference herein in its entirety.

Further bonding techniques include Adhesive Bonding, Pressure sensitive tape/Lamination, Thermal Fusion Bonding, Solvent Bonding, Localized welding, Surface treatment and combinations thereof. Further details can be found in "Bonding of thermoplastic polymer microfluidics" by Chia-Wen Tsao and Don L. DeVoe, Microfluid Nanofluid (2009) 6:1-16, which is herby incorporated by reference herein in its entirety.

In some embodiments, the device is made from a polymer and/or plastic. The polymer and/or plastic can be hydrophilic and/or wettable. Table 1 summarizes properties of some plastics.

TABLE 1

Summary of physical properties for common microfluidic thermoplastics

| Polymer | Acronym | $T_g$ (° C.) | $T_m$ (° C.) | CTE ($10^{-6}$ ° C.$^{-1}$) | Water absorption (%) | Solvent resistance | Acid/base resistance | Optical transmissivity Visible | UV$^a$ |
|---|---|---|---|---|---|---|---|---|---|
| Cyclic olefin (co)polymer | COC/COP | 70-155 | 190-320 | 60-80 | 0.01 | Excellent | Good | Excellent | Excellent |
| Polymethylmethacrylate | PMMA | 100-122 | 250-260 | 70-150 | 0.3-0.6 | Good | Good | Excellent | Good |
| Polycarbonate | PC | 145-148 | 260-270 | 60-70 | 0.12-0.34 | Good | Good | Excellent | Poor |
| Polystyrene | PS | 92-100 | 240-260 | 10-150 | 0.02-0.15 | Poor | Good | Excellent | Poor |
| Polypropylene | PP | −20 | 160 | 18-185 | 0.10 | Good | Good | Good | Fair |
| Polyetheretherketone | PEEK | 147-158 | 340-350 | 47-54 | 0.1-0.5 | Excellent | Good | Poor | Poor |
| Polyethylene terephthalate | PET | 69-78 | 248-260 | 48-78 | 0.1-0.3 | Excellent | Excellent | Good | Good |
| Polyethylene | PE | −30 | 120-130 | 180-230 | 0.01 | Excellent | Excellent | Fair | Fair |
| Polyvinylidene chloride | PVDC | 0 | 76 | 190 | 0.10 | Good | Good | Good | Poor |
| Polyvinyl chloride | PVC | 80 | 180-210 | 50 | 0.04-0.4 | Good | Excellent | Good | Poor |
| Polysulfone | PSU | 170-187 | 180-190 | 55-60 | 0.3-0.4 | Fair | Good | Fair | Poor |

$T_m$ melting temperature, CTE coefficient of thermal expansion
$^a$high UV transmissivity often requires the selection of special polymer grades, e.g. without stabilizer or other additives Materials of Construction and Surface Chemistry In some embodiments, the device is made by hot embossing PMMA and polycarbonate. Due to their low cost compatibility with replication-based fabrication methods, thermoplastics can represent an attractive family of materials for the fabrication of lab-on-a-chip platforms. A diverse range of thermoplastic materials suitable for microfluidic fabrication is available, offering a wide selection of mechanical and chemical properties that can be leveraged and further tailored for specific applications. While high-throughput embossing methods such as reel-to-reel processing of thermoplastics is an attractive method for industrial microfluidic chip production, the use of single chip hot embossing is a cost-effective technique for realizing high-quality microfluidic devices during the prototyping stage. Here we describe methods for the replication of microscale features in two thermoplastics, polymethylmethacrylate (PMMA) and polycarbonate (PC), using hot embossing from a silicon template fabricated by deep reactive-ion etching. Further details can be found in "Microfluidic device fabrication by thermoplastic hot-embossing" by Yang and Devoe, Methods Mol. Biol. 2013; 949: 115-23, which is herby incorporated by reference herein in its entirety.

The device can be sealed and bonded in any suitable manner. The main challenge can be bonding planar microfluidic parts together hermetically without affecting the shape and size of micro-sized channels. A number of bonding techniques such as induction heating are suitable. The channels can be fabricated by using Excimer laser equip- The microfluidic device can be fabricated in any suitable manner. Some techniques include Replica molding, Soft-lithographt with PDMS, Thermoset polyester, Embossing, Injection Molding, Laser Ablation and combinations thereof. Further details can be found in "Disposable microfluidic devices: fabrication, function and application" by Gina S. Fiorini and Daniel T. Chiu, BioTechniques 38:429-446 (March 2005), which is hereby incorporated by reference herein in its entirety. The book "Lab on a Chip Technology" edited by Keith E. Herold and Avraham Rasooly, Caister Academic Press Norfolk UK (2009) is a resource for methods of fabrication, and such which is herby incorporated by reference herein in its entirety.

In some cases, the surface of the (plastic) device is treated to make it hydrophilic and/or wettable. Surfaces in microfluidics can play a critical role because they define properties such as wetting, adsorption and repellency of biomolecules, biomolecular recognition using surface-immobilized receptors, sealing and bonding of different materials. Two types of treatments generally exist to modify the surface properties of microfluidics: wet chemical treatments and gas phase treatments. Wet treatments can be simple in terms of infrastructure requirements; they can be flexible and fast to develop from a research standpoint. Surface treatment of microfluidics for production can be however best achieved using dry processes based on plasma and chemical vapor deposition. These treatments can eliminate the need for rinsing and drying steps, have high throughput capability and are highly reproducible.

In some cases, the treatment is a wet chemical treatment. Among the wet chemical treatments available, the formation of self-assembled monolayers (SAMs) is one of the most versatile and easy to use surface treatments. SAMs have been developed on metals, silicon oxides and polymers. Molecules in SAMs pack closely and are composed of a headgroup usually binding covalently to the substrate, an alkyl chain and a terminal functional group. The thickness of the SAM depends on the length of the alkyl chain and density of the molecules on the surface and is typically a few nanometers. SAMs can be easy to prepare and can be patterned with sub-micrometer lateral resolution. Different terminal groups can be used for defining the wetting properties of the surface as well as the affinity for or repellency of proteins. For glass surfaces, oxides and polymers that can be oxidized, grafting alkylsiloxanes to surfaces might be the simplest and most economical method. A wettability gradient from superhydrophobic to hydrophilic can be achieved by superposing a SAM-based wetting gradient onto microstructures in silicon that have varying lateral spacing.

Polymeric SAMs can comprise block copolymers and can have various three-dimensional structures, which gives the opportunity to vary their mode of grafting to a surface and the types of functionalities that they carry. Such layers can reach a significant thickness of several hundreds of nanometers and protect/functionalize surfaces more reliably than thinner monolayers. For example, a poly(oligo(ethyleneglycol)methacrylate) polymer brush can coat glass microfluidic chips to make them hydrophilic and antifouling.

Coating polymers onto surfaces to modify their properties is possible. For example, poly(ethyleneglycol) is often used to "biologically" passivate microfluidic materials and can be grafted onto PMMA surfaces of capillary electrophoresis microchips to make them hydrophilic. Poly(tetrafluoroethylene) can be used to make chemically resistant microfluidics devices. Polymeric materials employed to fabricate microfluidics can be modified in many ways. Often, functional groups such as amines or carboxylic acids that are either in the native polymer or added by means of wet chemistry or plasma treatment are used to crosslink proteins and nucleic acids. DNA can be attached to COC and PMMA substrates using surface amine groups. Surfactants such as Pluronic® can be used to make surfaces hydrophilic and protein repellant by adding Pluronic® to PDMS formulations. It is even possible to spin coat a layer of PMMA on a microfluidic chip and "dope" the PMMA with hydroxypropyl cellulose to vary its contact angle.

Proteins themselves can be used on surfaces to change surface wettability, to passivate a surface from non-specific protein binding and for functionalization. Proteins readily adsorb to hydrophobic substrates such as PDMS and polystyrene. By exploiting this property, PDMS substrates can be coated with neutravidin to immobilize biotinylated proteins or biotinylated dextran. Antibody coatings can be optimized depending on the hydrophobicity of the polymeric substrate. Bovine serum albumin is the most commonly used protein to passivate surfaces from non-specific adsorption and is easy to deposit spontaneously from solution to hydrophobic surfaces. On a hydrophilic substrate, a layer of hydrophobic poly(tetrafluoroethylene) can first be coated to enable the subsequent deposition of bovine serum albumin. Heparin, a biological molecule widely used as an anticoagulant, can be deposited from solution onto PDMS to make microchannels hydrophilic while preventing adhesion of blood cells and proteins.

In some embodiments, the device undergoes a gas phase treatment. Plasma processing not only can modify the chemistry of a polymeric surface but it also can affect its roughness significantly thereby exacerbating wetting properties to make surfaces superhydrophilic and fluorocarbons can be plasma deposited to make surfaces superhydrophobic. Polymeric surfaces can be patterned using ultraviolet light to initiate radical polymerization followed by covalent grafting of polymers. Plasma-induced grafting is used to attach poly(ethyleneglycol) onto polyamide and polyester surfaces to render them antifouling Dextran is a polysaccharide comprising of many glucose molecules that can be coated to make hydrophilic antifouling surfaces. A common starting point to modifying polymers is to introduce surface hydroxyl groups using a plasma treatment followed by grafting a silane and dextran layer. Similarly, PDMS can be superficially oxidized using ultraviolet light for grafting a dextran hydrogel.

The large surface to volume ratio of microfluidic structures makes any potential surface-analyte/reagent interaction a potential issue. Therefore, irrespective of the method used to treat the surfaces of a microfluidic device for POC testing, the surfaces of the device ideally should not attract and deplete analytes or biochemicals that are needed for the test. In addition, surface treatments should not interfere with signal generation and acquisition principles of the device. Further details can be found in "Capillary microfluidic chips for point of care testing: from research tools to decentralized medical diagnostics" a thesis by Luc Gervais, Ecole polytechnique federale de Lausanne, 23 Jun. 2011, which is herby incorporated by reference herein in its entirety.

Stem Cells for Transplantation

Hematopoietic stem-progenitor cell (HSPC) transplantation is an established therapy for many malignant and non-malignant diseases, with ~50,000 transplants performed per year using autologous or allogeneic HSPCs from mobilized peripheral blood stem cells (PBSCs), bone marrow (BM), or umbilical cord blood (UCB), in order of frequency. UCB is an especially attractive source of HSPCs due to its easy availability as a banked, HLA-typed and infectious disease-tested product with reduced risk of generating graft-versus-host disease in transplant recipients despite HLA mismatch. >20,000 UCB transplants have been performed in the last 20 years, and tens of thousands of UCB units are cryopreserved each year.

One of the major problems in UCB transplantation is the low total number of HSPCs in the available small volume of UCB units. This leads to high risk for delayed engraftment or engraftment failure (with attendant high mortality, morbidity and costs), especially when UCB is transplanted into adult or larger child recipients. Only ~100 (up to 300 ml rarely) of blood can be harvested from the placenta in the delivery room. Harvested units must be depleted of erythrocytes before storage but the techniques of centrifugation using apheresis technology (to obtain a leukocyte-enriched "buffy coat"), differential sedimentation in viscous media (e.g. hydroxyethyl starch[HES]), or density gradient centrifugation (even with newer automated apparatus) all result in both incomplete erythrocyte removal and average loss of ~25% of leukocytes and HSPCs. Since success and speed of engraftment have been shown to depend on the numbers of leukocytes and HSPCs administered per transplant recipient body weight, it is essential to develop new cell separation methods to provide high yields of highly pure, viable leukocytes and HSPCs from harvested UCB. Such efficient methods would also be valuable for processing of PBSC and BM harvests, to maximize the numbers of HSPCs for transplant and potentially reduce the amount of donor blood/BM collected.

Figure 16B:
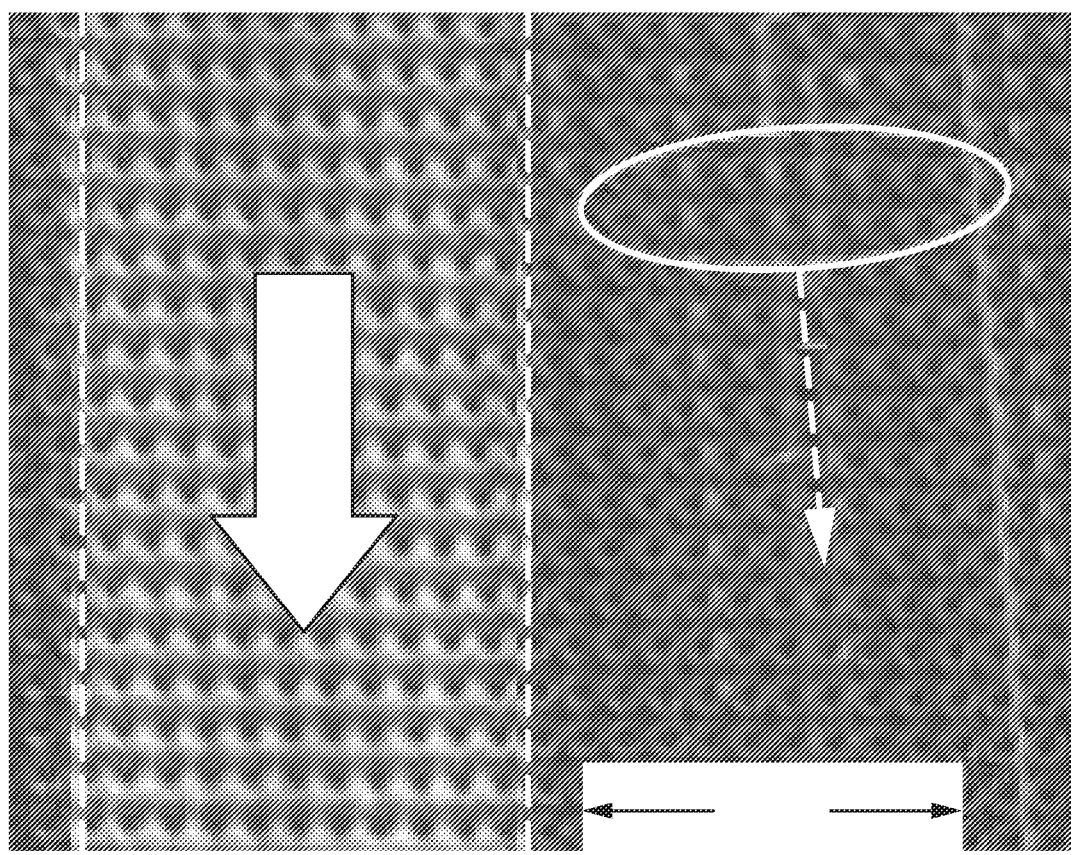
FIG. 16B shows time lapse images of leukocytes being enriched.

FIG. 16A is a top view of a device containing a periodic array of microposts for Deterministic Lateral Displacement (DLD). The flow bifurcates around posts in successive rows, with 3 different "streamtubes" illustrated as purple, blue and green. The fluid streams change their relative positions, but do not mix as they flow in a laminar fashion from gap to gap through the matrix. Small cells will remain in the same streamtube, moving on average in the same direction as the fluid. Large cells will be bumped by the posts and displaced to the right into the next streamtube and be progressively separated from the original mixture; FIG. 16B shows time lapse images of leukocytes being enriched from adult blood on a DLD microchip. The circles are the tops of the microposts. On the left is the flow of erythrocytes, reflecting white light. The leukocyte path is the blue nuclear stain, leading to streaks moving away from the erythrocytes.

Described herein is a microfluidic technology for size-based cell separations that provides a >90% yield of erythrocyte-depleted leukocytes from whole adult blood. This technology can be applied for small samples (100 µl) of adult blood prior to research or clinical diagnostic flow cytometry. The microfluidic technology can deplete erythrocytes from clinical UCB harvests for (cryopreservation and then) transplantation. In some cases, the method further characterizes this technology for sterile processing of UCB, PBSC and BM harvests. In some cases, the device is applied for additional purification of these and other types of stem cells, and potentially other cell therapy products.

There is a significant unmet medical need for a system to thoroughly deplete erythrocytes and recover leukocytes in high yield from UCB. This DLD microfluidic technique, can provide efficient, size-based depletion of erythrocytes from leukocytes in experiments using small, fresh samples of adult human peripheral blood. One aspect of DLD is that the path cells take through the microchip is based on size and is deterministic, i.e. determined and not subject to random processes. Unlike in bulk processes, such as HES and centrifugation, each cell is treated individually so that it interacts with the features in the microfluidic system and is directed into either the product or waste streams. The "continuous flow" nature of DLD offers the potential for high throughput without degrading resolution and for low-cost implementation. No previously existing UCB processing method can recover leukocytes that are >90% pure and >90% viable, and are obtained in >90% yield, i.e. the "90/90/90" performance criteria that will be able to achieve using the microfluidic device. Since 50% of donated UCB harvests cannot currently be used clinically due to low post-processing leukocyte and CD34+ cell numbers, the value proposition to blood banks and transplant centers is clear: the technology described here can deliver greater numbers of higher quality transplant grafts (i.e. more grafts that retain more HSPCs). This approach would replace the current standard processing procedures for UCB grafts because of its potential to significantly reduce morbidity, mortality and costs associated with failed or delayed hematopoietic recovery and engraftment. The commercial attractiveness of the UCB processing market continues to grow, with >100 UCB banks currently operating.

In some cases, the highly effective microfluidic separations of adult blood can be extended to UCB, and will results in an output product containing phenotypic HSPCs that is composed of >90% leukocytes (i.e. <10% erythrocytes) in >90% yield (based on starting leukocyte numbers), and with >90% leukocyte viability (90/90/90 criteria). In some cases, the method is scaled to a flow rate of >100 ml/hr, in order to process donated UCB units in <1-3 hrs.

The microfluidically-separated UCB leukocytes can be highly (>90%) viable and depleted of erythrocytes (>90% leukocytes). The types of leukocytes recovered may not differ significantly from their input distribution. Recovery of a higher number of phenotypic HSPCs (i.e. Procount: CD34+/CD45+) with this method is possible than generally observed using Ficoll-Paque or HES, and without skewing of any particular lineage.

In some cases, >100 ml/hr may be difficult if the HSPCs are extremely sensitive to shear (from the flow rate, unlike leukocytes which can tolerate 30× faster rates as mentioned just above). In some instances, there are at least 5 combinable options for handling shear sensitive cells: (1) redesign the post shape to reduce the shear stress (i.e. asymmetric posts to enable wider gaps); (2) design taller posts to allow a greater flow cross section; (3) design asymmetric posts that enable a higher separation angle (design parameter c increasing from 0.03 to 0.06, and thus more arrays in a smaller area); (4) design a larger chip area; and (5) design tighter packing of parallel arrays onto an existing chip area. In some cases, these five options can combine for a 12-fold improvement. In some cases, these modifications, combined with a modest 2-fold faster flow rate, to allow one to process UCB at 144 ml/hr. In some cases, novel stacking of such sorting chips, so >10 chips can be run in parallel, with the same footprint and only 1 set of external connections (for low cost) is performed.

Modify Cell Separation System for Aseptic Clinical Use.

Designing the system as a closed, sterile system for UCB processing can prevent microbiological contamination and allow for functional assessment of HSPCs.

In some cases, the device is suitable for sterile separation of cells that will allow one to functionally characterize HSPCs in the output product. This closed system can use parts that can be either sterilized and used just once (e.g. blood bags) or sterilized repeatedly (e.g. connecting devices, seals, and potentially microchips). In some cases, individual components are sterilized by gamma irradiation, steam, ethylene oxide or other standard methods. In some cases, a common sterilization process that is compatible with the various materials in contact with the cell stream is used. The common process can allow pre-assembly of microchips, manifolds, elastomeric seals and interconnecting tubing sets prior to sterilization, thereby minimizing the chance of microbial contamination during device assembly in controlled environments such as laminar flow hoods or clean rooms.

Deterministic lateral displacement (DLD)-based purification on the basis of cell size can be extended to purification of subsets of other types of blood cells and other types of stem cells. The technology can be quickly integrated into current clinical practice to process UCB and can also be adapted to purify HSPCs more highly as well as to isolate other stem cell types and sources (e.g. adipose tissue).

The use of DLD to deplete RBCs from >100 ml quantities of UCB for hematopoietic transplant is clinically beneficial. Furthermore, the issues associated with UCB, which can be "notoriously sticky and frequently clumps", may require that one develop innovative solutions for processing these samples in a microfluidic environment. These approaches are described herein.

Shear Stress:

Increasing pressure to disrupt cell aggregates can injure cells in some cases as the fluid stream squeezes through the gaps between posts, since shear force is proportional to flow rate. In some cases, one uses low fluid velocities (~5 mm/sec), >90% viability of leukocytes after they passed through the chip, where the calculated shear rates (shear stress normalized by viscosity) were ~500 sec$^{-1}$, similar to shear rates that circulating leukocytes experience in vivo.

Scale:

In some cases scale up sorting of leukocytes, since flow rates of (only) ~100 mm/sec will achieve the desired ~5 ml/min throughput. The resistance to fluid flow of a chip is inversely proportional to the square of the gap size. In some cases, one may use a large gap size, but the critical sorting size, which is set by our need to isolate leukocytes, is typically 30-50% of the gap (depending on some detailed parameters). In some cases, engineering the shape of the posts (using asymmetric posts instead of the usual circular posts) allows one to make the gap (and thus the throughput rate) larger without raising the critical sorting size. Finally, in the unlikely event that, e.g. because of effects on cell viability, it is not possible to flow stem cells through our chips at high rates, even with optimized post geometries, one may etch deeper channels, increase the chip area, using a higher separation angle to add more parallel post arrays, and stacking chips.

Clogging:

Higher flow rates can greatly reduce clogging, and larger gaps between posts can reduce clogging as well. UCB can be anticoagulated at the time of collection, which can effectively block the clotting protein cascade. Clotting can be also be addressed by careful visual macroscopic inspection followed by exclusion from our experiments of extensively clotted samples, which is consistent with clinical practice; no previous cell separation method can deal with donor cell harvests that are already extensively clotted. Furthermore, pre-filtration of samples through 20 uM mesh prior to processing is an explicit part of the protocol in some cases. In some embodiments, chemical chip surface treatments which resist cell or protein adhesion, such as an mPEG-silane polymer may be used.

The growing popularity of umbilical cord blood (UCB) as a source of hematopoietic stem-progenitor cells (HSPCs) for transplant results from its easy availability, reduced risk of graft-vs-host disease, and applicability for use across wide histocompatibility differences. However, the potential of UCB transplants is limited currently by the low total number of HSPCs that can be obtained from placental blood. Ideally, clinical grafts should be depleted of erythrocytes after harvest in order to (1) prevent transfusion reactions in patients, (2) reduce fluid volume loads and amounts of cryoprotectant administered to patients (e.g. toxic effects of dimethylsulfoxide [DMSO] cryoprotectant include hypertension and cardiac arrhythmias), and (3) minimize necessary expensive storage space in blood bank freezers[4-9]. Currently, blood banks rely on traditional depletion methods like hydroxyethylstarch (HES) sedimentation and density gradient centrifugation. HES sedimentation is a manual technique and results in high residual erythrocyte contamination (with erythrocytes comprising >30% of the output volume) and significant loss of leukocytes and CD34+ HSPCs (>20% loss on average, considerably worse in some cases). Automated systems, such as Sepax and AXP, offer standardization of UCB processing, but these density gradient centrifugation processes do not typically improve erythrocyte depletion or leukocyte recovery. Prepacyte-CB, a sedimentation method, accomplishes more effective erythrocyte depletion but still loses >25% of leukocytes. Because any loss of HSPCs significantly reduces the clinical utility of UCB and leads to high risk for delayed engraftment or engraftment failure (with attendant high mortality, morbidity and costs), new processing methods are urgently needed to ensure high yields of highly pure, viable leukocytes for banking and transplant.

Described herein is a fully integrated, scalable, microfluidic cell separation system capable of thoroughly removing erythrocytes from clinical HSPC transplant grafts derived from UCB harvests. The optimized system will recover >90% of input leukocytes and HSPCs at >90% purity and >90% viability ("90/90/90" criteria). The system can be poised for preclinical evaluation and extension to other hematopoietic samples (e.g. PBSC, BM), as well as for further purification of HSPCs and other stem cell types. This disclosure leverages a unique combination of multidisciplinary skills in microfluidic design and optimization, integration and fabrication, and hematopoietic cell biology.

The devices and methods can process harvested UCB, with the goal of recovering viable leukocytes and phenotypic HSPCs at the 90/90/90 criteria. The separated cells can be evaluated phenotypically by methods including flow cytometry. UCB may be more prone than adult peripheral blood to cell clumping, resulting in blockages in the device. Thus, the devices and protocols remove, prevent, and disperse cell aggregates. Approaches to increase sample throughput to clinical volumes of 100-300 ml/hr, evaluating the effects of various DLD geometries and comparing leukocyte purification, yield and viability with increasing flow rates are also described.

In some embodiments, (a) the instrument platform and components can be sterilized and (b) cells can be introduced and recovered in convenient blood bags.

Hematopoietic stem-progenitor cell (HSPC) transplantation is an established therapy for many malignant and non-malignant diseases. HSPCs are harvested clinically from 3 sources: G-CSF mobilized adult peripheral blood (PBSC), bone marrow (BM), and umbilical cord blood (UCB). Because erythrocytes increase both the risk of harmful side effects in transplant patients and the cost of cryopreservation, they must be depleted from the harvested HSPC tissues. The major problem in UCB transplantation is the low total number of HSPCs in the small volume (100-300 ml) of UCB units. This leads to high risk for delayed engraftment or engraftment failure (with attendant high mortality, morbidity and costs), especially in larger children or adult patients. Previous techniques, including density gradient centrifugation and differential sedimentation, result in incomplete erythrocyte depletion and may lose 25% leukocytes (on average) during processing. Since success and speed of engraftment depend on the numbers of leukocytes and HSPCs per recipient body weight, it is essential to develop new cell separation methods to ensure high yields of pure, viable leukocytes and HSPCs from harvested UCB. In some aspects, the devices and methods improve stem cell banking and transplantation by providing an efficient and robust processing system that results in superior recoveries of viable leukocytes and HSPCs. Microfluidic deterministic lateral displacement (DLD), in which the paths cells take through the microfluidic system is based on size and is deterministic, i.e. absolutely determined, not subject to random processes. The use of DLD to deplete erythrocytes from UCB for hematopoietic transplant; this is a new clinical use. The technology will also be extended for use with PBSC and BM harvests. The value proposition is clear: the devices and methods deliver greater numbers of higher quality transplant grafts (i.e. more grafts with more HSPCs) that will lead to greater transplant success.

EXAMPLES

Example 1—Leukocyte Enrichment from UCB

The methods can improve stem cell banking and transplantation by providing an efficient and robust processing system for clinical UCB, PBSC and BM harvests. The microfluidic separation method can efficiently and consistently deplete erythrocytes from UCB. In some cases, there may be problems with cell clumping in some clinical samples (principally due to dead/dying cells). In such cases, the device and/or protocol are optimized to address cell clumping. In some embodiments, the process is scaled up to purify >100 ml volumes of UCB per hour, preserving 90/90/90 performance.

In some cases, the blood sample is depleted of smaller-sized cells (i.e. erythrocytes, platelets) and the larger-sized cells of interest (i.e. leukocytes) are concentrated. Note that the unwanted smaller cells are present in blood at >1000-fold excess numbers over the desired leukocytes.

The microfluidic chips used can be approximately the size of a microscope slide. They contain arrays of microposts with geometries optimized to separate target cells by size via displacement of these cells from the blood sample into a product stream. The periodic array of micron-sized posts in the flow path creates an asymmetric bifurcation of laminar flow around the obstacles, leading to different flow directions for large versus small cells. As illustrated in FIG. 16A and 16B, small cells (erythrocytes) move down the array in the direction of the fluid flow while the larger cells (leukocytes) move along the tilted axis of the posts, away from the erythrocytes. The leukocytes eventually collect and concentrate along the right wall of the array (out of the photo's range), where they are collected separately from the waste (erythrocytes). The critical threshold size for displacement is determined by the size of the gaps, the row-to-row spacing, and the tilt of the post axis with respect to the fluid flow. The cell separation microchips are defined by photolithography and etched into a silicon substrate based on CAD-generated designs. The chips to date have been made using methods borrowed from the electronics industry of photolithography and etching.

configuration so that a small portion of sample remains in the system and is not processed. In some cases, the full sample will be sorted, and the leukocyte recovery will rise to 90% or better. Viability by trypan blue dye exclusion is >90% in all fractions. Granulocytes, lymphocytes, and monocytes are close to the initial "differential leukocyte" ratios.

Figure 17:
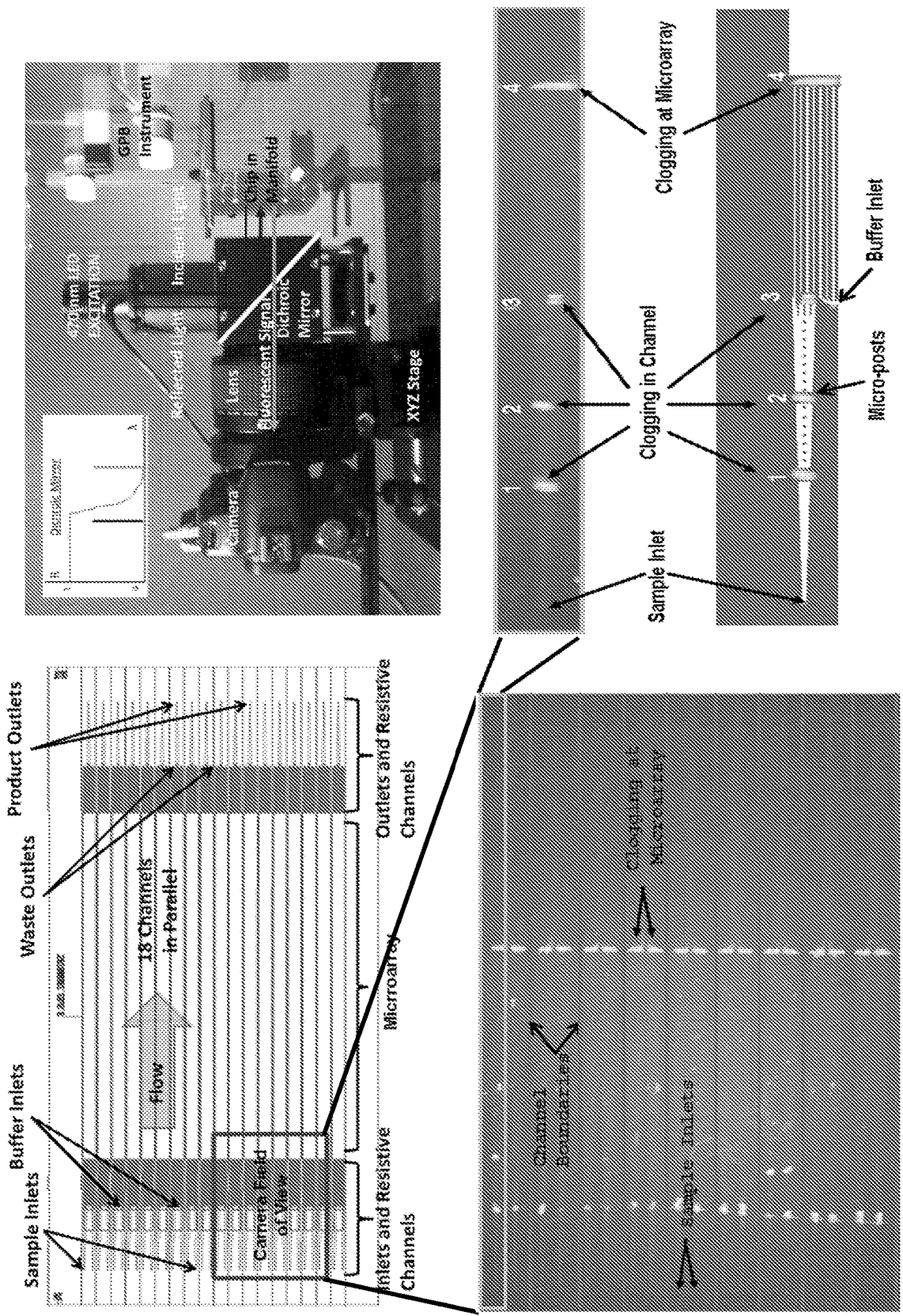
FIG. 17 shows an imaging setup with 470 nm source and dichroic mirror, flow direction is from left to right (top left panel), photo of nine parallel arrays exhibiting clogging as seen by fluorescent signal (bottom left panel), enlargement of one channel with clogging (bottom right panel).

The in-line imaging camera (FIG. 17) allows one to observe early events in a potential clogging process. FIG. 17 (bottom) shows aggregates of leukocytes (labeled green with Syto-13 dye Invitrogen) collecting in the sample inlet, with additional clogging at the DLD micropost array.

In some cases, there are not microposts near the inlet. In some cases, the device has deeper channels and made of less expensive materials (e.g. plastic) and new, cheaper materials.

Example 2—Characterize Performance of the Microfluidic Cell Separation Device with UCB Anticoagulated, deidentified UCB samples are obtained. Samples with visible macroscopic cell clumps are classified as inadequate and not processed further; the numbers of inadequate samples are tracked. For adequate samples, UCB samples are diluted in an equal volume of running buffer and filtered through a 20 micron strainer before microfluidic processing. Recovered output (vs filtered input) cells are rigorously analyzed. Erythrocytes, leukocytes, and leukocyte subsets are quantified by Coulter and Hemavet technologies. Viability of output leukocytes are confirmed by trypan blue dye exclusion with counting by manual and automated (Countess) methods. Apoptosis and cell death are measured using Annexin V/7AAD staining and flow cytometry. Leukocyte subtypes are quantified by immunostaining and flow cytometry. The number of CD34+HSPCs are evaluated using Procount kits.

Optical imaging tools (FIG. 17) show any blockages and can be observed in real time. The removal of large cell clumps by filtration through a cell strainer reduces clogging in the device. To minimize cell clumping in the system, the input reservoirs are agitated (undulating rocking, per blood bank routines). To avoid cell aggregation at the beginning of

TABLE 2

|  | Starting | Product 1 | Product 2 | Product 3 | Product 4 | Product 5 |
|---|---|---|---|---|---|---|
| WBC count (K/ul) | 5.36 | 2.16 | 2.60 | 1.62 | 2.54 | 1.64 |
| RBC count (M/ul) | 2.41 | <0.01* | <0.01* | <0.01* | <0.01* | <0.01* |
| Volume (ml) | 3.00 | 0.45 | 0.42 | 0.47 | 3.5 | 1 |
| Yield | | 87% (for the combined Products) | | | | |
| % Viability | >90 | >90 | >90 | >90 | >90 | >90 |
| % Purity | 0.54 | 81 | 88 | Not done | 86 | Not done |
| % Granulocytes | 63.9 | 61.6 | 56.8 | Not done | 51.9 | Not done |
| % Lymphocytes | 18.6 | 17.8 | 21.1 | Not done | 25.7 | Not done |
| % Monocytes | 7.21 | 6.61 | 7.19 | Not done | 9.83 | Not done |

Table 2 shows results of leukocyte enrichment from UCB. The starting sample is 3 ml of one day old UCB, diluted 1:1 with running buffer (PBS, 2 mM EDTA, 1% BSA). The leukocyte-enriched output product contains erythrocyte levels below Hemavet detection, so product purity is determined by multicolor FACS analysis using labels against CD45, CD14, CD235a, and a viable nucleic acid dye. For the combined fractions erythrocyte depletion is 99%, leukocyte recovery is 87%, and leukocyte purity is 81-88%. Purities may be reduced by microscopic cell clumping. There is some dead volume in our current instrument the DLD microarray, the gap spacing is widened in the first post array. In some cases, the cell concentration is lowered by further dilution of the starting sample to avoid clumping. In some cases, the concentration of BSA is increased in the sample buffer from 0.1% to 5%, as albumin binding to all surfaces reduced clogging in magnetic separation technology.

To avoid clumping, short bursts of higher pressure can be applied across the device, which can disrupt cell clumps and cause large objects to deform and move through gaps. In some cases, pressure bursts in the reverse direction loosen clumped or stuck cells. In some embodiments, asymmetric microposts are used to increase the size of the gap for a given critical separation size, which would be less prone to clumping. In some cases, flow rates of >10 fold higher than used in previous DLD work. In some cases, such high flow rates can reduce the amount of cell aggregation and sticking in the microchip, presumably because the high viscous drag forces on any clumps is large enough to disperse them.

When the device and protocols are optimized to routinely produce output leukocytes meeting our 90/90/90 criteria, a series of 10 or more successive experiments (sample number subject to statistical significance and power) are conducted where leukocytes from a given donor are separated simultaneously in the microfluidic device versus by an experienced individual using Ficoll-Paque or HES, standard clinical techniques for erythrocyte depletion of UCB. Statistical comparisons of viability, yield, purity, and leukocyte subsets are performed.

Example 3—Increase Throughput to >100 ml/hr

In some cases, the throughput rate is scaled from 10 ml/hr in the system to >100 ml/hr. The most straightforward approach is to run the chips at a higher pressure differential. The system can operate at ~5 mm/sec fluid speed in the chips. Increasing the driving pressure, the DLD method works well at speeds of at least 150 mm/sec (a 30× increase) to separate leukocytes from adult blood, while still maintaining 99% viability of the leukocytes. This speed corresponds to a chip throughput of 300 ml/hour. (And human cancer cells (mdamb231 cell line) have been processed at speeds up to 1000 mm/sec, also still maintaining 99% viability).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for purifying leukocytes for therapeutic use from a sample comprising leukocytes and erythrocytes, the method comprising:
   (a) providing a sample comprising erythrocytes and leukocytes, wherein the sample volume is at least 100 ml and less than 300 mL;
   (b) separating said erythrocytes from said leukocytes by deterministic lateral displacement on a microfluidic device, wherein said microfluidic device comprises posts with one or more non-rounded vertices, wherein said posts are organized into an array of rows and columns such that adjacent posts form a gap through which fluid may pass and adjacent columns are offset from one another to form an array direction that differs from the flow direction of the device by a tilt angle (c) and wherein the array has a critical diameter such that, when said sample is flowed through the device, leukocytes travel in the array direction and erythrocytes travel in the direction of fluid flow;
   (c) collecting a product from said microfluidic device, wherein: i) the product comprises leukocytes; ii) relative to the sample applied to the device, the product is depleted in erythrocytes; and iii) the product comprises less than 10% erythrocytes;
   wherein the device is operated at a flow rate of at least 100 ml per hour and a linear flow rate of 5 mm/sec to 150 mm/sec, and wherein greater than 90% of the leukocytes collected in the product are viable.

2. The method of claim 1 wherein adjacent posts define a gap through which fluid flows and at least one vertex of a post points into the gap and wherein the erythrocytes in the sample are reduced by greater than 99% in the product.

3. The method of claim 1, wherein said posts have at least one vertex in which a ratio of the radius of curvature to characteristic dimension is not greater than 0.25.

4. The method of claim 1, wherein said posts are triangular.

5. The method of claim 1, wherein said posts are square, rectangular, trapezoidal or hexagonal.

6. The method of claim 1, wherein said device is operated at a flow rate of 100-300 ml/hr and wherein the cells isolated are suitable for transplantation.

7. The method of claim 1, wherein said device is operated at a fluid speed of at least 150/mm/sec.

8. The method of claim 1, wherein the product comprising leukocytes includes hematopoietic stem cells.

9. The method of claim 1, wherein the product has a yield of leukocytes of greater than 90%.

10. The method of claim 1, wherein the method does not use centrifugation or differential sedimentation.

11. The method of claim 1, wherein the sample is umbilical cord blood.

12. The method of claim 11, wherein the umbilical cord blood is not cryopreserved.

13. The method of claim 11, wherein the method does not use centrifugation or differential sedimentation.

14. The method of claim 11, wherein the posts in the microfluidic device are triangular.

15. The method of claim 11, wherein the posts in the microfluidic device are square, rectangular, trapezoidal or hexagonal.

16. The method of claim 1, wherein the microfluidic device is operated at a flow rate of 100-300 ml/hr and the erythrocytes in the sample are reduced by greater than 99% in the product.

17. A method for purifying leukocytes for therapeutic use from a sample comprising leukocytes and erythrocytes, the method comprising:
   (a) providing a sample comprising erythrocytes and leukocytes, wherein the sample volume is at least 100 ml;
   (b) separating said erythrocytes from said leukocytes by deterministic lateral displacement on a microfluidic device, wherein said microfluidic device comprises posts with one or more non-rounded vertices, wherein said posts are organized into an array of rows and columns such that adjacent posts form a gap through which fluid may pass and adjacent columns are offset from one another to form an array direction that differs from the flow direction of the device by a tilt angle (c) and wherein the array has a critical diameter such that, when said sample is flowed through the device, leukocytes travel in the array direction and erythrocytes travel in the direction of fluid flow;
   (c) collecting a product comprising leukocytes from said microfluidic device;
   wherein:
   i) relative to the sample applied to the device, the product is depleted in erythrocytes;

ii) the product comprises less than 0.01 M/µl of erythrocytes;
iii) the device is operated at a linear flow rate of 5 mm/sec to 150 mm/sec,
iv) greater than 90% of the leukocytes collected in the product are viable.

18. The method of claim 17, wherein the erythrocytes in the sample are reduced by greater than 99% in the product.

19. The method of claim 18, wherein the product has a yield of leukocytes of greater than 90%.

20. The method of claim 18, wherein the method is performed in less than one hour and does not use centrifugation.

21. The method of claim 17, wherein the product has a yield of leukocytes of greater than 90%.

22. The method of claim 21, wherein the product comprising leukocytes includes hematopoietic stem cells.

23. The method of claim 17, wherein the product comprising leukocytes includes hematopoietic stem cells.

* * * * *